(12) United States Patent
Prieve et al.

(10) Patent No.: US 9,464,300 B2
(45) Date of Patent: Oct. 11, 2016

(54) MULTIBLOCK COPOLYMERS

(75) Inventors: Mary G. Prieve, Lake Forest Park, WA (US); Paul H. Johnson, Snohomish, WA (US); Patrick S. Stayton, Seattle, WA (US); Allan S. Hoffman, Seattle, WA (US); Robert W. Overell, Shoreline, WA (US); Anna S. Gall, Woodinville, WA (US); Amber E. E. Paschal, Redmond, WA (US); Charbel Diab, Seattle, WA (US); Priyadarsi De, West Bengal (IN); Michael S. DeClue, Seattle, WA (US); Sean D. Monahan, Lake Forest Park, WA (US)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 626 days.

(21) Appl. No.: 13/127,959

(22) PCT Filed: Nov. 6, 2009

(86) PCT No.: PCT/US2009/063648
§ 371 (c)(1),
(2), (4) Date: Jul. 27, 2011

(87) PCT Pub. No.: WO2010/054266
PCT Pub. Date: May 14, 2010

(65) Prior Publication Data
US 2011/0286957 A1  Nov. 24, 2011

Related U.S. Application Data

(60) Provisional application No. 61/243,898, filed on Sep. 18, 2009, provisional application No. 61/177,921, filed on May 13, 2009, provisional application No. 61/171,369, filed on Apr. 21, 2009, provisional application No. 61/171,358, filed on Apr. 21, 2009, provisional application No. 61/140,779, filed on Dec. 24, 2008, provisional application No. 61/140,774, filed on Dec. 24, 2008, provisional application No. 61/112,054, filed on Nov. 6, 2008, provisional application No. 61/112,048, filed on Nov. 6, 2008.

(51) Int. Cl.
| | |
|---|---|
| *C12N 15/87* | (2006.01) |
| *C08F 293/00* | (2006.01) |
| *A61K 31/713* | (2006.01) |
| *A61K 48/00* | (2006.01) |
| *C08F 220/28* | (2006.01) |

(52) U.S. Cl.
CPC ............. *C12N 15/87* (2013.01); *A61K 31/713* (2013.01); *C08F 293/005* (2013.01); *A61K 48/00* (2013.01); *C08F 2220/286* (2013.01); *C08F 2438/03* (2013.01)

(58) Field of Classification Search
CPC ................ A61K 47/48176; A61K 48/00
See application file for complete search history.

(56) References Cited

U.S. PATENT DOCUMENTS

| | | |
|---|---|---|
| 4,699,784 A | 10/1987 | Shih |
| 5,057,313 A | 10/1991 | Shih |
| 6,359,054 B1 | 3/2002 | Lemieux |
| 6,383,811 B2 | 5/2002 | Wolff |
| 6,410,057 B1 | 6/2002 | Kweon-Choi |
| 6,780,428 B2 | 8/2004 | Ranger |
| 6,835,393 B2 | 12/2004 | Hoffman |
| 6,919,091 B2 | 7/2005 | Trubetskoy |
| 6,939,564 B2 | 9/2005 | Ranger |
| 7,033,607 B2 | 4/2006 | Trubetskoy |
| 7,094,810 B2 | 8/2006 | Sant |
| 7,098,032 B2 | 8/2006 | Trubetskoy |
| 7,217,776 B1 | 5/2007 | Mallapragada |
| 7,374,778 B2 | 5/2008 | Hoffman |
| 7,510,731 B2 | 3/2009 | Ranger |
| 7,524,680 B2 | 4/2009 | Wolff |
| 7,718,193 B2 | 5/2010 | Stayton |
| 7,737,108 B1 | 6/2010 | Hoffman |
| 8,367,113 B2 | 2/2013 | Gu |
| 2001/0007666 A1 | 7/2001 | Hoffman |
| 2002/0172711 A1 | 11/2002 | Martin |
| 2003/0013133 A1 | 1/2003 | Kataoka |
| 2003/0134420 A1 | 7/2003 | Lollo |
| 2003/0191081 A1 | 10/2003 | Lemieux |
| 2003/0211167 A1 | 11/2003 | Gustavsson |
| 2004/0054127 A1* | 3/2004 | Jin .............................. 528/422 |
| 2004/0072784 A1 | 4/2004 | Sant |
| 2004/0138095 A1 | 7/2004 | Soula |
| 2004/0151775 A1 | 8/2004 | Rozema |
| 2004/0162235 A1 | 8/2004 | Trubetskoy |

(Continued)

FOREIGN PATENT DOCUMENTS

| | | |
|---|---|---|
| EP | 0 321 233 A1 | 6/1989 |
| EP | 2 180 004 A1 | 4/2010 |

(Continued)

OTHER PUBLICATIONS

Fishbein, I., et al., "Local Delivery of Gene Vectors From Bare-Metal Stents by Use of a Biodegradable Synthetic Complex Inihibits In-Stent Restenosis in Rat Carotid Arteries," Circulation 117(16):2096-2103, Apr. 2008.
Invitiation to Pay Additional Fees and Partial International Search Report mailed Apr. 26, 2011, issued in corresponding International Application No. PCT/US2010/056993, filed Nov. 17, 2010, 6 pages.
Varghese, O.P., et al., "In Situ Cross-Linkable High Molecular Weight Hyaluronan-Bisphosphonate Conjugate for Localized Delivery and Cell-Specific Targeting: A Hydrogel Linked Prodrug Approach," Journal of the American Chemical Society 131(25):8781-8783, Jul. 2009.
Cho, Y.W., et al., "Polycation Gene Delivery Systems: Escape From Endosomes to Cytosol," Journal of Pharmacy and Pharmacology 55(6):721-734, Jun. 2003.

(Continued)

*Primary Examiner* — Addison D Ault
(74) *Attorney, Agent, or Firm* — Christensen O'Connor Johnson Kindness PLLC

(57) ABSTRACT

Provided herein are multiblock copolymers, as well as micelles and therapeutic compositions thereof.

12 Claims, 8 Drawing Sheets

(56) References Cited

U.S. PATENT DOCUMENTS

| | | |
|---|---|---|
| 2005/0070721 A1 | 3/2005 | Bae |
| 2005/0220880 A1 | 10/2005 | Lewis |
| 2005/0260276 A1 | 11/2005 | Yang |
| 2006/0134221 A1 | 6/2006 | Geall |
| 2006/0165810 A1 | 7/2006 | Discher |
| 2006/0171980 A1 | 8/2006 | Helmus |
| 2006/0217285 A1 | 9/2006 | Destarac |
| 2006/0235161 A1 | 10/2006 | Heller |
| 2006/0240092 A1 | 10/2006 | Breitenkamp |
| 2007/0003609 A1 | 1/2007 | Collin-Djangone |
| 2007/0010632 A1 | 1/2007 | Kaplan |
| 2007/0037891 A1 | 2/2007 | Esfand |
| 2007/0059271 A1 | 3/2007 | Kataoka |
| 2007/0110709 A1 | 5/2007 | Ranger |
| 2007/0224241 A1 | 9/2007 | Stayton |
| 2007/0299240 A1 | 12/2007 | Gopferich |
| 2008/0069902 A1 | 3/2008 | Zhao |
| 2008/0081075 A1 | 4/2008 | Hsiue |
| 2008/0171067 A1 | 7/2008 | Govindan |
| 2008/0243049 A1 | 10/2008 | Hardy |
| 2009/0023890 A1* | 1/2009 | Monahan et al. ............ 528/422 |
| 2009/0036625 A1 | 2/2009 | Chang |
| 2010/0150952 A1 | 6/2010 | Stayton |
| 2011/0123636 A1 | 5/2011 | Stayton |
| 2011/0143434 A1 | 6/2011 | Stayton |
| 2011/0143435 A1 | 6/2011 | Stayton |
| 2011/0281354 A1 | 11/2011 | Stayton |
| 2011/0281934 A1 | 11/2011 | Johnson |
| 2012/0021514 A1 | 1/2012 | Johnson |
| 2013/0017167 A1 | 1/2013 | Monahan |
| 2014/0228516 A1 | 8/2014 | Stayton |

FOREIGN PATENT DOCUMENTS

| | | |
|---|---|---|
| FR | 2 767 829 A1 | 3/1999 |
| WO | 99/29303 A1 | 6/1999 |
| WO | 01/87227 A2 | 11/2001 |
| WO | 03/087188 A1 | 10/2003 |
| WO | 2005/108614 A2 | 11/2005 |
| WO | 2006/016166 A1 | 2/2006 |
| WO | 2007/008300 A2 | 1/2007 |
| WO | 2007/109584 A1 | 9/2007 |
| WO | 2008/003099 A1 | 1/2008 |
| WO | 2008/004978 A1 | 1/2008 |
| WO | 2008/022309 A2 | 2/2008 |
| WO | 2008/071009 A1 | 6/2008 |
| WO | 2008/079677 A2 | 7/2008 |
| WO | 2008/085556 A2 | 7/2008 |
| WO | 2008/148174 A1 | 12/2008 |
| WO | 2008/153940 A1 | 12/2008 |
| WO | 2009/009025 A1 | 1/2009 |
| WO | 2009/021728 A2 | 2/2009 |
| WO | 2009/140421 A2 | 11/2009 |
| WO | 2009/140423 A2 | 11/2009 |
| WO | 2009/140427 A2 | 11/2009 |
| WO | 2009/140429 A2 | 11/2009 |
| WO | 2009/140432 A2 | 11/2009 |
| WO | 2010/021770 A1 | 2/2010 |
| WO | 2010/053596 A1 | 5/2010 |
| WO | 2010/053597 A2 | 5/2010 |
| WO | 2010/054266 A2 | 5/2010 |
| WO | 2010/077678 A2 | 7/2010 |

OTHER PUBLICATIONS

Convertine, A.J., et al., "Development of a Novel Endosomolytic Diblock Copolymer for siRNA Delivery," Journal of Controlled Release 133(3):221-229, Feb. 2009.

International Search Report and Written Opinion mailed Mar. 7, 2011, issued in corresponding International Application No. PCT/US2010/056565, filed Nov. 12, 2010, 12 pages.

Jeong, J.H., et al., "siRNA Conjugate Delivery Systems," Bioconjugate Chemistry 20(1):5-14, Jan. 2009.

Meyer, M., et al., "Synthesis and Biological Evaluation of a Bioresponsive and Endosomolytic siRNA—Polymer Conjugate," Molecular Pharmaceutics 6(3):752-762, May-Jun. 2009.

Oishi, M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

Hungarian Intellectual Property Office Search Report and Written Opinion mailed Apr. 5, 2012, issued in corresponding Singapore Application No. 201103187-9, filed Nov. 6, 2009, 13 pages.

First Office Action, mailed Jun. 4, 2013, issued in corresponding Japanese Application No. 2011-534933, filed Nov. 6, 2009, 3 pages.

Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by RAFT Polymerization," Chemical Communications 28(28):3245-3247, Jul. 2008.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared Via the RAFT Copolymerization Technique," Biomacromolecules 7(10):2736-2741, Oct. 2006.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Oishi M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

(56) References Cited

OTHER PUBLICATIONS

Peppas, N.A., "Is There a Future in Glucose-Sensitive, Responsive Insulin Delivery Systems?" Drug Delivery Science and Technology 14(4):247-256, Sep. 2004.
Read, M.L., et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.
Segura, T., and J.A. Hubbell, "Synthesis and in Vitro Characterization of an ABC Triblock Copolymer for siRNA Delivery," Bioconjugate Chemistry 18(3):736-745, May 2007.
Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.
Stayton, P.S., et al., "Intelligent Biohybrid Materials for Therapeutic and Imaging Agent Delivery," Proceedings of the IEEE 93(4):726-736, Apr. 2005.
Torchilin, V.P., "Micellar Nanocarriers: Pharmaceutical Perspectives," Pharmaceutical Research 24(1):1-16, Jan. 2007.
Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.
Yamamoto, S.-I., et al., "Temperature- and pH-Responsive Dense Copolymer Brushes Prepared by ATRP," Macromolecules 41(19):7013-7020, Oct. 2008.
Yessine, M.-A., et al., "Proton-Actuated Membrane-Destabilizing Polyion Complex Micelles," Bioconjugate Chemistry 18(3):1010-1014, May-Jun. 2007.
International Search Report and Written Opinion mailed May 28, 2010, issued in corresponding International Application No. PCT/US2009/063648, filed Nov. 6, 2009, 10 pages.
Extended European Search Report mailed Feb. 5, 2014, issued in corresponding European Application No. 09 825 146.5, filed May 13, 2009, 9 pages.
Cheung, C.Y., et al., "A pH-Sensitive Polymer That Enhances Cationic Lipid-Mediated Gene Transfer," Bioconjugate Chemistry 12(6):906-910, Oct. 2001.
Hood, J.D., et al., "Tumor Regression by Targeted Gene Delivery to the Neovasculature," Science, New Series 296 (5577):2404-2407, Jun. 2002.
Jeong, Y.-I., et al., "Cellular Recognition of Paclitaxel-Loaded Polymeric Nanoparticles Composed of Poly(y-benzyl L-glutamate) and Poly(ethylene glycol) Diblock Copolymer Endcapped With Galactose Moiety," International Journal of Pharmaceutics 296(2005):151-161, Apr. 2005.
Joralemon, M.J., et al., "Synthesis, Characterization, and Bioavailability of Mannosylated Shell Cross-Linked Nanoparticles," Biomacromolecules 5(3):903-913, May-Jun. 2004.
Kabanov, A.V., et al., "Pluronic Micelles as a Tool for Low-Molecular Compound Vector Delivery Into a Cell: Effect of *Staphylococcus-aureus* Enterotoxin B on Cell Loading With Micelle Incorporated Fluorescent Dye," Biochemistry International 26(6):1035-1042, May 1992.
Kyriakides, T.R., et al., "pH-Sensitive Polymers That Enhance Intracellular Drug Delivery in Vivo," Journal of Controlled Release 78(1-3):295-303, Jan. 2002.
Le Garrec, D., et al., "Micelles in Anticancer Drug Delivery," American Journal of Drug Delivery 2(1):15-42, Mar. 2004.
Lee, E.S., et al., "Super pH-Sensitive Multifunctional Polymeric Micelle," Nano Letters 5(2):325-329, Feb. 2005.
Nagasaki, Y. et al., "Sugar-Installed Block Copolymer Micelles: Their Preparation and Specific Interaction With Lectin Molecules," Biomacromolecules 2(4):1067-1070, Winter 2001.
Raso, V., "Intracellular Targeting Using Bispecific Antibodies," Methods in Molecular Medicine 25:37-49, Jan. 2000.
Sawant, R.M., et al., "'Smart'" Drug Delivery Systems: Double-Targeted pH-Responsive Pharmaceutical Nanocarriers, Bioconjugate Chemistry 17:943-949, Jun. 2006.
Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.
Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.
Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.
Yoo, H.S., and T.G. Park, "Folate Receptor Targeted Biodegradable Polymeric Doxorubicin Micelles," Journal of Controlled Release 96(2):273-283, Apr. 2004.
Cheng, Z., et al., "Brush-Type Amphiphilic Diblock Copolymers from 'Living'/Controlled Radical Polymerizations and Their Aggregation Behavior," Langmuir 21(16):7180-7185, Jul. 2005.
Finne-Wistrand, A. and A.-C. Albertson, "The Use of Polymer Design in Resorbable Colloids," Annual Review of Materials Research 36:369-395, Aug. 2006.
Oishi M., et al., "pH-Responsive Oligodeoxynucleotide (ODN)-Poly(Ethylene Glycol) Conjugate Through Acid-Labile β-Thiopropionate Linkage: Preparation and Polyion Complex Micelle Formation," Biomacromolecules 4(5):1426-1432, Aug. 2003.
Vazquez-Dorbatt, V. et al., "Synthesis of a Pyridyl Disulfide End-Functionalized Glycopolymer for Conjugation to Biomolecules and Patterning on Gold Surfaces," Biomacromolecules 10(8):2207-2212, Jul. 2009.
Wei, J.-S., et al., "Temperature- and pH-Sensitive Core-Shell Nanoparticles Self-Assembled from Poly(N-Isopropylacrylamide-CO-Acrylic Acid-CO-Cholesteryl Acrylate) for Intracellular Delivery of Anticancer Drugs," Frontiers in Bioscience 10:3058-3067, Sep. 2005.
Office Action mailed May 20, 2015, from U.S. Appl. No. 13/127,962, filed Jul. 26, 2011, 10 pages.
Stayton, P.S., "Polymeric Carrier," U.S. Appl. No. 14/630,477, filed Feb. 24, 2015.
Agarwal, A., et al., "Dual-Role Self-Assembling Nanoplexes for Efficient Gene Transfection and Sustained Gene Delivery," Biomaterials 29(5):607-617, Feb. 2008.
Alvarez-Lorenzo, C., et al., "Biophysical Characterization of Complexation of DNA with Block Copolymers of Poly(2-dimethylaminoethyl) Methacrylate, Poly(ethylene oxide), and Poly-(propylene oxide)," Langmuir 21(11):5142-5148, May 24, 2005.
Boeckle, S., et al., "Purification of Polyethylenimine Polyplexes Highlights the Role of Free Polycations in Gene Transfer," The Journal of Gene Medicine 6(10):1102-1111, Oct. 2004.
Eliyahu, H., et al., "Novel Dextran-Spermine Conjugates as Transfecting Agents: Comparing Water-Soluble and Micellar Polymers," Gene Therapy 12(6):494-503, Mar. 2005.
Final Office Action mailed Mar. 21, 2014, from U.S. Appl. No. 13/127,962, filed Jul. 26, 2011, 11 pages.
Gary, D.J., et al., "Polymer-Based siRNA Delivery: Perspectives on the Fundamental and Phenomenological Distinctions from Polymer-Based DNA Delivery," Journal of Controlled Release 121(1-2):64-73, Aug. 16, 2007.
Germershaus, O., et al., "Gene Delivery Using Chitosan, Trimethyl Chitosan or Polyethylenglycol-graft-trimethyl Chitosan Block Copolymers: Establishment of Structure-Activity Relationships in Vitro," Journal of Controlled Release 125(2):145-154, Jan. 22, 2008.
Guo, Y., et al., "Capillary Electrophoresis Analysis of Poly(ethylene glycol) and Ligand-Modified Polylysine Gene Delivery Vectors," Analytical Biochemistry 363(2):204-209, Apr. 15, 2007.
Jiang, T., et al., "Adsorption of Plasmid DNA onto N,N'-(Dimethylamino)ethyl-methacrylate Graft-Polymerized Poly-L-

(56) References Cited

OTHER PUBLICATIONS

Lactic Acid Film Surface for Promotion of In-Situ Gene Delivery," Biomacromolecules 8(6):1951-1957, Jun. 2007.

Kim, E.-M., et al., "Monitoring the Effect of PEGylation on Polyethylenimine in Vivo Using Nuclear Imaging Technique," Nuclear Medicine and Biology, 31(6):781-784, Aug. 2004.

Kono, K., et al., "Transfection Activity of Polyamidoamine Dendrimers Having Hydrophobic Amino Acid Residues in the Periphery," Bioconjugate Chemistry 16(1):208-214, Jan. 2005.

Kurisawa, M., et al., "Transfection Efficiency Increases by Incorporating Hydrophobic Monomer Units into Polymeric Gene Carriers," Journal of Controlled Release, 68(1):1-8, Jul. 31, 2000.

Lam, J.K.W., et al., "Phosphocoline-Polycation Diblock Copolymers as Synthetic Vectors for Gene Delivery," Journal of Controlled Release 100(2):293-312, Nov. 24, 2004.

Lomas, H., et al., "Biomimetic pH Sensitive Polymersomes for Efficient DNA Encapsulation and Delivery," Advanced Materials 19(23):4238-4243, Dec. 2007.

Neu, M., et al., "Recent Advances in Rational Gene Transfer Vector Design Based on Poly(ethylene imine) and its Derivatives," Journal of Gene Medicine 7(8):992-1009, Aug. 2005.

Ogris, M., et al., "PEGylated DNA/transferrin-PEI Complexes: Reduced Interaction with Blood Components, Extended Circulation in Blood and Potential for Systemic Gene Delivery," Gene Therapy 6(4):595-605, Apr. 1999.

Oupicky, D., et al., "DNA Delivery Systems Based on Complexes of DNA with Synthetic Polycations and Their Copolymers," Journal of Controlled Release 65(1-2):149-171, Mar. 1, 2000.

Scales, C.W., et al., "Corona-Stabilized Interpolyelectrolyte Complexes of SiRNA with Nonimmunogenic, Hydrophilic/Cationic Block Copolymers Prepared by Aqueous RAFT Polymerization," Macromolecules 39(20):6871-6881, Oct. 3, 2006.

Takeda, N., et al., "Temperature-Responsive Polymeric Carriers Incorporating Hydrophobic Monomers for Effective Transfection in Small Doses," Journal of Controlled Release 95(2):343-355, Mar. 5, 2004.

Veron, L., et al., "Hydrolyzable p(DMAPEMA) Polymers for Gene Delivery," Macromolecular Bioscience 6(7):540-554, Jul. 14, 2006.

Yu, H., et al., "A Novel Amphiphilic Double-[60]Fullerene-Capped Triblock Copolymer," Macromolecules 38(23):9889-9893, Nov. 15, 2005.

Zhao, X., et al.,"Nanostructure of Polyplexes Formed Between Cationic Diblock Copolymer and Antisense Oligodeoxynucleotide and its Influence on Cell Transfection Efficiency," Biomacromolecules 8(11):3493-3502, Nov. 12, 2007.

York, A.W. et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.

Stayton, P.S., "Bispecific Intracellular Delivery Vehicles," U.S. Appl. No. 14/957,429, filed Dec. 2, 2015.

Final Office Action mailed Dec. 3, 2015, from U.S. Appl. No. 13/127,962, filed Jul. 26, 2011, 11 pages.

Stayton, P.S., et al., "Micellic Assemblies," U.S. Appl. No. 15/059,026, filed Mar. 2, 2016.

* cited by examiner

Fig. 1  Synthesis of poly(PEGMA-MANHS)-b-(DMAEMA)

Fig. 3  Characterization of poly(PEGMA-MANHS)-b-(DMAEMA): Gel Permeation Chromatography (GPC) Analysis Fig. 4 Synthesis of poly[(PEGMA-MANHS)-b-(DMAEMA)-b-[(DMAEMA)-(BMA)-(PAA)]

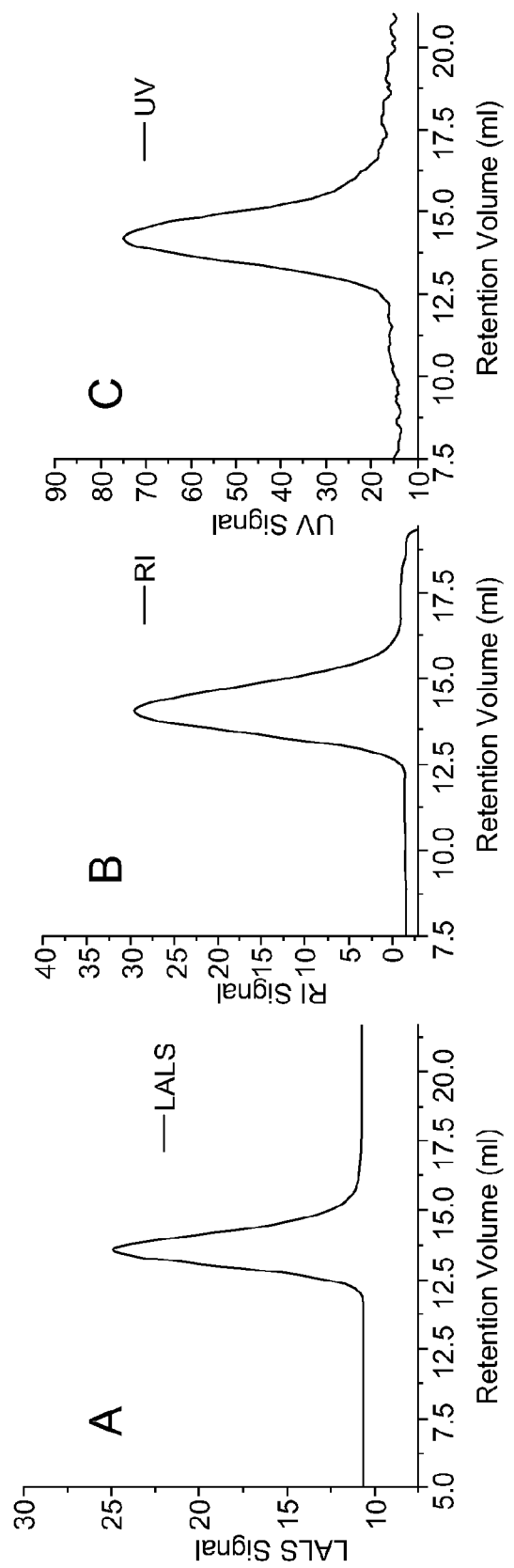
Fig. 6  Characterization of poly(PEGMA-MANHS)-b-(DMAEMA)-b-[(DMAEMA)-(BMA)-(PAA)]: GPC Analysis

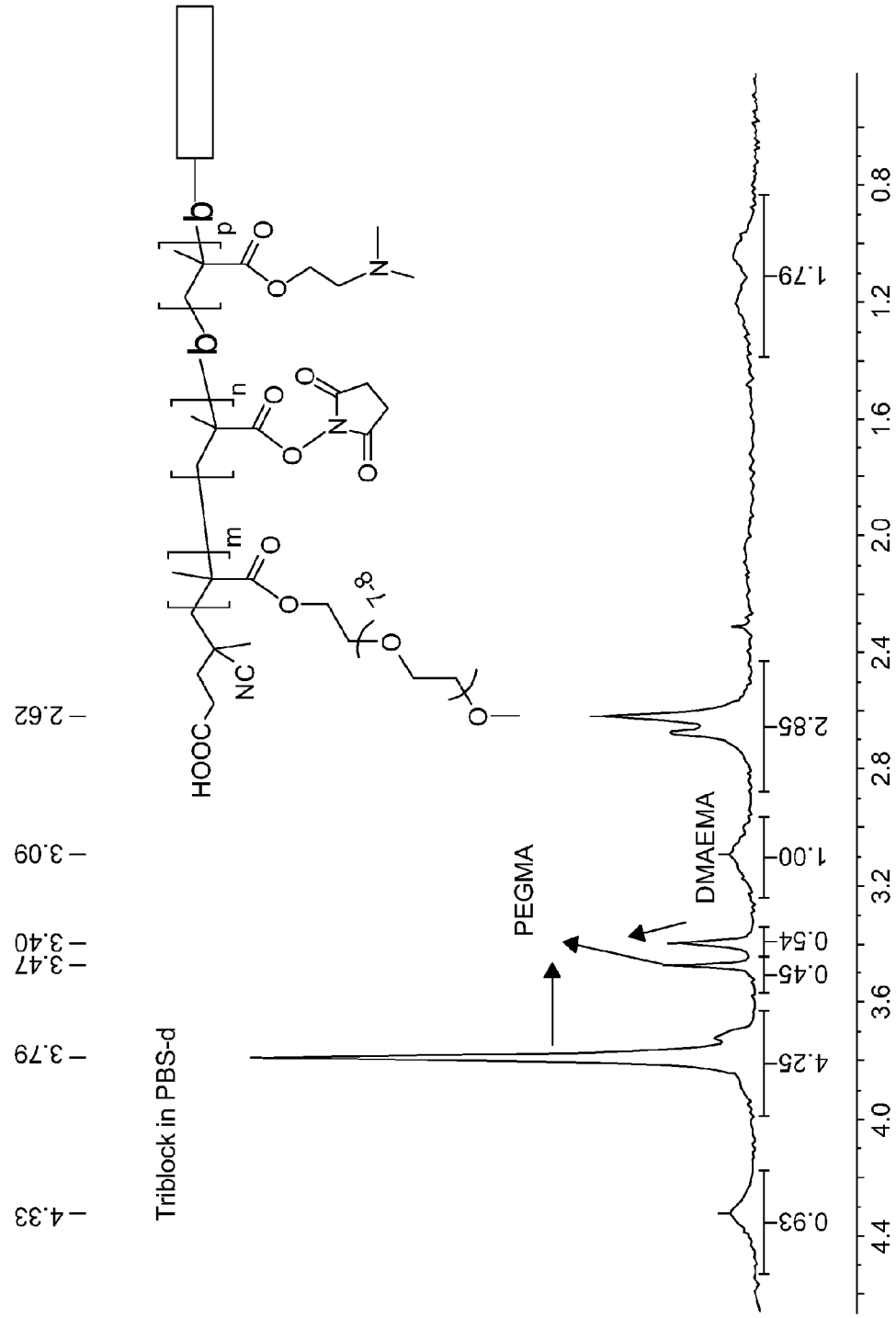
Fig. 7 Characterization of poly(PEGMA-MANHS)-b-(DMAEMA)-b-[(DMAEMA)-(BMA)-(PAA)]: NMR Analysis in PBS-d

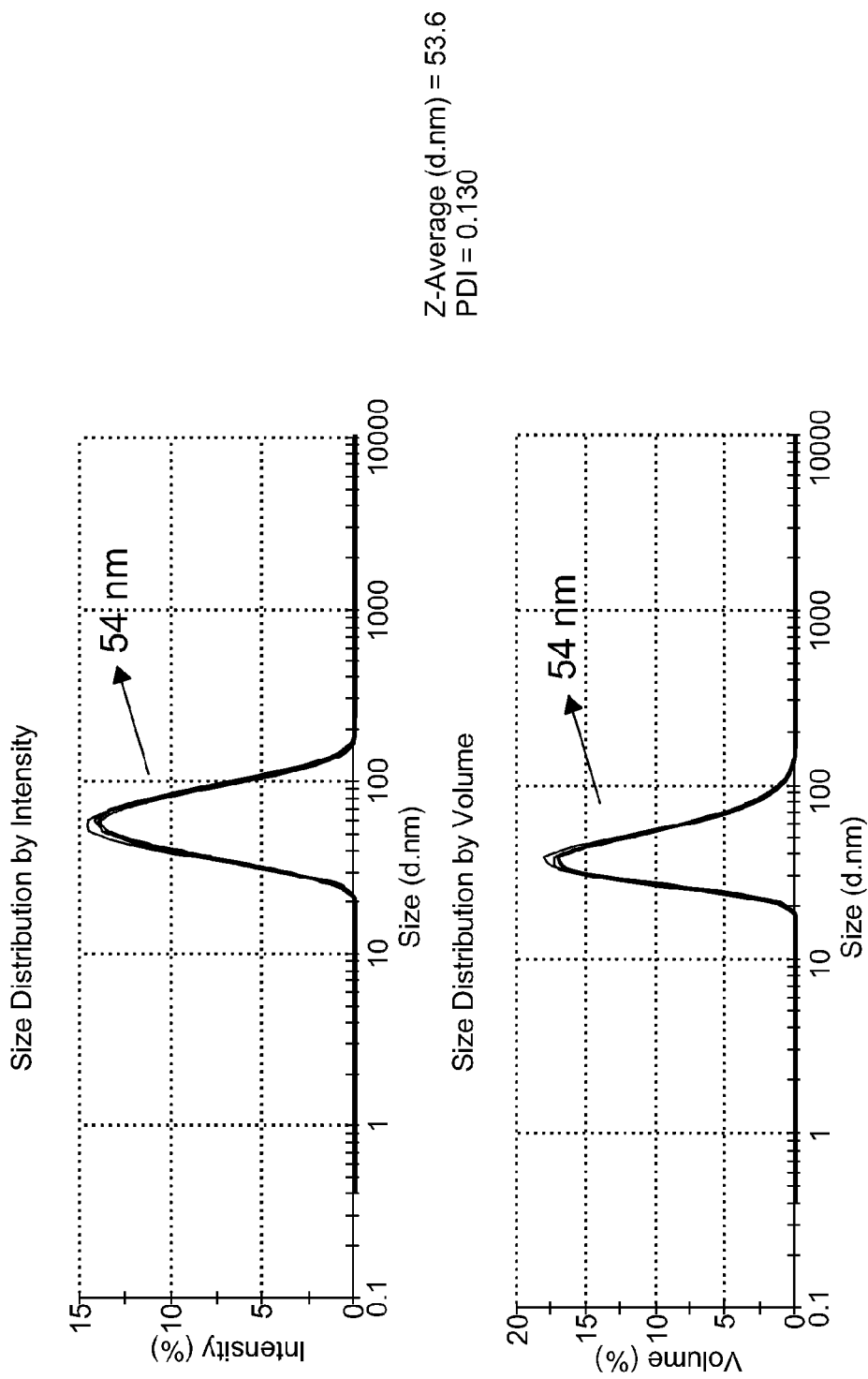
Fig. 8  Characterization of poly(PEGMA-MANHS)-b-(DMAEMA)-b-[(DMAEMA)-(BMA)-(PAA)]: Dynamic light scattering (DLS)

SEQUENCE LISTING

<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: Wherein each of the nucleotides from position
      1 to 19 are modified ribonucleotides.
<220> FEATURE:
<221> NAME/KEY: misc_feature
<222> LOCATION: (1)..(21)
<223> OTHER INFORMATION: Sequence is DNA/RNA hybrid.
<220> FEATURE:
<221> NAME/KEY: misc_feature
<222> LOCATION: (20)..(21)
<223> OTHER INFORMATION: Wherein each of the nucleotides from position
      20 to 21 are modified deoxynucleotides.

<400> SEQUENCE: 1
ggucauccau gacaacuuut t                                            21

<210> SEQ ID NO 2
<211> LENGTH: 21
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (1)..(21)
<223> OTHER INFORMATION: Sequence is DNA/RNA hybrid.
<220> FEATURE:
<221> NAME/KEY: misc_feature
<222> LOCATION: (1)..(19)
<223> OTHER INFORMATION: Wherein each of the nucleotides from position
      1 to 19 are modified ribonucleotides.
<220> FEATURE:
<221> NAME/KEY: misc_feature
<222> LOCATION: (20)..(21)
<223> OTHER INFORMATION: Wherein each of the nucleotides from position
      20 to 21 are modified deoxynucleotides.

<400> SEQUENCE: 2
aaaguuguca uggaugacct t                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Wherein the nucleotide at position 1 is
      modified ribonucleotide.
<220> FEATURE:
<221> NAME/KEY: misc_feature
<222> LOCATION: (1)..(21)
<223> OTHER INFORMATION: Sequence is DNA/RNA hybrid.
<220> FEATURE:
<221> NAME/KEY: misc_feature
<222> LOCATION: (2)..(2)
<223> OTHER INFORMATION: Wherein the nucleotide at position 2 is
      2'-O-methyl modified.
<220> FEATURE:
<221> NAME/KEY: misc_feature
<222> LOCATION: (3)..(4)
<223> OTHER INFORMATION: Wherein each of the nucleotides from position
      3 to 4 are modified ribonucleotides.
<220> FEATURE:
<221> NAME/KEY: misc_feature
<222> LOCATION: (5)..(5)
<223> OTHER INFORMATION: Wherein the nucleotide at position 5 is
      2'-O-methyl modified.
<220> FEATURE:
<221> NAME/KEY: misc_feature
<222> LOCATION: (6)..(10)
<223> OTHER INFORMATION: Wherein each of the nucleotides from position
      6 to 10 are modified ribonucleotides.
<220> FEATURE:
<221> NAME/KEY: misc_feature
<222> LOCATION: (11)..(11)
<223> OTHER INFORMATION: Wherein the nucleotide at position 11 is
      2'-O-methyl modified.
<220> FEATURE:
<221> NAME/KEY: misc_feature
<222> LOCATION: (12)..(14)
<223> OTHER INFORMATION: Wherein each of the nucleotides from position
      12 to 14 are modified ribonucleotides.
<220> FEATURE:
<221> NAME/KEY: misc_feature
<222> LOCATION: (15)..(15)
<223> OTHER INFORMATION: Wherein the nucleotide at position 15 is
      2'-O-methyl modified.
<220> FEATURE:
<221> NAME/KEY: misc_feature
<222> LOCATION: (16)..(20)
<223> OTHER INFORMATION: Wherein each of the nucleotides from position
      16 to 20 are modified ribonucleotides.
<220> FEATURE:
<221> NAME/KEY: misc_feature
<222> LOCATION: (21)..(21)
```

<223> OTHER INFORMATION: Wherein the nucleotide at position 21 is
      2'-O-methyl modified.

<400> SEQUENCE: 3
gucaucacac ugaauaccaa u                                           21

<210> SEQ ID NO 4
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: Wherein each of the nucleotides from position
      1 to 23 are modified ribonucleotides.
<220> FEATURE:
<221> NAME/KEY: misc_feature
<222> LOCATION: (1)..(23)
<223> OTHER INFORMATION: Sequence is DNA/RNA hybrid.

<400> SEQUENCE: 4
auugguauuc agugugauga cac                                         23

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
catggccttc cgtgttccta                                             20

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
atgcctgctt caccaccttc t                                           21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
cctaagatga gcgcaagttg aa                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
ccacaggact agaacacctg ct                                          22

<210> SEQ ID NO 9
<211> LENGTH: 22

```
<212> TYPE: DNA
<213> ORGANISM: Artificial Sequence
<220> FEATURE:
<223> OTHER INFORMATION: Synthetic Primer

<400> SEQUENCE: 9
atggaaggga agtggttact gt                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer

<400> SEQUENCE: 10
gctttgtagg tgacctttgg ag                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic Primer

<400> SEQUENCE: 11
aagcacctcc gaaagtacgt g                                               21

<210> SEQ ID NO 12
<211> LENGTH: 23
<212> TYPE: DNA
<213> ORGANISM: Artificial Sequence
<220> FEATURE:
<223> OTHER INFORMATION: Synthetic Primer

<400> SEQUENCE: 12
ctccagctct accttacagt tga                                             23
```

MULTIBLOCK COPOLYMERS

This application is the National Stage of International Application No. PCT/US2009/063648, filed Nov. 6, 2009, which claims priority from U.S. Patent Application Ser. No. 61/112,048, filed Nov. 6, 2008; U.S. Patent Application Ser. No. 61/112,054, filed Nov. 6, 2008; U.S. Patent Application Ser. No. 61/140,774, filed Dec. 24, 2008; U.S. Patent Application Ser. No. 61/140,779, filed Dec. 24, 2008; U.S. Patent Application Ser. No. 61/171,358, filed Apr. 21, 2009, U.S. Patent Application Ser. No. 61/171,369, filed Apr. 21, 2009; U.S. Ser. No. 61/177,921, filed May 13, 2009; and U.S. Patent Application Ser. No. 61/243,898, filed Sep. 18, 2009, the entire contents of each of which are incorporated herein by reference.

STATEMENT OF GOVERNMENT LICENSE RIGHTS

This invention was made with government support under 1R01 EB002991 awarded by the National Institutes of Health. The government has certain rights in the invention.

STATEMENT OF JOINT RESEARCH AGREEMENT

The subject matter of the claimed invention was made as a result of activities undertaken within the scope of a joint research agreement, within the meaning of 35 U.S.C. §103(c)(3) and 37 C.F.R. §1.104(c)(4)(ii), by or on behalf of the University of Washington and PhaseRx, Inc., that was in effect on or before the claimed invention was made.

BACKGROUND OF THE INVENTION

In certain instances, it is beneficial to provide therapeutic agents, such as polynucleotides (e.g., oligonucleotides) to living cells. In some instances, delivery of such polynucleotides to a living cell provides a therapeutic benefit.

SUMMARY OF THE INVENTION

Among the various aspects of the invention is a composition comprising a block copolymer associated with a therapeutic agent (such as a polynucleotide). The block copolymer comprises at least three compositionally distinct blocks. The first of the three blocks is a hydrophilic polymer block. The second of the three blocks is a polymer block, located between the first and third blocks, the second block (i) being associated with the therapeutic agent, or (iii) possessing a functional group for attaching the therapeutic agent. The third block is a hydrophobic polymer block comprising anionic repeat units; the anionic repeat units have a population of anions as substituents thereof that varies in number in a pH dependant manner, the population being greater at pH 7.4 than at pH 5.

Among the various aspects of the present disclosure is a composition comprising a block copolymer associated with a polynucleotide, the block copolymer comprising a first block, the first block being a hydrophilic polymer block suitable for targeting or steric shielding of the polynucleotide, a second block between the first block and a third block, the second block associating with the polynucleotide, and a third block, the third block comprising a hydrophobic pH-dependent, membrane-destabilizing polymer block.

Another aspect of the disclosure is directed to a composition comprising a block copolymer associated with a polynucleotide, the block copolymer comprising a first block, the first block being a hydrophilic polymer block, a second block between the first block and a third block, the second block associating with the polynucleotide, and a third block, the third block being or comprising a polymer block comprising a plurality of hydrophobic monomeric residues and a plurality of anionic monomeric residues.

Another aspect of the disclosure is directed to a composition comprising a block copolymer associated with a polynucleotide, the block copolymer comprising a first block, the first block being a hydrophilic polymer block, a second block between the first block and a third block, the second block being hydrophilic and comprising a plurality of cationic monomeric residues in ionic association with the polynucleotide, and a third block, the third block comprising a hydrophobic pH-dependent, membrane-destabilizing polymer block.

Another aspect of the disclosure is directed to a composition comprising a block copolymer associated with a polynucleotide, the block copolymer comprising a first block, the first block being a hydrophilic polymer block, a second block between the first block and a third block, the second block being a polymer bioconjugate comprising the polynucleotide covalently coupled to the second block, and a third block, the third block being or comprising a hydrophobic pH-dependent, membrane-destabilizing polymer block.

Another aspect of the disclosure is directed to a composition comprising a block copolymer associated with a polynucleotide, the block copolymer comprising a first block, the first block being a hydrophilic polymer block suitable for targeting or steric shielding of the polynucleotide, a second block between the first block and a third block, the second block being a polymer bioconjugate comprising the polynucleotide covalently coupled to the second block, and a third block, the third block being or comprising a polymer block comprising a plurality of hydrophobic monomeric residues and a plurality of anionic monomeric residues.

Yet another aspect of the disclosure is directed to polymeric micelles comprising the compositions described herein.

Provided in certain embodiments herein is a composition comprising a polymeric micelle and a polynucleotide associated with the micelle, the micelle comprising a plurality of block copolymer comprising:
 a. a first block, the first block being a hydrophilic shielding block;
 b. a second block, the second block being between the first block and a third block, the second block being a polynucleotide carrier block; and
 c. a third block, the third block being a hydrophobic pH-dependent, membrane destabilizing block; the plurality of block copolymers associating into the micelle such that the micelle is stable in an aqueous medium at pH 7.4.

Provided in certain embodiments herein is a composition comprising a polymeric micelle and a polynucleotide associated with the micelle, the micelle comprising a plurality of block copolymers comprising:
 a. a first block, the first block being a hydrophilic polymer block suitable for targeting or steric shielding of the polynucleotide,
 b. a second block between the first block and a third block, the second block associating the polynucleotide, and
 c. a third block, the third block comprising a hydrophobic pH-dependent, membrane-destabilizing polymer block, the plurality of block copolymers being associated in micelle, the micelle being stable in an aqueous medium at pH 7.4.

Provided in some embodiments herein is a composition comprising a polymeric micelle and a polynucleotide associated with the micelle, the micelle comprising a plurality of block copolymers comprising:
  a. a first block, the first block being a hydrophilic polymer block,
  b. a second block between the first block and a third block, the second block associating the polynucleotide, and
  c. a third block, the third block being or comprising a polymer block comprising a plurality of hydrophobic monomeric residues and a plurality of anionic monomeric residues, the plurality of block copolymers being associated in the micelle, the micelle being stable in an aqueous medium at pH 7.4.

Provided in certain embodiments herein is a composition comprising a polymeric micelle and a polynucleotide associated with the micelle, the micelle comprising a plurality of block copolymers comprising
  a. a first block, the first block being a hydrophilic polymer block,
  b. a second block between the first block and a third block, the second block being hydrophilic and comprising a plurality of cationic monomeric residues in ionic association with the polynucleotide, and
  c. a third block, the third block comprising a hydrophobic pH-dependent, membrane-destabilizing polymer block, the plurality of block copolymers being associated in the micelle, the micelle being stable in an aqueous medium at pH 7.4.

Provided in some embodiments herein is a composition comprising a polymeric micelle and a polynucleotide associated with the micelle, the micelle comprising a plurality of block copolymers comprising
  a. a first block, the first block being a hydrophilic polymer block,
  b. a second block between the first block and a third block, the second block being a polymer bioconjugate comprising the polynucleotide covalently coupled to the second block, and
  c. a third block, the third block being or comprising a hydrophobic pH-dependent, membrane-destabilizing polymer block, the plurality of block copolymers being associated in the micelle, the micelle being stable in an aqueous medium at pH 7.4.

Another aspect of the disclosure is directed to a method for preparing a composition comprising a polymeric micelle and a polynucleotide associated with the micelle, the method comprising admixing a block copolymer with a first denaturing medium, the block copolymer comprising a first, a second and a third block, the first block being a hydrophilic polymer block, the second block being a hydrophilic polymer block located between the first and third blocks comprising a moiety having the capacity for association with a polynucleotide, the third block being a hydrophobic pH-dependant, membrane destabilizing polymer block, exposing the block copolymer to a second aqueous medium, allowing the block copolymer to associate in the aqueous medium to form a micelle, and associating a polynucleotide with the second block of the block copolymer.

Another aspect of the present invention is a pharmaceutical composition comprising any of the block copolymers or micelles of the present invention.

A further aspect of the present invention is the use of a block copolymer or micelle of the present invention in the manufacture of a medicament.

A further aspect of the present invention is a method for intracellular delivery of a polynucleotide, the method comprising contacting a composition comprising a block copolymer or micelle of the present invention with a cell surface in a medium at a first pH; introducing the composition into an endosomal membrane within the cell through endocytosis; and destabilizing the endosomal membrane, whereby the composition or the polynucleotide is delivered to the cytosol of the cell.

A further aspect of the present invention is a method for modulating the activity of an intracellular target in a cell, the method comprising: delivering a polynucleotide to the cytosol of a cell using a composition comprising a block copolymer or micelle of the present invention, and allowing the polynucleotide to interact with the intracellular target, whereby the activity of the intracellular target is modulated.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 illustrates the characterization of poly[PEGMA-MAA(NHS)]-b-[DMAEMA]-b-[DMAEMA-BMA-PAA] by GPC.

FIG. 7 illustrates the characterization of poly[PEGMA-MAA(NHS)]-b-[DMAEMA]-b-[DMAEMA-BMA-PAA] by NMR in PBS-d.

FIG. 8 illustrates the characterization of poly[PEGMA-MAA(NHS)]-b-[DMAEMA]-b-[DMAEMA-BMA-PAA] by DLS.

ABBREVIATIONS AND DEFINITIONS

Figure 1:
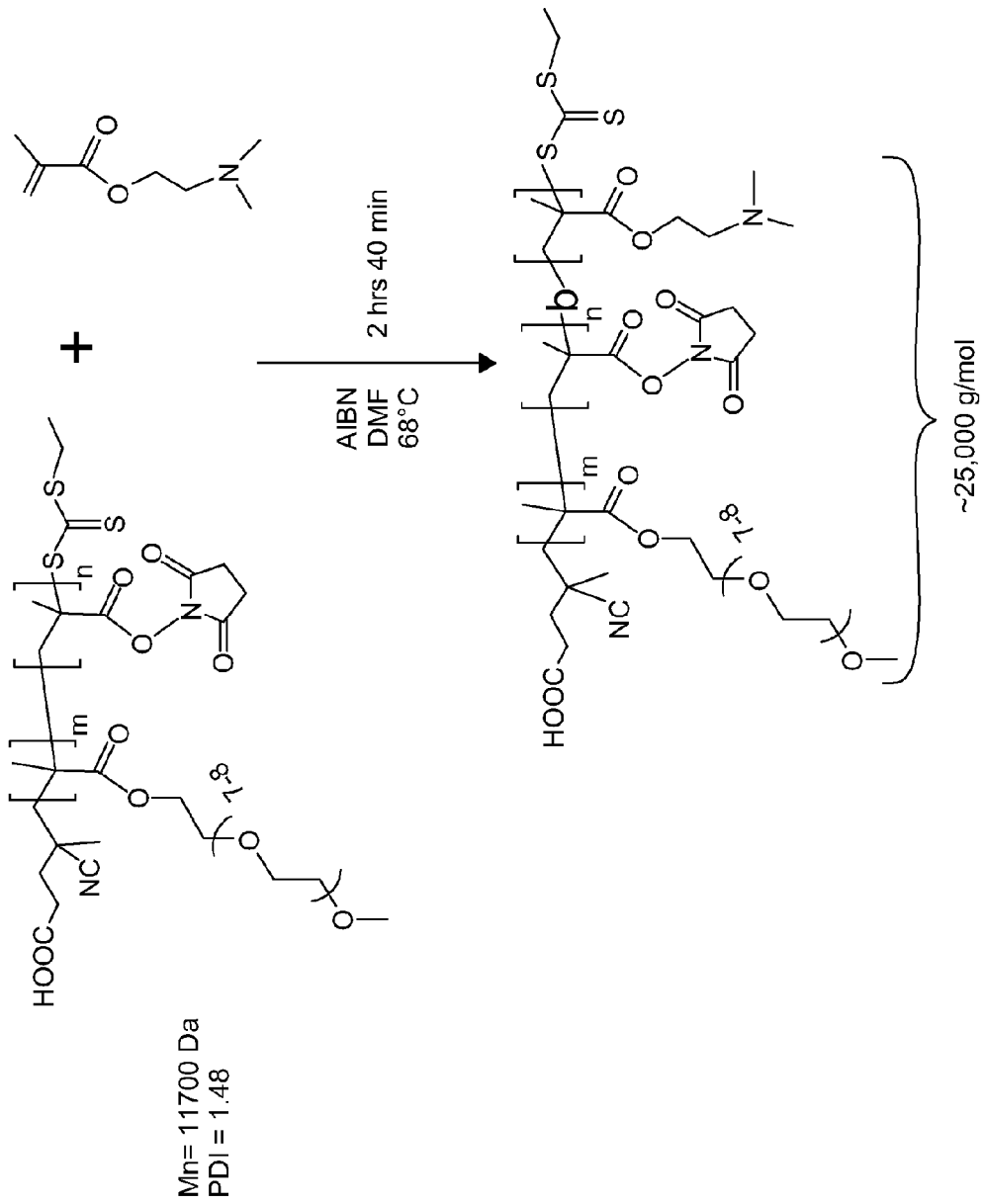
FIG. 1 illustrates the synthesis of poly[PEGMA-MAA(NHS)]-b-[DMAEMA].

When introducing elements of the present invention or the preferred embodiment(s) thereof, the articles "a," "an," "the" and "said" are intended to mean that there are one or more of the elements. The terms "comprising", "including" and "having" are intended to be inclusive and mean that there may be additional elements other than the listed elements.

Aliphatic: unless otherwise indicated, "aliphatic" or "aliphatic group" means an optionally substituted, non-aromatic hydrocarbon moiety. The moiety may be, for example, linear, branched, or cyclic (e.g., mono- or polycyclic such as fused, bridging, or spiro-fused polycyclic), or a combination thereof. Unless otherwise specified, aliphatic groups contain 1-20 carbon atoms.

Alkyl: unless otherwise indicated, the alkyl groups described herein are preferably lower alkyl containing from one to eight carbon atoms in the principal chain and up to 20 carbon atoms. They may be linear, branched or cyclic and include methyl, ethyl, propyl, butyl, hexyl and the like.

Amino: unless otherwise indicated, the term "amino" as used herein alone or as part of another group denotes the moiety —$NR_1R_2$ wherein $R_1$ and $R_2$ are hydrogen, hydrocarbyl, substituted hydrocarbyl or heterocyclo.

Amide or Amido: unless otherwise indicated, the "amide" or "amido" moieties represent a group of the formula —$CONR_1R_2$ wherein $R_1$ and $R_2$ are as defined in connection with the term "amino. "Substituted amide," for example, refers to a group of formula —$CONR_1R_2$ wherein at least one of $R_1$ and $R_2$ are other than hydrogen. "Unsubstituted amido," for example, refers to a group of formula —$CONR_1R_2$, wherein $R_1$ and $R_2$ are both hydrogen.

Anionic Monomer, Anionic Monomeric Unit or Anionic Repeat Unit: unless otherwise indicated, an "anionic monomer," "anionic monomeric unit" or "anionic repeat unit" is a monomer or monomeric unit bearing a group that is present in an anionic charged state or in a non-charged state, but in the non-charged state is capable of becoming anionic charged, e.g., upon removal of an electrophile (e.g., a proton ($H^+$), for example in a pH dependent manner). In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, phosphates, and sulfonamides.

Anionic species: unless otherwise indicated, an "Anionic species" is a group, residue or molecule that is present in an anionic charged or non-charged state, but in the non charged state is capable of becoming anionic charged, e.g., upon removal of an electrophile (e.g., a proton ($H^+$), for example in a pH dependent manner). In certain instances, the group, residue or molecule is substantially negatively charged at an approximately physiological pH but undergoes protonation and becomes substantially neutral at a weakly acidic pH.

Aryl: unless otherwise indicated, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

Attached: unless otherwise indicated, two moieties or compounds are "attached" if they are held together by any interaction including, by way of example, one or more covalent bonds, one or more non-covalent interactions (e.g., ionic bonds, static forces, van der Waals interactions, combinations thereof, or the like), or a combination thereof.

Block Copolymer: unless otherwise indicated, a "block copolymer" comprises two or more homopolymer or copolymer subunits linked by covalent bonds. Block copolymers with two or three distinct blocks are called diblock copolymers and triblock copolymers, respectively. A schematic generalization of a diblock copolymer is represented by the formula $[A_aB_bC_c \ldots ]_m\text{-}[X_xY_yZ_z \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: x-x-y-z-x-y-y-z-y-z-z-z . . . . A non-limiting, exemplary alternating random configuration may have the non-limiting form: x-y-x-z-y-x-y-z-y-x-z . . . , and an exemplary regular alternating configuration may have the non-limiting form: x-y-z-x-y-z-x-y-z . . . . An exemplary regular block configuration may have the following non-limiting configuration: . . . x-x-x-y-y-y-z-z-z-x-x-x . . . , while an exemplary random block configuration may have the non-limiting configuration: . . . x-x-x-z-z-x-x-y-y-y-y-z-z-z-x-x-z-z-z- . . . . In a gradient polymer, the content of one or more monomeric units increases or decreases in a gradient manner from the α-end of the polymer to the w-end. In none of the preceding generic examples is the particular juxtaposition of individual constitutional units or blocks or the number of constitutional units in a block or the number of blocks meant nor should they be construed as in any manner bearing on or limiting the actual structure of block copolymers forming a micelle described herein. As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

Cationic Monomer, Cationic Monomeric Unit or Cationic Repeat Unit: unless otherwise indicated, an "cationic monomer," "cationic monomeric unit" or "cationic repeat unit" is a monomer or a monomeric or repeat unit (the terms "monomeric unit" and "repeat unit" being used interchangeably) bearing a cation or a moiety capable of having a cationic charge upon addition of an electrophile (e.g., a proton (H+)).

Chargeable species, Chargeable Group, or Chargeable Monomeric Unit: unless otherwise indicated, a "chargeable species," "chargeable group" or "chargeable monomeric unit" is a species, group or monomeric unit in either a charged or non-charged state. In certain instances, a "chargeable monomeric unit" is one that can be converted to a charged state (either an anionic or cationic charged state) by the addition or removal of an electrophile (e.g., a proton ($H^+$), for example in a pH dependent manner). The use of any of the terms "chargeable species", "chargeable group", or "chargeable monomeric unit" includes the disclosure of any other of a "chargeable species", "chargeable group", or "chargeable monomeric unit" unless otherwise stated. A "chargeable species" that is "charged or chargeable to an anion" or "charged or chargeable to an anionic species" is a species or group that is either in an anionic charged state or non-charged state, but in the non-charged state is capable of being converted to an anionic charged state, e.g., by the removal of an electrophile, such as a proton ($H^+$). A "chargeable species" that is "charged or chargeable to a cation" or "charged or chargeable to a cationic species" is a species or group that is either in an cationic charged state or non-charged state, but in the non-charged state is capable of being converted to a cationic charged state, e.g., by the addition of an electrophile, such as a proton ($H^+$). "Chargeable monomeric units" described herein are used interchangeably with "chargeable monomeric residues".

Copolymer: unless otherwise indicated, the term "copolymer" signifies that the polymer is the result of polymerization of two or more different monomers.

Critical Micelle Concentration and CMC: unless otherwise indicated, the "critical micelle concentration" or "CMC" is the concentration at which a micelle self-assembles.

Dicer Substrate: unless otherwise indicated, a "dicer substrate" is a substrate for the RNase III family member Dicer in cells, the substrate possessing at least about 25 base pair duplex RNA. Dicer substrates are cleaved to produce approximately 21 base pair duplex small interfering RNAs (siRNAs) that evoke an RNA interference effect resulting in gene silencing by mRNA knockdown.

Disrupted: unless otherwise indicated, a micelle is "disrupted" if it does not function in an identical, substantially similar or similar manner and/or possess identical, substantially similar or similar physical and/or chemical characteristics as would a stable micelle. In "disruption" of a micelle can be determined in any suitable manner. In one instance, a micelle is "disrupted" if it does not have a hydrodynamic particle size that is less than 5 times, 4 times, 3 times, 2 times, 1.8 times, 1.6 times, 1.5 times, 1.4 times, 1.3 times, 1.2 times, or 1.1 times the hydrodynamic particle size of a micelle comprising the same block copolymers and as formed in an aqueous solution at a pH of 7.4, or formed in human serum. In one instance, a micelle is "disrupted" if it does not have a concentration of assembly that is less than 5 times, 4 times, 3 times, 2 times, 1.8 times, 1.6 times, 1.5 times, 1.4 times, 1.3 times, 1.2 times, or 1.1 times the concentration of assembly of a micelle comprising the same block copolymers and as formed in an aqueous solution at a pH of 7.4, or formed in human serum.

Endosome Disruptive & Endosomolytic: unless otherwise indicated, a composition is "endosome disruptive," also sometimes referred to as "endosomolytic," if the effect of the composition upon the endosome is to increase the permeability of the endosomal membrane.

Heteroalkyl: unless otherwise indicated, the term "heteroalkyl" means an alkyl group wherein at least one of the backbone carbon atoms is replaced with a heteroatom.

Heteroaryl: unless otherwise indicated, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heteroatom: unless otherwise indicated, the term "heteroatom" means an atom other than hydrogen or carbon, such as an oxygen, sulfur, nitrogen, phosphorus, boron, arsenic, selenium or silicon atom.

Heterocyclo: unless otherwise indicated, the terms "heterocyclo" and "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

Heterohydrocarbyl: unless otherwise indicated, the term "heterohydrocarbyl" means a hydrocarbyl group wherein at least one of the chain carbon atoms is replaced with a heteroatom.

Hydrocarbon or Hydrocarbyl: unless otherwise indicated, the terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms Hydrophobic: unless otherwise indicated, the terms "hydrophobic" and "hydrophobicity" are terms of art describing a physical property of a composition measured by the free energy of transfer of the composition between a non-polar solvent and water (Hydrophobicity regained. Karplus P. A., *Protein Sci.*, 1997, 6: 1302-1307.). The hydrophobicity of a composition can be measured by its log P value, the logarithm of a partition coefficient (P), which is defined as the ratio of concentrations of a compound in the two phases of a mixture of two immiscible solvents, e.g., octanol and water. Experimental methods of determination of hydrophobicity as well as methods of computer-assisted calculation of log P values are known to those skilled in the art. Hydrophobic species of the present invention include but are not limited to aliphatic, heteroaliphatic, aryl, and heteroaryl groups.

Hydrophobic Core: unless otherwise indicated, a "hydrophobic core" comprises hydrophobic moieties. In certain instances, a "hydrophobic core" is substantially non-charged (e.g., the charge is substantially net neutral).

Hydrophobic Repeat Unit: unless otherwise indicated, a "hydrophobic repeat unit" or a "hydrophobic monomeric unit" is a repeat unit or monomeric unit of a polymer possessing a hydrophobic substituent.

Hydrophobic Species: unless otherwise indicated, the terms "hydrophobic species" and "hydrophobic-enhancing moiety" is a moiety such as a substituent, residue or a group which, when covalently attached to a molecule, such as a monomer or a polymer, increases the molecule's hydrophobicity.

Inhibition, Silencing, Attenuation or Knock-Down: unless otherwise indicated, the terms "inhibition," "silencing," and "attenuation" as used herein refer to a measurable reduction in expression of a target mRNA or the corresponding protein as compared with the expression of the target mRNA or the corresponding protein in the absence of a knockdown agent. "Knockdown," or the reduction in expression of the target mRNA or the corresponding protein, can be assessed by measuring the mRNA levels using techniques well known in the art such as quantitative polymerase chain reaction (qPCR) amplification, RNA solution hybridization, nuclease protection, northern blotting and hybridization, and gene expression monitoring with a microarray; and in the case of proteins by techniques well known in the art such as SDS-PAGE, antibody binding, western blot analysis, immunoprecipitation, radioimmunoassay or enzyme-linked immunosorbent assay (ELISA), fluorescence activated cell analysis and immunocytochemistry.

Inhibit gene expression: unless otherwise indicated, the phrase "inhibit gene expression" means to cause any measurable reduction in the amount of an expression product of the gene. The expression product can be an RNA transcribed from the gene (e.g., an mRNA) and/or a polypeptide translated from an mRNA transcribed from the gene. The level of expression may be determined using standard techniques for measuring mRNA or protein.

Membrane Destabilizing Polymer or Membrane Destabilizing Block: unless otherwise indicated, a "membrane destabilizing polymer" or a "membrane destabilizing block" can directly or indirectly elicit a change (e.g., a permeability change) in a cellular membrane structure (e.g., an endosomal membrane) so as to permit an agent (e.g., polynucleotide), in association with or independent of a micelle (or a constituent polymer thereof), to pass through such membrane structure, for example, to enter a cell or to exit a cellular vesicle (e.g., an endosome). A membrane destabilizing polymer can be (but is not necessarily) a membrane disruptive polymer. A membrane disruptive polymer can directly or indirectly elicit lysis of a cellular vesicle or otherwise disrupt a cellular membrane (e.g., as observed for a substantial fraction of a population of cellular membranes). Generally, membrane destabilizing or membrane disruptive properties of polymers or micelles can be assessed by various means. In one non-limiting approach, a change in a cellular membrane structure can be observed by assessment in assays that measure (directly or indirectly) release of an agent (e.g., polynucleotide) from cellular membranes (e.g., endosomal membranes), for example, by determining the presence or absence of such agent, or an activity of such agent, in an environment external to such membrane. Another non-limiting approach involves measuring red blood cell lysis (hemolysis), e.g., as a surrogate assay for a cellular membrane of interest. Such assays may be done at a single pH value or over a range of pH values.

Micelle: unless otherwise indicated, a "micelle" is a particle comprising a core and a hydrophilic shell, wherein the core is held together at least partially, predominantly or substantially through hydrophobic interactions. The micelle may be, for example, a multi-component, nanoparticle comprising at least two domains, the inner domain or core, and the outer domain or shell. Micelle particles described herein may have any suitable or desired diameter, e.g., of less than 1000 nanometers (nm). In general, the micelle should have dimensions small enough to allow their uptake by eukaryotic cells. Typically, the micelle has a longest lateral dimension, also known as the diameter, of 200 nm or less. In some embodiments, the micelle has a diameter of 100 nm or less. Smaller micelles, e.g. having diameters of about 10 nm to about 200 nm, about 20 nm to about 100 nm, or 50 nm or less, e.g., 5 nm-30 nm, are used in some embodiments. Micelle particle size can be determined in any manner, including, but not limited to, by gel permeation chromatography (GPC), dynamic light scattering (DLS), electron microscopy techniques (e.g., TEM), and other methods.

Non-Charged Repeat Units: unless otherwise indicated, a "non-charged repeat unit" is a repeat unit that is neither an anionic repeat unit or a cationic repeat unit.

Nucleoside: unless otherwise indicated, the term "nucleoside" is used to describe a composition comprising a monosaccharide and a base. The monosaccharide includes but is not limited to pentose and hexose monosaccharides. The monosaccharide also includes monosaccharide mimetics and monosaccharides modified by substituting hydroxyl groups with halogens, methoxy, hydrogen or amino groups, or by esterification of additional hydroxyl groups.

Nucleotide: unless otherwise indicated, the term "nucleotide," in its broadest sense, refers to any compound and/or substance that is or can be incorporated into a polynucleotide (e.g., oligonucleotide) chain. In some embodiments, a nucleotide is a compound and/or substance that is or can be incorporated into a polynucleotide (e.g., oligonucleotide) chain via a phosphodiester linkage. In some embodiments, "nucleotide" refers to individual nucleic acid residues (e.g. nucleotides and/or nucleosides). In certain embodiments, "at least one nucleotide" refers to one or more nucleotides present; in various embodiments, the one or more nucleotides are discrete nucleotides, are non-covalently attached to one another, or are covalently attached to one another. As such, in certain instances, "at least one nucleotide" refers to one or more polynucleotide (e.g., oligonucleotide). In some embodiments, a polynucleotide is a polymer comprising two or more nucleotide monomeric units.

Oligonucleotide: unless otherwise indicated, the term "oligonucleotide" refers to a polymer comprising 7-200 nucleotide monomeric units. In some embodiments, "oligonucleotide" encompasses single and or/double stranded RNA as well as single and/or double-stranded DNA. Furthermore, the terms "nucleotide", "nucleic acid," "DNA," "RNA," and/or similar terms include nucleic acid analogs, i.e., analogs having a modified backbone, including but not limited to peptide nucleic acids (PNA), locked nucleic acids (LNA), phosphono-PNA, morpholino nucleic acids, or nucleic acids with modified phosphate groups (e.g., phosphorothioates, phosphonates, 5'-N-phosphoramidite linkages). Nucleotides can be purified from natural sources, produced using recombinant expression systems and optionally purified, chemically synthesized, etc. In some embodiments, a nucleotide is or comprises a natural nucleoside phosphate (e.g. adenosine, thymidine, guanosine, cytidine, uridine, deoxyadenosine, deoxythymidine, deoxyguanosine, and deoxycytidine phosphate). In some embodiments, the base includes any bases occurring naturally in various nucleic acids as well as other modifications which mimic or resemble such naturally occurring bases. Nonlimiting examples of modified or derivatized bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5 methyluracil, uracil-5-oxyacetic acid methylester, uracil-5-oxyacetic acid, 5-methyl-2-thiouracil, 3-(3-amino-3-N-2-carboxypropyl)uracil, 2-aminoadenine, pyrrolopyrimidine, and 2,6-diaminopurine. Nucleoside bases also include universal nucleobases such as difluorotolyl, nitroindolyl, nitropyrrolyl, or nitroimidazolyl. Nucleotides also include nucleotides which harbor a label or contain abasic, i.e., lacking a base, monomers. A nucleic acid sequence is presented in the 5' to 3' direction unless otherwise indicated. A nucleotide can bind to another nucleotide in a sequence-specific manner through hydrogen bonding via Watson-Crick base pairs. Such base pairs are said to be complementary to one another. An oligonucleotide can be single stranded, double-stranded or triple-stranded.

Oligonucleotide gene expression modulator: as used herein, an "oligonucleotide gene expression modulator" is an oligonucleotide agent capable of inducing a selective modulation of gene expression in a living cell by mechanisms including but not limited to an antisense mechanism or by way of an RNA interference (RNAi)-mediated pathway which may include (i) transcription inactivation; (ii) mRNA degradation or sequestration; (iii) transcriptional inhibition or attenuation or (iv) inhibition or attenuation of translation. Oligonucleotide gene expression modulators include, regulatory RNA (including virtually any regulatory RNA) such as, but not limited to, antisense oligonucleotides, miRNA, siRNA, RNAi, shRNA, aptamers and any analogs or precursors thereof.

Oligonucleotide Knockdown Agent: unless otherwise indicated, an "oligonucleotide knockdown agent" is an oligonucleotide species which can inhibit gene expression by targeting and binding an intracellular nucleic acid in a sequence-specific manner. Non-limiting examples of oligonucleotide knockdown agents include siRNA, miRNA, shRNA, dicer substrates, antisense oligonucleotides, decoy DNA or RNA, antigene oligonucleotides and any analogs and precursors thereof.

pH Dependent, Membrane-Destabilizing: unless otherwise indicated, a "pH dependent, membrane-destabilizing" group or block is a group or block that is at least partially, predominantly, or substantially hydrophobic and is membrane destabilizing in a pH dependent manner. In certain instances, a pH dependent membrane destabilizing polymer block is a hydrophobic polymeric segment of a block copolymer and/or comprises a plurality of hydrophobic species; and comprises a plurality of chargeable species. In some embodiments, the chargeable species is anionic. In some embodiments, the anionic chargeable species is anionic at about neutral pH. In further or alternative embodiments, the anionic chargeable species is non-charged at a lower, e.g., endosomal pH. In some embodiments, the membrane destabilizing chargeable hydrophobe comprises a plurality of cationic species. The pH dependent membrane-destabilizing chargeable hydrophobe comprises a non-peptidic and non-lipidic polymer backbone. For example, a pH dependent, membrane-destabilizing block may possess anionic repeat units the substituents of which are predominantly ionized (anions) at one pH, e.g., pH 7.4, and predominantly neutral at a lesser pH, e.g., pH 5.0 whereby the pH dependent, membrane-destabilizing group or block becomes increasingly hydrophobic as a function of the drop in pH from 7.4 to 5.0.

RNAi agent: unless otherwise indicated, the term "RNAi agent" refers to an oligonucleotide which can mediate inhibition of gene expression through an RNAi mechanism and includes, but is not limited to, siRNA, microRNA (miRNA), short hairpin RNA (shRNA), asymmetrical interfering RNA (aiRNA), dicer substrate and the precursors thereof.

RNA interference (RNAi): unless otherwise indicated, the term "RNA interference" or "RNAi" refers to sequence-specific inhibition of gene expression and/or reduction in target mRNA and protein levels mediated by an at least partially double-stranded RNA, which also comprises a portion that is substantially complementary to a target RNA.

Short hairpin RNA (shRNA): unless otherwise indicated, "short hairpin RNA" or "shRNA" refers to an oligonucleotide having at least two complementary portions hybridized or capable of hybridizing with each other to form a double-stranded (duplex) structure and at least one single-stranded portion.

Short interfering RNA (siRNA): unless otherwise indicated, "short interfering RNA" or "siRNA" refers to an RNAi agent that is approximately 15-50 base pairs in length and optionally further comprises zero to two single-stranded overhangs. One strand of the siRNA includes a portion that hybridizes with a target RNA in a complementary manner. In some embodiments, one or more mismatches between the siRNA and the targeted portion of the target RNA may exist. In some embodiments, siRNAs mediate inhibition of gene expression by causing degradation of target transcripts.

Stable: unless otherwise indicated, a micelle described herein is "stable" if the assembly does not disassociate or become destabilized. In certain instances, a stable micellic assembly is one that has a hydrodynamic particle size that is within approximately 60%, 50%, 40%, 30%, 20%, or 10% of the hydrodynamic particle size of a micellic assembly comprising the same block copolymers initially formed in an aqueous solution at a pH of 7.4 (e.g., a phosphate-buffered saline, pH 7.4). In some instances, a stable micellic assembly is one that has a concentration of formation/assembly that is within about 60%, 50%, 40%, 30%, 20%, or 10% of the concentration of formation/assembly of a micellic assembly comprising the same block copolymers initially in an aqueous solution at a pH of 7.4 (e.g., a phosphate-buffered saline, pH 7.4).

Substantially Non-Charged Block: unless otherwise indicated, the term "substantially non-charged block" means a polymeric block that has a neutral charge, or a near neutral charge. For example, less than about 10 mole % of the repeat units in a block will be anionic, cationic or zwitterionic repeat units in a substantially non-charged block. By way of further example, less than about 5 mole % of the repeat units in a block will be anionic, cationic or zwitterionic repeat units in a substantially non-charged block.

Substituted or Optionally Substituted: unless otherwise indicated, the term "substituted" and "optionally substituted" means that the referenced group is or may be substituted with one or more additional suitable group(s), which may be individually and independently selected from acetals, acyl, acyloxy, alkenoxy, alkoxy, alkylthio, alkynoxy, amido, amino, aryl, aryloxy, arylthio, carbonyl, carboxamido, carboxyl, cyano, esters, ethers, hydrocarbyl, substituted hydrocarbyl, heterohydrocarbyl, substituted heterohydroalkyl, cycloalkyl, halogen, heteroalicyclic, heteroaryl, hydroxy, isocyanato, isothiocyanato, ketals, keto, mercapto, nitro, perhaloalkyl, silyl, sulfonamido, sulfonyl, thiocarbonyl, thiocyanato, thiol, and/or the protected derivatives thereof.

Therapeutic agent: unless otherwise indicated, the phrase "therapeutic agent" refers to any agent that, when administered to a subject, organ, tissue, or cell has a therapeutic effect and/or elicits a desired biological and/or pharmacological effect.

Therapeutically effective amount: unless otherwise indicated, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Zwitterionic Monomer, Zwitterionic Monomeric Unit or Zwitterionic Repeat Unit: unless otherwise indicated, a "zwitterionic monomer," "zwitterionic monomeric unit" or "zwitterionic repeat unit" is a monomer or a monomeric or repeat unit (the terms "monomeric unit" and "repeat unit" being used interchangeably) bearing (i) a cation or a moiety capable of having a cationic charge upon addition of an electrophile (e.g., a proton ($H^+$)) and (ii) an anion or a moiety capable of having an anionic charge upon removal of an electrophile (e.g., a proton ($H^+$)).

DETAILED DESCRIPTION OF THE PREFERRED EMBODIMENTS

One aspect of the present invention is a copolymer comprising three discrete polymeric blocks, each possessing somewhat different characteristics or providing a somewhat different function. One of these blocks is a hydrophilic polymeric block, sometimes referred to herein as the "first block," the "shielding block," the "hydrophilic shielding block" or simply the "hydrophilic block." As described in greater detail elsewhere herein, the first block may be used to contribute water solubility to the copolymer, to aid in micelle formation, to target the copolymer to a cellular or other biological target, to shield a therapeutic agent that is associated with the copolymer, or a combination of two or more thereof. The second of these blocks, sometimes referred to herein as the "second block" or the "carrier block;" is attached to a therapeutic agent, or at least possesses a functional group for attaching a therapeutic agent to the copolymer. The third of these blocks is a hydrophobic polymeric block, sometimes referred to herein as the third block or simply the "hydrophobic block." As described in greater detail elsewhere herein, the third block may be used to decrease the water solubility of the copolymer, to aid in micelle formation, to destabilize a cellular membrane or other biological target, or a combination of two or more thereof. The copolymer may optionally possess additional polymeric blocks that amplify the function of the first, second and third blocks of the copolymers of the present invention, or which introduce other functionalities or properties to the copolymer. Regardless of the number of blocks, it is generally preferred that the carrier block be located between the first (hydrophilic) and third (hydrophobic) blocks. In addition, the number average molecular weight of the first, second and third blocks, in combination is about 5,000 to about 100,000 daltons. Additionally, in one embodiment, the Zeta potential of a polymeric solution containing a block copolymer of the present invention (without an associated therapeutic agent such as a polynucleotide) is between ±6 mV (millivolt). In one preferred embodiment, the Zeta potential of the polymeric solution (without an associated therapeutic agent such as a polynucleotide) is between ±5 mV. In one preferred embodiment, the Zeta potential of the polymeric solution (without an associated therapeutic agent such as a polynucleotide) is between ±2 mV.

In general, the properties of the first, second and third blocks may be tuned by selection of the monomeric residues constituting each of the three blocks or the relative mole fractions. For example, the first block is hydrophilic and the third block is hydrophobic and this difference in hydrophilicity may be achieved by the polymerization of different sets of monomers for the first and third blocks; alternatively, the same set of monomers may be used for the two blocks, but the first block will contain a relatively greater percentage of hydrophilic monomeric residues to provide the first block with an overall hydrophilic character whereas the third block will contain a relatively greater percentage of hydrophobic monomeric residues to provide the hydrophobic block with an overall hydrophobic character. Similarly, the second block is attached to the therapeutic agent or at least possesses a functional group for attaching a therapeutic. Relative to the first and third blocks, therefore, the carrier block will comprise the residues of a different set of monomers relative to the first and third blocks, or at least a different percentage of monomeric residues that are used to attach the therapeutic agent to the carrier block. The first, second, and third blocks thus possess somewhat different properties or function relative to each other as a result of the compositional differences between the respective blocks.

Although the carrier block is located between the hydrophilic block and the hydrophobic block, it is not necessarily immediately adjacent to each. Stated differently, the carrier block may be covalently coupled to the hydrophilic block via a polymeric or non-polymeric linking moiety. Alternatively, or additionally, the carrier block may be covalently coupled to the hydrophobic block via a polymeric or non-polymeric linking moiety. For example, the carrier block may be coupled to the hydrophilic block and/or the hydrophobic block by a series of amino acid residues, saccharide residues, nucleic acid residues, etc., to introduce a cleavage point or other functionality between the respective blocks. By way of further example, the carrier block may be covalently coupled to the hydrophilic block and/or the hydrophobic block by a cleavable moiety such as a disulfide, a hydrazide, an ester, an acetal, or a phosphodiester linking moiety. In general, it is presently preferred that the carrier block be immediately adjacent to the hydrophilic block. It is also presently preferred that the carrier block be immediately adjacent to the hydrophobic block.

Provided in certain embodiments herein, a block copolymer described herein, or a micelle comprising a plurality of such block copolymers, comprises a hydrophilic shielding block, a carrier block and a hydrophobic block. In specific embodiments, the carrier block is between the hydrophilic shielding block and the hydrophobic block.

Provided in certain embodiments are block copolymers comprising at least three blocks and micelles thereof. In more specific embodiments, block copolymers comprise at least three blocks. In some embodiments, polymers described herein comprise at least one hydrophobic block and at least two hydrophilic blocks. In certain embodiments, polymers described herein comprise at least one hydrophobic block, at least one hydrophilic block, and at least one block associated with a therapeutic agent (e.g., polynucleotide or peptide), the block associated with a therapeutic agent being between the hydrophilic and hydrophobic blocks.

In some embodiments, at least one of the hydrophilic blocks comprises a plurality of charged species (i.e., is polycationic, polyanionic, or both), and/or is associated with a molecule that comprises a plurality of charged species (e.g., a polynucleotide or polypeptide). In specific embodiments, at least one of the hydrophilic blocks comprises a plurality of species that are charged at about neutral pH (i.e., is polycationic, polyanionic, or both at about neutral pH). In certain embodiments, at least one of the hydrophilic blocks is a shielding block. In specific embodiments, the shielding block is non-charged, e.g., at about neutral pH.

It is generally preferred that one or more of the polymer blocks is a copolymer block and that the copolymer block is a random copolymer block. Thus, for example, it is generally preferred that at least one of the first, second or third blocks be a random copolymer comprising two or more compositionally distinct monomeric residues. In one such example, the first block (i.e., the hydrophilic block) is a random copolymer block comprising two or more compositionally distinct monomeric residues. Additionally, or alternatively, the second block (i.e., the carrier block) may be a random copolymer comprising two or more compositionally distinct monomeric residues. Additionally, or alternatively, the third block (i.e., the hydrophobic block) may be a random copolymer comprising two or more compositionally distinct monomeric residues. In some embodiments, the first or second block of the polymers described herein are homopolymer blocks. For example, in one embodiment, the first block is a homopolymer and the second and third blocks are random copolymers. By way of further example, in one embodiment, the first and second blocks are compositionally distinct homopolymers and the third block is a random copolymer. By way of further example, in one embodiment, the three blocks are compositionally distinct homopolymers. By way of yet further example, in one embodiment, the three blocks are compositionally distinct random copolymers.

The first, second and third blocks comprise chain atoms and pendant groups covalently coupled to the chain atoms. Preferably, the chain atoms are carbon or a combination of (i) carbon and (ii) sulfur and/or oxygen atoms. Thus, for example, the repeat units of the first, second and third blocks are independently selected from the group consisting of substituted alkylene, substituted alkylene glycol, and substituted alkylene thioglycol repeat units, and combinations thereof. In one preferred embodiment, the chain atoms of the first, second and third blocks are carbon. In another embodiment, the chain atoms of the first and second blocks are independently carbon or a combination of carbon, oxygen and sulfur atoms, and the chain atoms of the third block are carbon. In another embodiment, the chain atoms of the first and second blocks are independently carbon or a combination of carbon and oxygen atoms, and the chain atoms of the third block are carbon. In another embodiment, the chain atoms of the first and second blocks are independently carbon or a combination of carbon and sulfur atoms, and the chain atoms of the third block are carbon. In another embodiment, the chain atoms of the first block are a combination of carbon and oxygen atoms, and the chain atoms of the second and third blocks are carbon. Independent of the selection of the chain atoms, the pendant groups are preferably selected from the group consisting of hydrogen, hydrocarbyl, substituted hydrocarbyl, substituted carbonyl and heterocyclo.

In a preferred embodiment, the block copolymers of the present invention is prepared by a method other than by stepwise coupling approaches involving a sequence of multiple individual reactions (e.g., such as known in the art for peptide synthesis or for oligonucleotide synthesis). For example, in one embodiment, at least one of the first, second and third blocks is formed by chain-growth polymerization, sometimes referred to as addition polymerization. By way of further example, in one embodiment, at least two of the first, second and third blocks is formed by chain-growth polymerization. By way of further example, in one embodiment, each of the first, second and third blocks is formed by chain-growth polymerization. As such, the first, second and third blocks are non-lipidic.

Although each of the blocks may contain repeat units linked by amide bonds, formed for example, by the condensation reaction of amino acids or by the condensation reaction of species other than amino acids (e.g., diamines and dicarboxylic acids), it is generally preferred that the substantial majority of the residues constituting the first, second and third blocks not be peptidic. Stated differently, it is generally preferred that the substantial majority of the residues of the first, second and third blocks are other than amino acid residues linked by peptide bonds. For example, in one embodiment at least 90% of the residues constituting the first block are other than amino acid residues linked by peptide bonds. By way of further example, in one embodiment at least 90% of the residues constituting the second block are other than amino acid residues linked by peptide bonds. By way of further example, in one embodiment at least 90% of the residues constituting the third block are other than amino acid residues linked by peptide bonds. By way of further example, in one embodiment it is preferred that at least 90% of the residues constituting the first, second, and third blocks, considered collectively, be other than amino acid residues linked by peptide bonds. By way of yet further example, in one embodiment it is preferred that at least 90% of the residues constituting each of the first, second, and third blocks be other than amino acid residues linked by peptide bonds. Preferably, each block is a substantially non peptidic polymer (consists of a polymer other than an amino acid polymer).

In contrast, for clarity, notwithstanding and without prejudice to the foregoing, the targeting moieties and/or other biomolecular agents of the inventions can be an amino acid polymer (e.g., a peptide) or a nucleic acid polymer (e.g., an oligonucleotide) or a polysaccharide. In one preferred embodiment, peptides, saccharides, or nucleic acid residues are attached, as pendant groups, to the repeat units to increase water solubility, provide shielding, targeting, or as a therapeutic agents. or other hydrophilic or targeting groups are attached, as pendant groups to the repeat units. When attached as pendant groups, however, the peptides, saccharides, and nucleic acids do not provide peptide, glycosidic or phosphodiester bonds along the backbone of the polymer block which they would do if incorporated as repeat units.

Conveniently, the first, second and third blocks may be prepared from readily polymerizable monomers. For example, in one embodiment, the repeat units are residues of ethylenically unsaturated monomer(s). In another, the first, second and third blocks comprise repeat units independently derived from optionally substituted acrylic acid monomers, optionally substituted vinyl aryl monomers, optionally substituted acrylamide monomers, optionally substituted acrylate monomers and combinations thereof.

In one preferred embodiment, the first block, the second block or the third block comprises repeat units of Formula 1

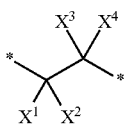

Formula 1 wherein * designates the point of attachment of the repeat unit of Formula 1 to other repeat units; each $X^1$ and $X^2$ is independently selected from the group consisting of hydrogen, hydrocarbyl, substituted hydrocarbyl, heterocyclo, and substituted carbonyl, provided, however, $X^1$ and $X^2$ are not, in the same repeat unit, selected from the group consisting of aryl, heteroaryl, heterosubstituted carbonyl, and combinations thereof; each $X^3$ is independently hydrogen, alkyl or substituted alkyl, and each $X^4$ is independently heterosubstituted carbonyl, aryl, or heteroaryl. For example, in one such embodiment, the first, second or third blocks comprise repeat units corresponding to Formula 1 in which $X^4$ is aryl or heteroaryl. In another such embodiment, the first, second or third blocks comprise repeat units corresponding to Formula 1 in which $X^4$ is —C(O)O$X^{40}$, —C(O)S$X^{40}$, or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In another such embodiment, two of the first, second and third blocks comprise repeat units corresponding to Formula 1 in which $X^4$ is —C(O)O$X^{40}$, —C(O)S$X^{40}$, or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In another such embodiment, the first, second and third blocks comprise repeat units corresponding to Formula 1 in which $X^4$ is —C(O)O$X^{40}$, —C(O)S$X^{40}$, or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In another such embodiment, the first, second or third blocks comprise repeat units corresponding to Formula 1 in which $X^4$ is —C(O)O$X^{40}$ or —C(O)N$X^{40}X^{41}$ and $X^{40}$ and $X^{41}$ are independently hydrogen, hydrocarbyl, substituted hydrocarbyl, heterohydrocarbyl, substituted heterohydrocarbyl, or heterocyclo.

Hydrophilic Block

The first block of the copolymer of the present invention may be used to contribute a range of properties or functions to the copolymer. For example, the number and composition of the constituent units of the first block may be selected to impart the desired degree of water solubility/dispersability to the copolymer. Alternatively, or additionally, in those embodiments in which the polymers of the present invention are incorporated into micelles, the number and composition of the constituent units of the first block may be selected to provide micelles having a desired size, critical micelle concentration or other property. Independent of micelle formation, the number and composition of the constituent units of the first block may be selected to target the polymer to a cellular or other biological target. Alternatively, or additionally, the number and composition of the constituent units of the first block may be selected to shield a therapeutic agent that is associated with the copolymer.

Depending upon the desired properties and functionality, the first block may be a homopolymer block or a copolymer block. In those embodiments in which it is a copolymer block, it is preferably a random copolymer block. For example, the first block may be a copolymer block comprising two or more compositionally distinct monomeric residues. By way of further example, the first block may be copolymer block comprising charged repeat units (i.e., cationic repeat units, anionic repeat units, zwitterionic repeat units or a combination thereof), non-charged repeat units, or a combination thereof. In one specific embodiment, the first block comprises charged repeat units. In another specific embodiment, the first block comprises cationic repeat units. In yet another embodiment, the first block comprises cationic repeat units and non-charged repeat units. In yet another embodiment, the first block comprises zwitterionic repeat units and non-charged repeat units. In yet another embodiment, the first block comprises exclusively non-charged repeat units and the block is non-charged at neutral pH. Furthermore, in those embodiments in which the first block comprises cationic repeat units, the first block may comprise a combination of two or more compositionally distinct cationic repeat units; in those embodiments in which the first block comprises anionic repeat units, the first block may comprise a combination of two or more compositionally distinct anionic repeat units; in those embodiments in which the first block comprises zwitterionic repeat units, the first block may comprise a combination of two or more compositionally distinct zwitterionic repeat units; and in those embodiments in which the first block comprises non-charged repeat units, the first block may comprise a combination of two or more compositionally distinct non-charged repeat units.

In general, the hydrophilic first block may contain anionic repeat units, cationic repeat units, zwitterionic repeat units, a combination of two or more charged repeat units (e.g., anionic and cationic repeat units, anionic and zwitterionic repeat units, cationic and zwitterionic repeat units, or anionic, cationic and zwitterionic repeat units), substantially non-charged repeat units, or a combination thereof, provided that its overall character is hydrophilic. Stated differently, the hydrophilic first block may contain any of a wide range of repeat units, hydrophilic or even hydrophobic, provided that the sum of the contributions of the repeat units comprised by the first block provide a block having an overall hydrophilic character. When the repeat units contain ionizable groups, the contribution of an individual repeat unit to the overall hydrophilicity of the block of which it is a constituent may vary as a function of its pKa relative to the pH of the environment in which it is found. For example, propyl acrylic acid repeat units, —$CH_2C(CH_2CH_2CH_3)$(COOH)—, are predominantly ionized at pH 7 but not at pH 5 and thus, the hydrophobic contribution of propyl acrylic acid repeat units to a block is significantly greater at pH 5 than at pH 7. In general, therefore, when the first block comprises ionizable cationic repeat units or ionizable anionic repeat units, it is preferred that the sum of the contributions of the repeat units constituting the first block be such that the overall character of the block is hydrophilic at physiological pH. For example, in one embodiment, it is preferred that the first block be hydrophilic over the range of pH from pH 5.0 to pH 7.5.

In some embodiments, the hydrophilic first block is a substantially non-charged block. In specific embodiments, the hydrophilic first block is substantially non-charged and shields a charged second block and/or a charged therapeutic agent associated with a second block. For example, the first block may be a polysaccharide block. In some other embodiments, the hydrophilic first block is a polyzwitterionic (i.e., comprising a plurality of both cationic and anionic species or monomeric residues at about neutral pH) or polyanionic block (i.e., comprising a plurality of anionic monomeric residues at about neutral pH). In either of these embodiments, the hydrophilic first block may comprise at least one conjugatable or functionizable monomeric residue that may be used, for example, to link a targeting group, a water-solubilizing group, or other functional group to the polymer block, post-polymerization.

In one preferred embodiment, the hydrophilic first block is a hydrophilic polymer block suitable for (capable of/effective for) steric shielding of the polynucleotide. In this embodiment, the hydrophilic first block comprises a plurality of monomeric residues having a shielding species, and the shielding species is effective for steric shielding of a polynucleotide associated with the polymer or a micelle comprising the polymer. For example, the shielding species may be effective for enhancing the stability of the polynucleotide against enzymatic digestion in plasma. Additionally, or alternatively, the shielding species may be effective for reducing toxicity of a polymer or micelle described (e.g., by shielding a charged second hydrophilic block and reducing the effective surface charge of a polymer or micelle). Additionally, or alternatively, the shielding species is effective for maintaining desirable surface properties of a micelle comprising the polymer. Additionally, or alternatively, the shielding species may be effective for increasing the circulation time in or decreasing its clearance rate by the kidneys.

Depending upon the desired properties, the shielding species of a polymer or micelle may be selected from a range of moieties. For example, the shielding species may be an alcohol, a phenol, a thiol, a polyoxylated alkyl (e.g., polyethylene glycol, polypropylene glycol, or the like), an ether, a thio-ether, or the like. In some embodiments, the hydrophilic first block comprises a plurality of monomeric residues having a pendant group comprising a shielding oligomer (e.g., polyethylene glycol, polypropylene glycol, or the like). In specific embodiments, the shielding species of a polymer or micelle described herein is a polyoxylated alkyl with the structure of Formula II:

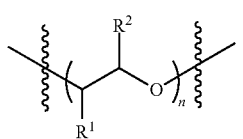

(II)

wherein each $R^1$ and $R^2$ are each independently selected from the group consisting of hydrogen, halogen, and optionally substituted $C_1$-$C_3$ alkyl, and n is an integer. In a preferred embodiment, the number of repeat units, n, will provide a shielding species having a molecular weight of about 40 to about 2000 daltons. In specific embodiments, n will be about 2-20; for example, n may be about 3-10 and, depending upon the polymer, about 4-5, about 8-9, or the like. In some embodiments, the shielding species corresponds to Formula II and has a molecular weight of about 40 to about 2000 dalton, or about 100 to about 2000 dalton.

In some embodiments, the hydrophilic first block has a structure corresponding to Formula Ia-1:

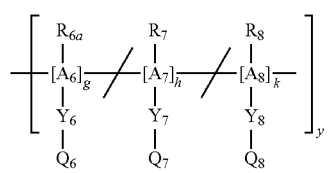

(Ia-1)

wherein:

each of $A_6$, $A_7$, and $A_8$ are independently selected from the group consisting of —C—C—, —C—, —C(O)(C)$_a$C(O)O—, —O(C)$_a$C(O)— and —O(C)$_b$O—;

a is 1-4;

b is 2-4;

each of $Y_6$, $Y_7$, and $Y_8$ are independently selected from the group consisting of a covalent bond, (1C-10C)alkyl-, (3C-6C)cycloalkyl, O-(1C-10C)alkyl, —C(O)O(2C-10C)alkyl-, —OC(O)(1C-10C) alkyl-, —O(2C-10C)alkyl-, —S(2C-10C)alkyl-, —C(O)NR$_6$(2C-100) alkyl-, and aryl, any of which is optionally substituted;

tetravalent carbon atoms of $A_6$-$A_8$ that are not fully substituted with $R_{6a}$, $R_7$, $R_8$ and $Y_6$-$Y_8$ are completed with an appropriate number of hydrogen atoms;

each $R_{6a}$, $R_7$, and $R_9$ is independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_6$ is a residue selected from the group consisting of residues which are hydrophilic at physiologic pH and are substantially non-charged at about neutral pH (e.g., hydroxy, polyoxylated alkyl, polyethylene glycol, polypropylene glycol, thiol, or the like);

$Q_7$ is a residue selected from the group consisting of residues which are hydrophilic at physiologic pH, and are at least partially positively charged at about neutral pH (e.g., amino, alkylamino, ammonium, alkylammonium, guanidine, imidazolyl, pyridyl, or the like); at least partially negatively charged at about neutral pH but undergo protonation at lower pH (e.g., carboxyl, sulfonamide, boronate, phosphonate, phosphate, or the like); at least partially zwitterionic at physiologic pH (e.g., a monomeric residue comprising a phosphate group and an ammonium group at physiologic pH), or hydrogen;

$Q_8$ is selected from a group consisting of a conjugatable or functionizable residue (e.g. residues that comprise a reactive group, e.g., azide, alkyne, succinimide ester, tetrafluorophenyl ester, pentafluorophenyl ester, p-nitrophenyl ester, pyridyl disulfide, aldehyde, ketone, amine, or the like) or a targeting agent (e.g., sugar residue, folate, peptide, or the like);

g is 0 to 1;

h is 0 to less than 1;

k is 0 to 1;

wherein g+h+k=1; and y is about 1 to about 100 kDa, or about 1 to about 30 kDa.

In some embodiments, the hydrophilic first block has a structure corresponding to Formula Ia-2:

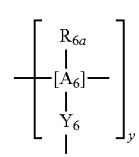

(Ia-2)

wherein:

$A_6$ is selected from the group consisting of —C—C—, —C—, —C(O)(C)$_a$C(O)O—, —O(C)$_a$C(O)— and —O(C)$_b$O—;

a is 1-4;

b is 2-4;

$R^4$ is selected from the group consisting of hydrogen, and optionally substituted $C_1$-$C_6$ alkyl, $Y_6$ is selected from the group consisting of a covalent bond, (1C-10C)alkyl-, (3C-6C)cycloalkyl, O-(1C-10C) alkyl-, —C(O)O(2C-100) alkyl-, —OC(O)(1C-10C) alkyl-, —O(20-10C)alkyl-, —S(2C-10C)alkyl-, —C(O)NR$_6$(2C-10C) alkyl-, and aryl, any of which is optionally substituted;

tetravalent carbon atoms of $A_6$ that are not fully substituted with $R_{6a}$ and $Y_6$ is completed with an appropriate number of hydrogen atoms;

each $R_{6a}$ is independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_6$ is a residue selected from the group consisting of residues which are hydrophilic at physiologic pH and are substantially non-charged at physiologic pH (e.g., hydroxy, polyoxylated alkyl, polyethylene glycol, polypropylene glycol, thiol, or the like); and y is about 1 to about 30 kDa.

In some embodiments, the hydrophilic first block is a copolymer comprising monomeric residues corresponding to Formula Ia, and other monomeric residues. In preferred embodiments, the other monomeric residues are non-charged. In some embodiments, the other monomeric residues are non-hydrophobic. In certain embodiments, the other monomeric residues do not significantly affect the overall hydrophilicity of the hydrophilic first block.

In one preferred embodiment, the hydrophilic block comprises repeat units corresponding to Formula 1

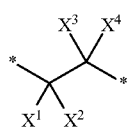

Formula 1 wherein * designates the point of attachment of the repeat unit of Formula 1 to other repeat units; each $X^1$ and $X^2$ is independently selected from the group consisting of hydrogen, hydrocarbyl, substituted hydrocarbyl, heterocyclo, and substituted carbonyl, provided, however, $X^1$ and $X^2$ are not, in the same repeat unit, selected from the group consisting of aryl, heteroaryl, heterosubstituted carbonyl, and combinations thereof; each $X^3$ is independently hydrogen, alkyl or substituted alkyl, and each $X^4$ is independently heterosubstituted carbonyl, aryl, or heteroaryl. For example, in one such embodiment, the hydrophilic block comprises repeat units corresponding to Formula 1 and $X^1$ and $X^2$ are each hydrogen. In another such example, the hydrophilic block comprises repeat units corresponding to Formula 1, $X^1$ and $X^2$ are each hydrogen and $X^3$ is hydrogen or alkyl. In a further example, the hydrophilic block comprises repeat units corresponding to Formula 1, $X^1$ and $X^2$ are each hydrogen, $X^3$ is hydrogen or alkyl, and each $X^4$ is independently heterosubstituted carbonyl. In a further example, the hydrophilic block comprises repeat units corresponding to Formula 1, $X^4$ is —C(O)O$X^{40}$, —C(O)S$X^{40}$, or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In a further example, the hydrophilic block comprises repeat units corresponding to Formula 1, $X^4$ is —C(O)O$X^{40}$ or —C(O)N$X^{40}X^{41}$, and $X^{40}$ and $X^{41}$ are independently hydrogen, hydrocarbyl, substituted hydrocarbyl, heterohydrocarbyl, substituted heterohydrocarbyl, or heterocyclo. In a further example, the hydrophilic block comprises repeat units corresponding to Formula 1, $X^1$ and $X^2$ are each hydrogen, $X^3$ is hydrogen or alkyl, $X^4$ is —C(O)O$X^{40}$, and $X^{40}$ is hydrogen, hydrocarbyl, substituted hydrocarbyl, heterohydrocarbyl, substituted heterohydrocarbyl, or heterocyclo. In a further example, the hydrophilic block comprises repeat units corresponding to Formula 1, $X^1$ and $X^2$ are each hydrogen, $X^3$ is hydrogen or alkyl, $X^4$ is —C(O)O$X^{40}$, $X^{40}$ is —(CH$_2$CH$_2$O)$_t X^{400}$, t is a positive integer, and $X^{400}$ is alkyl, substituted alkyl, or heterocyclo. In a further example, the hydrophilic block comprises repeat units corresponding to Formula 1, $X^1$ and $X^2$ are each hydrogen, $X^3$ is hydrogen or alkyl, $X^4$ is —C(O)O$X^{40}$, $X^{40}$ is —(CH$_2$CH$_2$O)$_t X^{400}$, t is a positive integer, and $X^{400}$ comprises a targeting moiety. In a further example, the hydrophilic block comprises repeat units corresponding to Formula 1 and the repeat units corresponding to Formula 1 constitute a majority of the total number of repeat units in the hydrophilic block. In a further example, the hydrophilic block comprises repeat units corresponding to Formula 1 and the repeat units corresponding to Formula 1 constitute at least 75% of the total number of repeat units in the hydrophilic block. In a further example, the hydrophilic block comprises repeat units corresponding to Formula 1 and the repeat units corresponding to Formula 1 constitute at least 90% of the total number of repeat units in the hydrophilic block.

In one alternative embodiment, the hydrophilic block is a random copolymer comprising at least two compositionally distinct repeat units, at least one of which corresponds to Formula 1. In another alternative embodiment, the hydrophilic block is a random copolymer comprising at least two compositionally distinct repeat units, each of which corresponds to Formula 1. For example, the hydrophilic block may be a random copolymer comprising (i) a first repeat unit corresponding to Formula 1 in which $X^4$ is —C(O)OH and (ii) a compositionally distinct second repeat unit corresponding to Formula 1. In a further example, the hydrophilic block is a random copolymer comprising at least two compositionally distinct repeat units, each of which corresponds to Formula 1, and the repeat units corresponding to Formula 1 constitute a majority of the total number of repeat units in the hydrophilic block. In a further example, the hydrophilic block is a random copolymer comprising at least two compositionally distinct repeat units, each of which corresponds to Formula 1, and the repeat units corresponding to Formula 1 constitute at least 90% of the total number of repeat units in the hydrophilic block.

In another preferred embodiment, the hydrophilic block comprises repeat units corresponding to Formula 1ETS

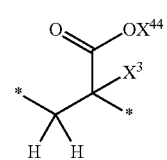

Formula 1ETS wherein * designates the point of attachment of the repeat unit of Formula 1ETS to other repeat units, $X^3$ is alkyl, and $X^{44}$ is a targeting or shielding moiety. For example, $X^{44}$ may be a polyol, a vitamin, a peptide, or other moiety that has a binding affinity for a cellular or biological target. For example, in one such embodiment the hydrophilic block comprises repeat units corresponding to Formula 1ETS and $X^{44}$ is a polyol. In a further example, the hydrophilic block comprises repeat units corresponding to Formula 1ETS and the repeat units corresponding to Formula 1ETS may constitute at least 2% of the total number of repeat units in the hydrophilic block. In a further example, the hydrophilic block comprises repeat units corresponding to Formula 1ETS and the repeat units corresponding to Formula 1ETS may constitute at least 5% of the total number of repeat units in the hydrophilic block. In a further example, the hydrophilic block is a random copolymer comprising at least two repeat units, one corresponding to Formula 1ETS and the other being a compositionally distinct repeat unit corresponding to Formula 1. In a further example, the hydrophilic block is a random copolymer comprising at least two repeat units, one corresponding to Formula 1ETS and another corresponding to Formula 1 wherein $X^4$ is —COOH.

In certain embodiments, the hydrophilic block comprises a plurality of monomeric residues obtained by the polymerization or copolymerization of a monomer of Formula IIIb:

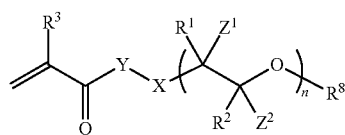

(IIIb)

wherein:

n is an integer ranging from 2 to 20;

X is —$(CR^1R^2)_m$— wherein m is 0-10, and wherein one or more $(CR^1R^2)$ unit is optionally substituted with —$NR^1R^2$, —$OR^1$ or —$SR^1$, Y is —O—, —$NR^4$— or —$(CR^1R^2)$—, each $R^1$, $R^2$, $R^3$, $Z^1$ and $Z^2$ are independently selected from the group consisting of hydrogen, halogen, and optionally substituted $C_1$-$C_3$ alkyl, $R^4$ is selected from the group consisting of hydrogen, and optionally substituted $C_1$-$C_6$ alkyl, $R^8$ is hydrogen or $(CR^1R^2)_mR^9$, wherein m is 0-10, and wherein one or more $(CR^1R^2)$ unit is optionally substituted with —$NR^1R^2$, —$OR^1$ or —$SR^1$, and $R^9$ is hydrogen, halogen, optionally substituted $C_1$-$C_3$ alkyl, polyol, vitamin, peptide, small molecule having a molecular weight of 200-1200 Daltons, or a conjugatable group.

In certain embodiments, the hydrophilic block comprises a plurality of monomeric residues obtained by the polymerization or copolymerization of a monomer of Formula IIIc:

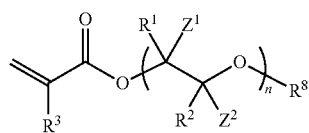

(IIIc)

wherein:

n is an integer ranging from 2 to 20;

X is —$(CR^1R^2)_m$— wherein m is 0-10, and wherein one or more $(CR^1R^2)$ unit is optionally substituted with —$NR^1R^2$, —$OR^1$ or —$SR^1$, Y is —O—, —$NR^4$— or —$(CR^1R^2)$—, each $R^1$, $R^2$, $R^3$, $Z^1$ and $Z^2$ are independently selected from the group consisting of hydrogen, halogen, and optionally substituted $C_1$-$C_3$ alkyl, $R^4$ is selected from the group consisting of hydrogen, and optionally substituted $C_1$-$C_6$ alkyl, $R^8$ is hydrogen or $(CR^1R^2)_mR^9$, wherein m is 0-10, and wherein one or more $(CR^1R^2)$ unit is optionally substituted with —$NR^1R^2$, —$OR^1$ or —$SR^1$, and $R^9$ is hydrogen, halogen, optionally substituted $C_1$-$C_3$ alkyl, polyol, vitamin, peptide, small molecule having a molecular weight of 200-1200 Daltons, or a conjugatable group.

For example, in one embodiment, the hydrophilic first block a plurality of monomeric residues corresponding to Formula IIIc, $R^1$, $R^2$, $Z^1$ and $Z^2$ are hydrogen, $R^3$ is hydrogen or $C_1$-$C_3$ alkyl, n is 2-20 and $R^9$ is a polyol, vitamin, peptide, or small molecule having a molecular weight of 200-1200 Daltons.

In certain embodiments, the hydrophilic first block or shielding hydrophilic block comprises a plurality of monomeric residues obtained by the polymerization or copolymerization of a monomer of Formula III:

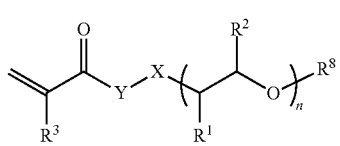

(III)

wherein:

X is $(CR^1R^2)_m$, wherein m is 0-10, and wherein one or more $(CR^1R^2)$ unit is optionally substituted with $NR^1R^2$, $OR^1$ or $SR^1$, Y is O, $NR^4$, or $CR^1R^2$, each $R^1$, $R^2$, $R^3$ and $R^9$ are independently selected from the group consisting of hydrogen, halogen, optionally substituted $C_1$-$C_3$ alkyl, or a targeting group, such as but not limited to galactose, N-acetyl galactosamine, folate, RGD peptide, $R^4$ is selected from the group consisting of hydrogen, and optionally substituted $C_1$-$C_6$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In specific embodiments, the hydrophilic first block or shielding hydrophilic block comprises a plurality of monomeric residues obtained by the polymerization or copolymerization of a monomer of Formula IIIa:

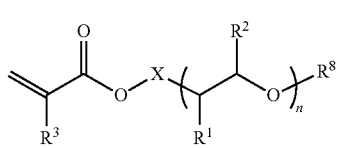

(IIIa)

wherein:

X is $(CR^1R^2)_m$, wherein m is 0-10, and wherein one or more $(CR^1R^2)$ unit is optionally substituted with $NR^1R^2$, $OR^1$ or $SR^1$, each $R^1$, $R^2$, $R^3$ and $R^9$ are independently selected from the group consisting of hydrogen, halogen, and optionally substituted $C_1$-$C_3$ alkyl, n is an integer ranging from 2 to 20, $R^8$ is $(CR^1R^2)_m R^9$, wherein m is 0-10, and wherein one or more $(CR^1R^2)$ unit is optionally substituted with $NR^1R^2$, $OR^1$ or $SR^1$.

In one embodiment, the hydrophilic first block comprises a plurality of monomeric residues corresponding to Formula IIIa and $R^3$ is methyl (i.e., the monomer of Formula III is a PEGMA).

In certain embodiments, the hydrophilic first block or shielding hydrophilic block comprises a plurality of monomeric residues obtained by the polymerization or copolymerization of a monomer of Formula IV:

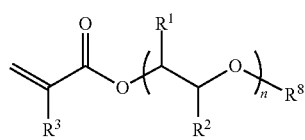

(IV)

wherein:

each $R^1$, $R^2$ and $R^3$ are independently selected from the group consisting of hydrogen, halogen, and optionally substituted $C_1$-$C_3$ alkyl, n is an integer ranging from 2 to 20, $R^8$ is $(CR^1R^2)_m R^9$, wherein m is 0-10, and wherein one or more $(CR^1R^2)$ unit is optionally substituted with $NR^1R^2$, $OR^1$ or $SR^1$.

In one embodiment, the hydrophilic first block comprises a plurality of monomeric residues corresponding to Formula IV, $R^3$ is methyl and n is 2-20.

In general, the hydrophilic first block comprises a plurality of repeat units, i.e., at least two. In some embodiments, a hydrophilic first block of a polymer described herein has a number average molecular weight of about 1,000 Dalton to about 50,000 Dalton, about 2,000 Dalton to about 30,000 Dalton, about 5,000 Dalton to about 20,000 Dalton, or about 7,000 Dalton to about 15,000 Dalton. In specific embodiments, the hydrophilic block is of about 7,000 Dalton, 8,000 Dalton, 9,000 Dalton, 10,000 Dalton, 11,000 Dalton, 12,000 Dalton, 13,000 Dalton, 14,000 Dalton, or 15,000 Dalton.

Carrier Block

The block copolymer described herein comprises a second (i.e., intermediate block, or a block between the hydrophilic first block and the hydrophobic block), that is (i) associated with a therapeutic agent (e.g., polynucleotide or peptide) or (ii) possesses a functional group for associating the therapeutic agent. For example, the carrier block may possess polycations for ionically associating with a therapeutic agent such as a polynucleotide. Alternatively, or additionally, the carrier block, may contain a disulfide linkage or other moiety for divalently coupling the therapeutic agent to the block copolymer. In one embodiment, the carrier (second) block is hydrophilic. In another embodiment, the carrier (second) block is hydrophobic. In one embodiment, the second block is polycationic. In some embodiments, the second block is hydrophilic and comprises a plurality of cationic monomeric residues (e.g., at about neutral pH). In another embodiment, the carrier (second) block is hydrophobic and comprises a plurality of cationic monomeric residues (e.g., at about neutral pH). In specific embodiments, the second block is ionically associated with a polynucleotide. In certain embodiments, the second block is non-charged or, at least substantially non-charged, and is attached to a polynucleotide. In some embodiments, the second block is hydrophilic, polycationic and is attached through both covalent bond and ionic interactions to a polynucleotide.

In general, the carrier block may contain anionic repeat units, cationic repeat units, zwitterionic repeat units, a combination of two or more charged repeat units (e.g., anionic and cationic repeat units, anionic and zwitterionic repeat units, cationic and zwitterionic repeat units, or anionic, cationic and zwitterionic repeat units), substantially non-charged repeat units, or a combination thereof. Stated differently, the carrier block may contain any of a wide range of repeat units, hydrophilic or even hydrophobic. In one embodiment, the sum of the contributions of the repeat units comprised by the carrier block provide a block having an overall hydrophilic character. In an alternative embodiment, the sum of the contributions of the repeat units comprised by the carrier block provide a block having an overall hydrophobic character. When the repeat units contain ionizable groups, the contribution of an individual repeat unit to the overall hydrophilicity of the block of which it is a constituent may vary as a function of its pKa relative to the pH of the environment in which it is found. For example, propyl acrylic acid repeat units, $-CH_2C(CH_2CH_2CH_3)(COOH)-$, are predominantly ionized at pH 7 but not at pH 5 and thus, the hydrophobic contribution of propyl acrylic acid repeat units to a block is significantly greater at pH 5 than at pH 7. In general, therefore, when the carrier block comprises ionizable cationic repeat units or ionizable anionic repeat units and it is desired that the carrier block be hydrophilic, it is preferred that the sum of the contributions of the repeat units constituting the carrier block be such that the overall character of the block is hydrophilic at physiological pH. For example, in one embodiment, it is preferred that the carrier block be hydrophilic over the range of pH from pH 5.0 to pH 7.5. Alternatively, when the carrier block comprises ionizable cationic repeat units or ionizable anionic repeat units and it is desired that the carrier block be hydrophobic, it is preferred that the sum of the contributions of the repeat units constituting the carrier block be such that the overall character of the block is hydrophobic at physiological pH. For example, in one embodiment, the carrier block may be hydrophobic over the range of pH from pH 5.0 to pH 7.5.

In some embodiments, the carrier block comprises repeat units derived from cationic monomers having a pKa ranging anywhere between about 6.0 and about 10.0, typically between about 6.2 and about 9.5, and in some embodiments between about 6.5 and about 8.5. Upon incorporation of the monomer into the polymer block, the pKa of the residue tends to decrease relative to the unpolymerized monomer; in general, therefore, the pKa of the incorporated repeat units will be between about 6.0 and 10.0, typically between about 6.2 and 9.0, and in some embodiments, between about 6.5 and 8.0.

In certain embodiments, the second block is hydrophilic and comprises a monomeric species comprising an acyclic amine (e.g., an amine, an alkyl amine, a dialkyl amine, or the like), an acyclic imine (e.g., an imine, an alkyl imine, or the like), a cyclic amine (e.g., piperidine), a nitrogen containing heterocycle (e.g., pyridine or quinoline), or the like. In specific embodiments, a cationic species utilized herein includes a protonated acyclic amine (e.g., an amine, an alkyl amine, a dialkyl amine, or the like), an acyclic imine (e.g., an imine, an alkyl imine, or the like), a cyclic amine (e.g., piperidine), a nitrogen containing heterocycle (e.g., pyridine or quinoline), or the like.

Non-limiting examples of acyclic amines include methylamine, dimethylamine, ethylamine, diethylamine, propylamine, isopropylamine, diisopropylamine, diisopropylethylamine, n-butylamine, sec-butylamine, tert-butylamine, pentylamine, neo-pentylamine, iso-pentylamine, hexanamine or the like. Non-limiting examples of acyclic imines include methylimine, ethylimine, propylimine, isopropylimine, n-butylimine, sec-butylimine, pentylimine, neo-pentylimine, iso-pentylimine, hexylimine or the like. Non-limiting examples of cyclic amines include cyclopropylamine, cyclobutylamine, cyclopentylamine, cyclohexylamine, cycloheptylamine, piperidine, pyrazine, pyrrolidine, homopiperidine, azabicylcoheptane, diazabicycloundecane, or the like. Non-limiting examples of cyclic imines include cyclopropylimine, cyclobutylimine, cyclopentylimine, cyclohexylimine, cycloheptylimine, or the like. Non-limiting examples of nitrogen containing heteroaryls include imidazolyl, pyrrolyl, pyridyl, indolyl, or the like.

In some embodiments, the second block of a polymer described herein is hydrophilic and comprises a plurality of monomeric residues of optionally substituted, amino($C_1$-$C_6$) alkyl-ethacrylate, amino($C_1$-$C_6$)alkyl-methacrylate, amino ($C_1$-$C_6$)alkyl-acrylate, (N—($C_1$-$C_6$)alkyl-amino($C_1$-$C_6$) alkyl-ethacrylate, N—($C_1$-$C_6$)alkyl-amino($C_1$-$C_6$)alkyl-methacrylate, N—($C_1$-$C_6$)alkyl-amino($C_1$-$C_6$)alkyl-acrylate, (N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or a combination thereof. In specific embodiments, such monomeric residues constitute a cationic monomeric residue at neutral pH as described herein.

In one embodiment, the carrier block comprises a plurality of anionic monomeric residues. The anionic monomeric residues can have a species charged or chargeable to an anion, including a protonatable anionic species. The chargeable species can preferably be anionic at serum physiological pH and substantially neutral or non charged at the pH of the membrane being destabilized or disrupted, e.g., preferably at an endosomal pH. In some embodiments, the carrier block comprises a plurality of anionic hydrophobic monomeric residues, monomeric residues comprising both hydrophobic species (e.g., a $C_2$-$C_8$ alkyl substituent) and species charged or chargeable to an anion.

In some embodiments, the second block is a polymer bioconjugate comprising the polynucleotide covalently coupled to the second block. In some embodiments, covalent conjugates are made between the therapeutic agent (e.g., polynucleotide or peptide) and the pendant side chains of monomers in the polymer. In some embodiments, the second block comprises the polynucleotide covalently coupled to the second block through a linking moiety. In certain embodiments, the second block is covalently coupled to the 3' end of the polynucleotide. In some embodiments, the second block is covalently coupled to the 5' end of the polynucleotide. In certain embodiments, the linking moiety is a covalent bond. In some embodiments, the linking moiety is derived from a multifunctional moiety comprising two or more reactive functional groups. In certain embodiments, the linking moiety is a pH-sensitive labile moiety. In some embodiments, the linking moiety is stable at serum pH and acid labile at endosomal pH. In some embodiments, the linking moiety is stable at pH 7.4 and acid labile at pH 6.0. In certain embodiments, the linking moiety is a disulfide.

In certain embodiments, the second block comprises one or more monomeric residue comprising a conjugatable or conjugated side chain (e.g., a pendant group of a monomeric residue). A conjugated side chain, as used herein is meant to include monomeric residues that when initially polymerized possessed a conjugatable side chain, which was later conjugated, e.g., to a polynucleotide. In some instances, a conjugatable side chain is a group bearing one or more reactive groups that can be used for post-polymerization introduction of additional functionalities via known in the art chemistries, for example, "click" chemistry (for example of "click" reactions, see Wu, P.; Fokin, V. V. Catalytic Azide-Alkyne Cycloaddition: Reactivity and Applications. *Aldrichim. Acta,* 2007, 40, 7-17). In certain embodiments, conjugatable or functionizable side chains provided herein comprise one or more of any suitable electrophilic or nucleophilic functional group, such as but not limited to N-hydrosuccinimide (NHS)ester, HOBt (1-hydroxybenzotriazole) ester, p-nitrophenyl ester, tetrafluorophenyl ester, pentafluorophenyl ester, pyridyl disulfide group, maleimide, aldehyde, ketone, anhydride, thiol, amine, hydroxyl, alkyl halide, or the like. In more specific embodiments, the second block comprises one or more of such functionizable side chains that is bioconjugated with a biomolecule, e.g., a polynucleotide or peptide.

In certain embodiments, the second block comprises monomeric residues derived from polymerization of conjugatable monomers having Formula VIII:

(VIII)

wherein:

X is selected from a group consisting of a covalent bond, C(O), a divalent $C_5$-$C_{10}$ aryl, and a divalent $C_2$-$C_{10}$ heteroaryl, Y is a covalent bond or a linking group selected from optionally substituted divalent $C_1$-$C_{20}$ alkyl, optionally substituted divalent $C_1$-$C_{20}$ heteroalkyl, optionally substituted divalent $C_1$-$C_{20}$ alkenyl, optionally divalent substituted $C_1$-$C_{20}$ alkynyl, optionally substituted divalent $C_1$-$C_{20}$ cycloalkyl, optionally substituted divalent $C_1$-$C_{20}$ cycloheteroalkyl optionally substituted divalent $C_5$-$C_{10}$ aryl, or optionally substituted divalent $C_3$-$C_{10}$ heteroaryl, $R^3$ is selected from the group consisting of hydrogen and optionally substituted $C_1$-$C_4$ alkyl, Q is the conjugatable group such as but not limited to N-hydrosuccinimide (NHS)ester, HOBt (1-hydroxybenzotriazole) ester, p-nitrophenyl ester, tetrafluorophenyl ester, pentafluorophenyl ester, pyridyl disulfide group, maleimide, aldehyde, ketone, anhydride, thiol, amine, hydroxyl, alkyl halide, or the like.

In certain embodiments, the second hydrophilic block further comprises a plurality of monomeric residues described in the hydrophilic block of Formula Ia. In specific embodiments, the second hydrophilic block is a random copolymer comprising at least about 5%, at least about 10%, at least about 20%, at least about 30%, or at least about 40% by weight of monomeric residues (e.g., PEGMA) having a pendant group comprising a shielding oligomer (e.g., a polyethylene glycol).

In alternative embodiments, wherein a therapeutic agent (e.g., polynucleotide or peptide) is conjugated to the "second hydrophilic block", the second block may optionally be replaced with a non-hydrophilic block (e.g., a hydrophobic block), which is conjugated to the therapeutic agent.

In certain embodiments, the intermediate block has the formula:

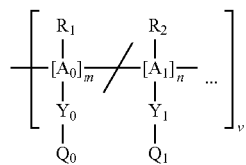

(Ib)

wherein:

$A_0$, and $A_1$ are selected from the group consisting of —C—C—, —C—, —C(O)(C)$_a$C(O)O—, —O(C)$_a$C(O)— and —O(C)$_b$O—;

a is 1-4;

b is 2-4;

$Y_0$, and $Y_1$ are independently selected from the group consisting of a covalent bond, (1C-10C)alkyl-, —C(O)O (2C-10C) alkyl-, —OC(O)(1C-10C) alkyl-, —O(2C-10C) alkyl- and —S(2C-10C)alkyl-, —C(O)NR$_6$(2C-10C) alkyl-;

tetravalent carbon atoms of $A_0$-$A_1$ that are not fully substituted with $R_1$-$R_2$ and $Y_0$-$Y_1$ are completed with an appropriate number of hydrogen atoms;

each $R_1$, $R_2$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_0$ is a residue selected from the group consisting of residues which are hydrophilic at physiologic pH and are at least partially positively charged at physiologic pH (e.g., amino, alkylamino, ammonium, alkylammonium, guanidine, imidazolyl, pyridyl, or the like); conjugatable or functionizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

$Q_1$ is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., a monomeric residue comprising a phosphate group and an ammonium group at physiologic pH);

m is 0 to less than 1.0 (e.g., 0 to about 0.49);

n is greater than 0 to 1.0 (e.g., about 0.51 to about 1.0); wherein m+n=1 v is from about 1 to about 25 kDa.

In certain embodiments, the conjugatable or functionizable residue of $Q_0$ is conjugated to at least one amino acid or at least one nucleic acid.

In one preferred embodiment, the carrier block comprises repeat units corresponding to Formula 1

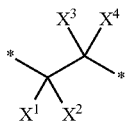

Formula 1 wherein * designates the point of attachment of the repeat unit of Formula 1 to other repeat units; each $X^1$ and $X^2$ is independently selected from the group consisting of hydrogen, hydrocarbyl, substituted hydrocarbyl, heterocyclo, and substituted carbonyl, provided, however, $X^1$ and $X^2$ are not, in the same repeat unit, selected from the group consisting of aryl, heteroaryl, heterosubstituted carbonyl, and combinations thereof; each $X^3$ is independently hydrogen, alkyl or substituted alkyl, and each $X^4$ is independently heterosubstituted carbonyl, aryl, or heteroaryl. For example, in one such embodiment the carrier block comprises repeat units corresponding to Formula 1 and $X^1$ and $X^2$ are each hydrogen. In another such example, the carrier block comprises repeat units corresponding to Formula 1, $X^1$ and $X^2$ are each hydrogen and $X^3$ is hydrogen or alkyl. In a further example, the carrier block comprises repeat units corresponding to Formula 1, $X^1$ and $X^2$ are each hydrogen, $X^3$ is hydrogen or alkyl, and each $X^4$ is independently heterosubstituted carbonyl. In a further example, the hydrophilic block comprises repeat units corresponding to Formula 1, $X^4$ is —C(O)OX$^{40}$, —C(O)SX$^{40}$, or —C(O)NX$^{40}$X$^{41}$, and $X^{40}$ and $X^{41}$ are independently hydrogen, hydrocarbyl, substituted hydrocarbyl, heterohydrocarbyl, substituted heterohydrocarbyl, or heterocyclo. In a further example, the carrier block comprises repeat units corresponding to Formula 1, $X^4$ is —C(O) OX$^{45}$, —C(O)SX$^{45}$, or —C(O)NX$^{41}$X$^{45}$, and $X^{41}$ and $X^{45}$ are independently hydrogen, hydrocarbyl, substituted hydrocarbyl, heterohydrocarbyl, or heterocyclo. In a further example, the carrier block comprises repeat units corresponding to Formula 1, $X^4$ is —C(O)OX$^{45}$ or —C(O) NX$^{41}$X$^{45}$, and $X^{41}$ and $X^{45}$ are independently hydrocarbyl, heterohydrocarbyl, or heterocyclo. In a further example, the carrier block comprises repeat units corresponding to Formula 1, $X^1$ and $X^2$ are each hydrogen, $X^3$ is hydrogen or alkyl, $X^4$ is —C(O)OX$^{45}$, and $X^{45}$ is hydrogen, hydrocarbyl, substituted hydrocarbyl, heterohydrocarbyl, substituted heterohydrocarbyl, or heterocyclo. In a further example, the carrier block comprises repeat units corresponding to Formula 1, $X^1$ and $X^2$ are each hydrogen, $X^3$ is hydrogen or alkyl, $X^4$ is —C(O)OX$^{45}$, $X^{45}$ is a disulfide substituted alkyl moiety (for example, pyridyl disulfide substituted ethyl). In a further example, the carrier block comprises repeat units corresponding to Formula 1, $X^1$ and $X^2$ are each hydrogen, $X^3$ is hydrogen or alkyl, $X^4$ is —C(O)NX$^{41}$X$^{45}$, $X^{41}$ is hydrogen, and $X^{45}$ is alkyl or substituted alkyl.

In one alternative embodiment, the carrier block is a random copolymer comprising at least two compositionally distinct repeat units, each of which corresponds to Formula 1. For example, the carrier block may be a random copolymer comprising (i) a first repeat unit corresponding to Formula 1 in which $X^4$ is —C(O)OX$^{45}$ and (ii) a second repeat unit corresponding to Formula 1 in which $X^4$ is —C(O)NX$^{41}$X$^{45}$. Advantageously, when the carrier block is a random copolymer comprising at least two compositionally distinct repeat units, one of the repeat units may provide a functional group for attaching a therapeutic agent such as a nucleic acid. Thus, for example, the carrier block may comprise (i) a first repeat unit corresponding to Formula 1 wherein $X^4$ is —C(O)OX$^{45}$, —C(O)SX$^{45}$, or —C(O)

$NX^{41}X^{45}$ and a therapeutic agent such as a nucleic acid is attached to the carrier block via $X^{45}$ or $X^{45}$ comprises a functional group for attaching the therapeutic agent, and (ii) a compositionally distinct repeat unit corresponding to Formula 1.

In certain embodiments, the carrier block comprises a plurality of monomeric residues obtained by the polymerization or copolymerization of a monomer of Formula IIIb:

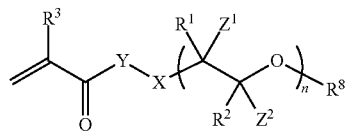

(IIIb)

wherein:

n is an integer ranging from 2 to 20;

X is $-(CR^1R^2)_m-$ wherein m is 0-10, and wherein one or more $(CR^1R^2)$ unit is optionally substituted with $-NR'-R^2$, $-OR^1$ or $-SR^1$, Y is $-O-$, $-NR^4-$ or $-(CR^1R^2)-$, each $R^1$, $R^2$, $R^3$, $Z^1$ and $Z^2$ are independently selected from the group consisting of hydrogen, halogen, and optionally substituted $C_1$-$C_3$ alkyl, $R^4$ is selected from the group consisting of hydrogen, and optionally substituted $C_1$-$C_6$ alkyl, $R^8$ is hydrogen or $(CR^1R^2)_mR^9$, wherein m is 0-10, and wherein one or more $(CR^1R^2)$ unit is optionally substituted with $-NR^1R^2$, $-OR^1$ or $-SR^1$, and $R^9$ is hydrogen, halogen, optionally substituted $C_1$-$C_3$ alkyl, polyol, vitamin, peptide, small molecule having a molecular weight of 200-1200 Daltons, or a conjugatable group.

In certain embodiments, the carrier block comprises a plurality of monomeric residues obtained by the polymerization or copolymerization of a monomer of Formula IIIc:

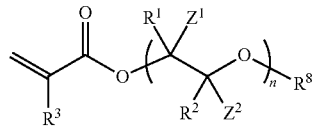

(IIIc)

wherein:

n is an integer ranging from 2 to 20;

X is $-(CR^1R^2)_m-$ wherein m is 0-10, and wherein one or more $(CR^1R^2)$ unit is optionally substituted with $-NR^1-R^2$, $-OR^1$ or $-SR^1$, Y is $-O-$, $-NR^4-$ or $-(CR^1R^2)-$, each $R^1$, $R^2$, $R^3$, $Z^1$ and $Z^2$ are independently selected from the group consisting of hydrogen, halogen, and optionally substituted $C_1$-$C_3$ alkyl, $R^4$ is selected from the group consisting of hydrogen, and optionally substituted $C_1$-$C_6$ alkyl, $R^8$ is hydrogen or $(CR^1R^2)_mR^9$, wherein m is 0-10, and wherein one or more $(CR^1R^2)$ unit is optionally substituted with $-NR^1R^2$, $-OR^1$ or $-SR^1$, and $R^9$ is hydrogen, halogen, optionally substituted $C_1$-$C_3$ alkyl, polyol, vitamin, peptide, small molecule having a molecular weight of 200-1200 Daltons, or a conjugatable group.

In certain embodiments, the carrier block comprises a plurality of monomeric residues obtained by the polymerization or copolymerization of a monomer of Formula III:

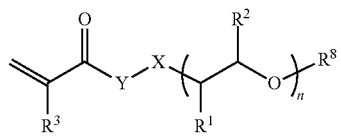

(III)

wherein:

X is $(CR^1R^2)_m$, wherein m is 0-10, and wherein one or more $(CR^1R^2)$ unit is optionally substituted with $NR^1R^2$, $OR^1$ or $SR^1$, Y is O, $NR^4$, or $CR^1R^2$, each $R^1$, $R^2$, $R^3$ and $R^9$ are independently selected from the group consisting of hydrogen, halogen, optionally substituted $C_1$-$C_3$ alkyl, or a targeting group, such as but not limited to galactose, N-acetyl galactosamine, folate, RGD peptide, $R^4$ is selected from the group consisting of hydrogen, and optionally substituted $C_1$-$C_6$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In specific embodiments, the hydrophilic first block or shielding hydrophilic block comprises a plurality of monomeric residues obtained by the polymerization or copolymerization of a monomer of Formula IIIa:

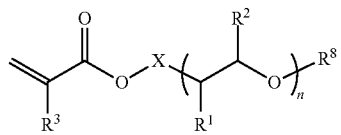

(IIIa)

wherein:

X is $(CR^1R^2)_m$, wherein m is 0-10, and wherein one or more $(CR^1R^2)$ unit is optionally substituted with $NR^1R^2$, $OR^1$ or $SR^1$, each $R^1$, $R^2$, $R^3$ and $R^9$ are independently selected from the group consisting of hydrogen, halogen, and optionally substituted $C_1$-$C_3$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In specific embodiments, $R^3$ is methyl (i.e., the monomer of Formula III is a PEGMA).

In certain embodiments, the hydrophilic first block or shielding hydrophilic block comprises a plurality of monomeric residues obtained by the polymerization or copolymerization of a monomer of Formula IV:

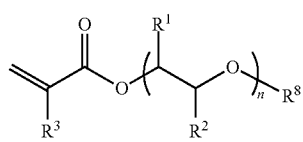

(IV)

wherein:

each $R^1$, $R^2$ and $R^3$ are independently selected from the group consisting of hydrogen, halogen, and optionally substituted $C_1$-$C_3$ alkyl, n is an integer ranging from 2 to 20, $R^8$ is $(CR^1R^2)_mR^9$, wherein m is 0-10, and wherein one or more $(CR^1R^2)$ unit is optionally substituted with $NR^1R^2$, $OR^1$ or $SR^1$.

In general, the carrier block comprises a plurality of repeat units, i.e., at least two. In some embodiments, the carrier or second block of a polymer described herein has a number average molecular weight of about 1,000 Dalton to about 50,000 Dalton, about 2,000 Dalton to about 30,000 Dalton, about 5,000 Dalton to about 20,000 Dalton, or about 7,000 Dalton to about 15,000 Dalton. In specific embodiments, the hydrophilic block is of about 7,000 Dalton, 8,000 Dalton, 9,000 Dalton, 10,000 Dalton, 11,000 Dalton, 12,000 Dalton, 13,000 Dalton, 14,000 Dalton, or 15,000 Dalton.

Hydrophobic Block

In certain embodiments, a hydrophobic block of a polymer described herein is a hydrophobic pH-dependent, membrane destabilizing block. In some embodiments, a hydrophobic block of a polymer described herein is or comprises a polymer block comprising a plurality of hydrophobic monomeric residues and a plurality of anionic monomeric residues. In specific embodiments, the plurality of anionic monomeric residues is anionic at about neutral pH. In more specific embodiments, at least 50%, at least 70%, at least 80%, at least 90%, at least 95%, or at least 99% of the plurality of anionic monomeric residues are non-charged at about pH 5, at about pH 5.5, at about pH 5.7, at about pH 6.0, at about pH 6.2, at about pH 6.5, or at about endosomal pH (e.g., as calculated from the pKa value of the given monomeric residue).

In certain embodiments, the hydrophobic species or hydrophobic monomeric unit has a π value of the hydrophobic block ranging from about 1 to about 20. A compound's π value, which is a measure of its relative hydrophilic-lipophilic value (see, e.g., Cates, L. A., "Calculation of Drug Solubilities by Pharmacy Students" *Am. J. Pharm. Educ.* 45:11-13 (1981)), is used to describe the compound's hydrophobicity or hydrophilicity.

In certain embodiments, a hydrophobic block described herein comprises a plurality hydrophobic species (used interchangeably herein with "hydrophobicity enhancers"). Hydrophobic species may include, by way of non-limiting example, alkyl (which, as used herein, includes saturated and unsaturated alkyl groups), aryl-alkyl, alkyl-aryl, alkyl-aryl-alkyl, heteroalkyl, aryl, heteroaryl, or the like, each of which being optionally substituted. In specific embodiments, the hydrophobic species is an alkyl, aryl-alkyl, alkyl-aryl, alkyl-aryl-alkyl, or aryl.

In some embodiments, a hydrophobic block described herein comprises a plurality of non-charged (i.e., substantially free of a whole charge, or completely free of a whole charge) hydrophobic monomeric residues. In specific embodiments, hydrophobic monomeric residues comprise at least one hydrophobic species. Hydrophobic species may include, by way of non-limiting example, alkyl (which, as used herein, includes saturated and unsaturated alkyl groups), aryl-alkyl, alkyl-aryl, alkyl-aryl-alkyl, heteroalkyl, aryl, heteroaryl, or the like, each of which being optionally substituted. In specific embodiments, the hydrophobic species is an alkyl, aryl-alkyl, alkyl-aryl, alkyl-aryl-alkyl, or aryl. In some embodiments, polymer chains can independently comprise a plurality of monomeric residues having a hydrophobic species selected from $(C_2$-$C_8)$ alkyl, $(C_2$-$C_8)$ alkenyl, $(C_2$-$C_8)$ alkynyl, aryl, and heteroaryl (each of which may be optionally substituted). In certain embodiments, the plurality of monomeric residues can be derived from polymerization of $(C_2$-$C_8)$ alkyl ethacrylate, a $(C_2$-$C_8)$ alkyl methacrylate, or a $(C_2$-$C_8)$ alkyl acrylate (each of which may be optionally substituted).

In one embodiment, the hydrophobic block comprises a plurality of anionic monomeric residues. In general, it is preferred that the hydrophobic block comprises in the tens or even hundreds of anionic monomeric residues. For example, in one embodiment, the hydrophobic block comprises at least 10 such residues. In another embodiment, it comprises as least 20 such residues. In another embodiment, it comprises at least 50 such residues. In another embodiment, it comprises at least 100 such residues. In such embodiments, the hydrophobic block will typically comprise about 10 to about 500 anionic residues. The anionic monomeric residues can have a species charged or chargeable to an anion, including a protonatable anionic species. The chargeable species can preferably be anionic at serum physiological pH and substantially less charged at the pH of the membrane being destabilized or disrupted, e.g., preferably at an endosomal pH. In some preferred embodiments, the hydrophobic block comprises a plurality of anionic hydrophobic monomeric residues, monomeric residues comprising both hydrophobic species (e.g., a $C_2$-$C_8$ alkyl substituent) and species charged or chargeable to an anion. In each of such aforementioned embodiments, the hydrophobic block can be considered hydrophobic in the aggregate.

In general, therefore, the hydrophobic block may contain anionic repeat units, cationic repeat units, zwitterionic repeat units, a combination of two or more charged repeat units (e.g., anionic and cationic repeat units, anionic and zwitterionic repeat units, cationic and zwitterionic repeat units, or anionic, cationic and zwitterionic repeat units), substantially non-charged repeat units, or a combination thereof, provided that its overall character is hydrophobic. Stated differently, the hydrophobic block may contain any of a wide range of repeat units, hydrophobic or even hydrophilic, provided that the sum of the contributions of the repeat units comprised by the hydrophobic block provide a block having an overall hydrophobic character. When the repeat units contain ionizable groups, the contribution of an individual repeat unit to the overall hydrophilicity of the block of which it is a constituent may vary as a function of its pKa relative to the pH of the environment in which it is found. For example, propyl acrylic acid repeat units, —$CH_2C(CH_2CH_2CH_3)$(COOH)—, are predominantly ionized at pH 7 but not at pH 5 and thus, the hydrophobic contribution of propyl acrylic acid repeat units to a block is significantly greater at pH 5 than at pH 7. In general, therefore, it is preferred that the sum of the contributions of the repeat units constituting the hydrophobic block be such that the overall character of the block is hydrophobic at pH's that are less than physiological pH. For example, in one embodiment, the sum of the contributions is such that the overall character of the block is hydrophobic at a pH of about 5.0. By way of further example, in one embodiment, the sum of the contributions is such that the overall character of the block is hydrophobic at a pH of about 5.5. By way of further example, in one embodiment, the sum of the contributions is such that the overall character of the block is hydrophobic at a pH of about 6.0. By way of further example, in one embodiment, the sum of the contributions is such that the overall character of the block is hydrophobic at a pH of about 6.8. By way of further example, in one embodiment, the sum of the contributions of the repeat units is such that the overall character of the hydrophobic block is hydrophobic at a pH within the range of about 6.2 to 6.8.

In certain embodiments, a hydrophobic block described herein comprises monomeric residues resulting from the polymerization or copolymerization of a monomer comprising a hydrophobic species. Monomers comprising a hydrophobic species include, by way of non-limiting example, optionally substituted, ($C_2$-$C_8$)alkyl-ethacrylate, a ($C_2$-$C_8$) alkyl-methacrylate, a ($C_2$-$C_8$)alkyl-acrylate, styrene, ($C_2$-$C_8$)alkyl-vinyl, or the like. In certain embodiments, monomers comprising a hydrophobic species include, by way of non-limiting example, monomers of Formula VI:

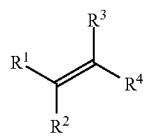

(VI)

wherein:

$R^1$ and $R^2$ are each independently hydrogen, halogen, optionally substituted $C_1$-$C_6$ alkyl, optionally substituted alkenyl, optionally substituted alkynyl, optionally substituted cycloalkyl, optionally substituted aryl, or optionally substituted heteroaryl;

$R^3$ is hydrogen, halogen, optionally substituted $C_1$-$C_6$ alkyl, or —C(=O)$R^5$;

$R^4$ is hydrogen, halogen, optionally substituted $C_1$-$C_6$ alkyl;

$R^5$ is optionally substituted $C_1$-$C_6$ alkyl, —$SR^6$, —$OR^6$, or —$NR^7R^8$;

$R^6$ is hydrogen, optionally substituted $C_1$-$C_6$ alkyl, optionally substituted alkenyl, optionally substituted alkynyl, optionally substituted cycloalkyl, optionally substituted aryl, or optionally substituted heteroaryl;

$R^7$ and $R^8$ are each independently hydrogen, optionally substituted alkyl, optionally substituted heteroalkyl, optionally substituted cycloalkyl, optionally substituted aryl; or $R^7$ and $R^8$ together with the nitrogen to which they are attached form an optionally substituted heterocycle.

In certain embodiments, in addition to a hydrophobic species, a hydrophobic block described herein further comprises an anionic species. In specific embodiments, the anionic species is anionic at about neutral pH. In specific embodiments, the hydrophobic block comprises a first monomer residue comprising a hydrophobic species and a second monomer residue comprising an anionic species.

In certain embodiments, a hydrophobic block described herein comprises a polymer block comprising a plurality of hydrophobic monomeric residues and a plurality of anionic monomeric residues. In some embodiments, a hydrophobic block described herein comprises a polymer block comprising a plurality of chargeable residues. In some embodiments, monomeric residues that are anionic, (1) are anionic at about neutral pH, a pH greater than about 7.2, or any pH greater than about 7.4, and (2) are non-charged at a pH of less than about 6, less than about 5.8, less than about 5.7, less than about 5.6, less than about 5.5, less than about 5.4, less than about 5.2, less than about 5.0, or less than about 4.5. In some embodiments, the monomeric residues have a pKa anywhere between about 4.5 and about 8.0, anywhere between about 5.5 and about 7.5, or anywhere between about 6.0 and about 7.0. In certain embodiments, monomers that when polymerized provide the anionic monomeric residues have a pKa anywhere between about 4.5 and about 8.0, anywhere between about 5.5 and about 7.5, or anywhere between about 6.0 and about 7.0.

In specific embodiments, anionic species which may be found on anionic monomeric residues described herein include, by way of non-limiting example, carboxylic acid, sulfonamide, boronic acid, sulfonic acid, sulfinic acid, sulfuric acid, phosphoric acid, phosphinic acid, and phosphorous acid groups, or the conjugate bases or anions thereof. In some embodiments, the anionic monomeric residue is a residue of ($C_1$-$C_8$)alkylacrylic acid, or acrylic acid. In certain embodiments monomers such as maleic-anhydride, (Scott M. Henry, Mohamed E. H. El-Sayed, Christopher M. Pirie, Allan S. Hoffman, and Patrick S. Stayton, pH-Responsive Poly(styrene-alt-maleic anhydride) Alkylamide Copolymers for Intracellular Drug Delivery. *Biomacromolecules* 2006, 7, 2407-2414) are used for introduction of anionic species by post-polymerization hydrolysis of the maleic anhydride monomeric units.

In certain embodiments, in addition to a hydrophobic species, a hydrophobic block described herein further comprises a cationic species. In some embodiments, in addition to a hydrophobic species and an anionic species, a hydrophobic block described herein further comprises a cationic species. In certain embodiments, in addition to a hydrophobic monomeric residue, a hydrophobic block described herein further comprises a cationic monomeric residue. In some embodiments, in addition to a hydrophobic monomeric residue and an anionic monomeric residue, a hydrophobic block described herein further comprises a cationic monomeric residue. In some embodiments, species and/or monomeric residues that are cationic are cationic at about neutral pH.

In some embodiments, a cationic monomeric residues described herein has a pKa ranging anywhere between about 6.0 and about 10.0, typically between about 6.2 and about 9.5, and in some embodiments between about 6.5 and about 8.5. Upon incorporation of the monomer into the polymer block, the pKa of the residue tends to decrease relative to the unpolymerized monomer; in general, therefore, the pKa of the incorporated repeat units will be between about 6.0 and 10.0, typically between about 6.2 and 9.0, and in some embodiments, between about 6.5 and 8.0

In certain embodiments, the hydrophobic block comprises a monomeric species comprising an acyclic amine (e.g., an amine, an alkyl amine, a dialkyl amine, or the like), an acyclic imine (e.g., an imine, an alkyl imine, or the like), a cyclic amine (e.g., piperidine), a nitrogen containing heterocycle (e.g., pyridine or quinoline), or the like. In specific embodiments, a cationic species utilized herein includes a protonated acyclic amine (e.g., an amine, an alkyl amine, a dialkyl amine, or the like), an acyclic imine (e.g., an imine, an alkyl imine, or the like), a cyclic amine (e.g., piperidine), a nitrogen containing heterocycle (e.g., pyridine or quinoline), or the like.

Non-limiting examples of acyclic amines include methylamine, dimethylamine, ethylamine, diethylamine, propylamine, isopropylamine, diisopropylamine, diisopropylethylamine, n-butylamine, sec-butylamine, tert-butylamine, pentylamine, neo-pentylamine, iso-pentylamine, hexanamine or the like. Non-limiting examples of acyclic imines include methylimine, ethylimine, propylimine, isopropylimine, n-butylimine, sec-butylimine, pentylimine, neo-pentylimine, iso-pentylimine, hexylimine or the like. Non-limiting examples of cyclic amines include cyclopropylamine, cyclobutylamine, cyclopentylamine, cyclohexylamine, cycloheptylamine, piperidine, pyrazine, pyrrolidine, homopiperidine, azabicylcoheptane, diazabicycloundecane, or the like. Non-limiting examples of cyclic imines include cyclopropylimine, cyclobutylimine, cyclopentylimine, cyclohexylimine, cycloheptylimine, or the like. Non-limiting examples of nitrogen containing heteroaryls include imidazolyl, pyrrolyl, pyridyl, indolyl, or the like.

In some embodiments, a hydrophobic block of a polymer described herein comprises a plurality of monomeric residues of optionally substituted, amino($C_1$-$C_6$)alkyl-ethacrylate, amino($C_1$-$C_6$)alkyl-methacrylate, amino($C_1$-$C_6$)alkyl-acrylate, (N—($C_1$-$C_6$)alkyl-amino($C_1$-$C_6$)alkyl-ethacrylate, N—($C_1$-$C_6$)alkyl-amino($C_1$-$C_6$)alkyl-methacrylate, N—($C_1$-$C_6$)alkyl-amino($C_1$-$C_6$)alkyl-acrylate, (N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or a combination thereof. In specific embodiments, such monomeric residues constitute a cationic monomeric residue at neutral pH as described herein.

In certain embodiments, a hydrophobic block described herein comprises a plurality of anionic monomeric residues, a plurality of cationic monomeric residues, and a plurality of hydrophobic monomeric residues.

In certain specific embodiments, at about neutral pH (e.g., at about pH 7.4), the hydrophobic block has a substantially neutral overall charge. In still more specific embodiments, a substantially neutral overall charge of the hydrophobic block means that at least 60%, at least 70%, at least 80%, at least 90%, at least 95%, or at least 98% of the charge of either of the cationic monomeric residues or the anionic monomeric residues are neutralized by the charge of the of the other of the cationic monomeric residues or the anionic monomeric residues. In other words, in various embodiments, the ratio of the number of monomeric units in the hydrophobic block that are cationic at about neutral pH to the number of monomeric units in the hydrophobic block that are anionic at about neutral pH is between about 3:5 and about 5:3, about 7:10 and about 10:7, about 4:5 and about 5:4, about 9:10 and about 10:9, about 95:100 and about 100:95, or about 98:100 and about 100:98. Determination of charge ratios can be achieved in any suitable manner, e.g., by calculating the amount of charged species using the pKa and/or pKb values thereof.

In some embodiments, at about neutral pH (e.g., at about pH 7.4), the hydrophobic block comprises anionic species and cationic species in a ratio of about 10:1 to about 1:10, about 5:1 to about 1:5, about 4:1 to about 1:4, about 1:0 to about 1:4 (anionic species:cationic species). In a preferred embodiment, at about neutral pH (e.g., at about pH 7.4), the hydrophobic block comprises anionic species and cationic species in a ratio of about 1:1 (anionic species:cationic species). In some embodiments, at about neutral pH (e.g., at about pH 7.4), the hydrophobic block comprises anionic monomeric residues and cationic monomeric residues in a ratio of about 1:0 to about 1:4 (anionic monomeric residues:cationic monomeric residues). In a preferred embodiment, at about neutral pH (e.g., at about pH 7.4), the hydrophobic block comprises anionic monomeric residues and cationic monomeric residues in a ratio of about 1:1 (anionic monomeric residues:cationic monomeric residues).

In certain embodiments, at about neutral pH (e.g., at about pH 7.4), the hydrophobic block comprises hydrophobic monomeric residues, cationic monomeric residues, and anionic monomeric residues. In specific embodiments, the ratio of hydrophobic monomeric residues to charged monomeric residues (cationic monomeric residues plus anionic monomeric residues), is about 1:5 to about 5:1, or about 1:3 to about 3:1, or about 1:2 to about 3:1, or about 1:1, or about 1:2, or about 2:1.

In certain embodiments, a hydrophobic block, as described herein comprises a plurality of first monomeric residues derived from a first polymerizable monomer having a protonatable anionic species and a hydrophobic species, and optionally a plurality of second monomeric residues derived from a second polymerizable monomer having a deprotonatable cation species.

In some embodiments, a hydrophobic block, as described herein comprises the structure of Formula Ic:

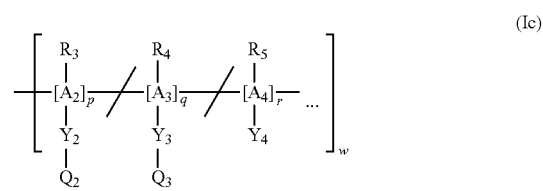

wherein $A_2$, $A_3$ and $A_4$ are independently selected from the group consisting of —C—C—, —C—, —C(O)(C)$_a$C(O)O—, —O(C)$_a$C(O)— and —O(C)$_b$O—; wherein, a is 1-4;

b is 2-4;

$Y_4$ is selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C) and aryl, any of which is optionally substituted with one or more fluorine groups;

$Y_2$ is selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl- —C(O)NR$_6$(2C-10C) alkyl-;

$Y_3$ is selected from the group consisting of a covalent bond, (1C-10C)alkyl and (6C-10C)aryl; wherein tetravalent carbon atoms of $A_2$-$A_4$ that are not fully substituted with $R_3$-$R_5$ and $Y_2$-$Y_4$ are completed with an appropriate number of hydrogen atoms;

each $R_3$, $R_4$, and $R_5$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_2$ is a residue which is positively charged at physiologic pH, including but not limited to amino, alkylamino, ammonium, alkylammonium, guanidine, imidazolyl, and pyridyl;

$Q_3$ is a residue which is negatively charged at physiologic pH, but undergoes protonation at lower pH, including but not limited to carboxyl, sulfonamide, boronate, phosphonate, and phosphate;

p is about 0.1 to about 0.9 (e.g., about 0.2 to about 0.5);

q is about 0.1 to about 0.9 (e.g., about 0.2 to about 0.5); wherein:

r is 0 to about 0.8 (e.g., 0 to about 0.6); wherein p+q+r=1; and, w is from about 1 to about 50 kDa.

In one preferred embodiment, the hydrophobic block comprises repeat units corresponding to Formula 1A

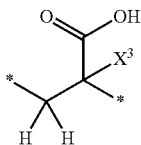

Formula 1A wherein * designates the point of attachment of the repeat unit of Formula 1A to other repeat units; and $X^3$ is alkyl. Exemplary alkyls include methyl, ethyl, propyl and butyl. Typically, $X^3$ is ethyl or propyl. In a preferred embodiment, $X^3$ is propyl.

In one preferred embodiment, the hydrophobic block comprises repeat units corresponding to Formula 1E

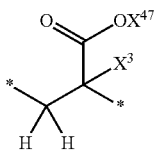

Formula 1E wherein * designates the point of attachment of the repeat unit of Formula 1E to other repeat units; and $X^3$ and $X^{47}$ are independently alkyl. Exemplary alkyls include methyl, ethyl, propyl and butyl. Typically, $X^3$ is methyl, ethyl or propyl and $X^{47}$ is independently methyl, ethyl, propyl or butyl. In one preferred embodiment, $X^3$ is methyl and $X^{47}$ is butyl.

In one preferred embodiment, the hydrophobic block comprises repeat units corresponding to Formula 1C

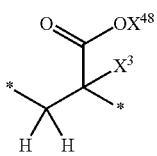

Formula 1C wherein * designates the point of attachment of the repeat unit of Formula 1C to other repeat units; $X^3$ is alkyl, and $X^{48}$ is amino-substituted alkyl. Exemplary alkyls include methyl, ethyl, propyl and butyl. Typically, $X^3$ is ethyl or propyl and $X^{48}$ is N,N-dialkylaminoalkyl, e.g., N,N-dimethylaminoethyl.

In one preferred embodiment, the hydrophobic block is a random copolymer comprising (i) repeat units corresponding to Formula 1A and Formula 1 E, (ii) repeat units corresponding to Formula 1A and 1C, or (iii) repeat units corresponding to Formula 1A, 1C and 1E. In general, when the hydrophobic block is a random copolymer comprising repeat units corresponding to Formula 1A and Formula 1E (with or without repeat units corresponding to Formula 1C), the ratio of the number of repeat units corresponding to Formula 1A to the number of repeat units corresponding to Formula 1E in the third block is between about 20:1 and 1:4, respectively. For example, it is generally preferred that the ratio of the number of repeat units corresponding to Formula 1A to the number of repeat units corresponding to Formula 1E in the third block be between about 3:1 and 1:3, respectively. Additionally, it is generally preferred that the number of repeat units corresponding to Formula 1A exceed the number of repeat units corresponding to Formula 1C.

In general, the hydrophobic block comprises a plurality of repeat units, i.e., at least two. In certain embodiments, a hydrophobic block of a polymer described herein has a number average molecular weight of about 1,000 Dalton to about 200,000 Dalton, about 1,000 Dalton to about 100,000 Dalton, about 1,000 Dalton to about 100,000 Dalton, about 5,000 Dalton to about 50,000 Dalton, about 10,000 Dalton to about 50,000 Dalton, about 15,000 Dalton to about 35,000 Dalton, or about 20,000 Dalton to about 30,000 Dalton.

Block Ratios

In certain embodiments, the block copolymer has a ratio of a number-average molecular weight (with the number average molecular weight of the first block, i.e., hydrophilic block, represented by $M_n^{1st}$, the number average molecular weight of second or intermediate or therapeutic carrier block represented by $M_n^{2nd}$, and the number average molecular weight of the third block represented by $M_n^{3rd}$) of $(M_n^{1st}+M_n^{2nd}):(M_n^{3rd})$ of about 2:1 to about 1:9. In some embodiments, $(M_n^{1st}+M_n^{2nd}):(M_n^{3rd})$ is about 1:1 to about 1:3.

Polymerizable Monomers

In certain embodiments, each of the first, second, and third blocks of the block copolymer comprises monomeric residues derived from a polymerizable monomer. As noted previously, the block copolymer may also comprise one or more other blocks in addition to the first, second and third blocks and, in those instances, the at least one of the additional blocks may also comprise monomeric residues derived from a polymerizable monomer. In specific embodiments, any of the monomers polymerized or copolymerized to provide the hydrophilic, intermediate, or hydrophobic blocks include an ethylenically unsaturated monomer. In more specific embodiments, ethylenically unsaturated monomers include, by way of non-limiting example, acrylic monomers, a vinylic monomer, and the like. In some embodiments, the ethylenically unsaturated monomer is an acrylic monomer selected from, by way of non-limiting example, an optionally substituted acrylic acid, an optionally substituted acrylamide, and an optionally substituted acrylate. In certain embodiments, the ethylenically unsaturated monomer is selected from, by way of non-limiting example, optionally $C_1$-$C_8$ alkyl-substituted acrylic acid, an optionally $C_1$-$C_8$ alkyl-substituted acrylamide, and an optionally $C_1$-$C_8$ alkyl-substituted acrylate.

In certain embodiments, block copolymers (e.g., membrane destabilizing block copolymers) of the micelles provided herein comprise ethylenically unsaturated monomers. The term "ethylenically unsaturated monomer" is defined herein as a compound having at least one carbon double or triple bond. The non-limiting examples of the ethylenically unsaturated monomers are: an alkyl (alkyl)acrylate, a methacrylate, an acrylate, an alkylacrylamide, a methacrylamide, an acrylamide, a styrene, an allylamine, an allylammonium, a diallylamine, a diallylammonium, an N-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymers (including, e.g., the membrane destabilizing block copolymers) of the micelles described herein is used. In some embodiments, monomers suitable for use in the preparation of the polymers (including, e.g., the membrane destabilizing block copolymers) of the micelles provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, vinylnaphthalene, vinyl pyridine, ethylvinylbenzene, aminostyrene, vinylpyridine, vinylimidazole, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, functionalized versions of these monomers are optionally used. A functionalized monomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Bronsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the polymers are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiator is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) ("Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001)).

In certain embodiments, Reversible Addition-Fragmentation chain Transfer or RAFT is used in synthesizing ethylenic backbone polymers of this invention. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In most instances, this cycle of addition to the C=S bond followed by fragmentation of the ensuing radical continues until all monomer has been consumed or the reaction is quenched. Generally, the low concentration of active radicals at any particular time limits normal termination reactions.

In some embodiments, polymers (e.g., membrane destabilizing block copolymers) utilized in the micelles provided herein have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, block copolymers (e.g., membrane destabilizing block copolymers) of the micelles provided herein have a polydispersity index (PDI) of less than 2.0, or less than 1.8, or less than 1.6, or less than 1.5, or less than 1.4, or less than 1.3, or less than 1.2.

Polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

In certain embodiments, poly(DMAEMA) and other polymeric entities used herein (e.g., copolymers or copolymer blocks of BMA, DMAEMA and PAA) are prepared in any suitable manner. In one embodiment, poly(DMAEMA/PEGMA) is prepared by co-polymerizing DMAEMA and PEGMA in the presence of the RAFT CTA, ECT, and a radical initiator. In some embodiments, a block, poly (DMAEMA/PEGMA) macroCTA is used to prepare a series of triblock or other multiblock copolymers where the hydrophobic block contains BMA, DMAEMA and PAA. In other specific embodiments, the orientation of the blocks on the triblock or other multiblock polymer is reversed, such that upon self-assembly, the w end of the polymer is exposed on the hydrophilic segment of the micelle. In various embodiments, this is achieved in any suitable manner, including a number of ways synthetically. For example, in some embodiments, the synthesis of the block copolymers described herein begins with the preparation of the PAA/BMA/DMAEMA core-forming hydrophobic block, and the shell-forming hydrophilic, charged block is added in the second synthetic step by subjecting the resulting PAA/BMA/DMAEMA macroCTA to a second RAFT polymerization step. Alternate approaches include reducing the PAA/BMA/DMAEMA macroCTA to form a thiol end and then covalently attaching a pre-formed hydrophilic, charged polymer to the formed thiol. This synthetic approach provides a method for introduction of a reactive group on the w-end of the polymeric chain exposed to the surface of micelle thus providing alternate approaches to chemical conjugation to the micelle.

In some embodiments, block copolymers are synthesized by chemical conjugation of several polymer blocks that are prepared by separate polymerization processes.

In certain embodiments, the ethylenically unsaturated monomer is selected from, by way of non-limiting example:

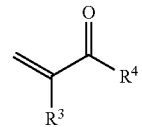

wherein
$R^3$ is hydrogen, halogen, hydroxyl, or optionally substituted $C_1$-$C_3$ alkyl;
$R^4$ is —$SR^5$, —$OR^5$, —$NR^6R^7$, or
$R^4$ is $C_1$-$C_{40}$ alkyl or $C_1$-$C_{40}$ polyoxylatedalkyl, optionally substituted by halogen, cyano, hydroxyl, alkoxy, thiol, alkylthio, silylalkyl, silylaryl, —$NR^9R^{10}$, cycloalkyl, heterocycloalkyl, —C(=O)$OR^9$, —S(=O)$OR^9$, —S(=O)$_2$ $OR^9$, —C(=O)$NR^9R^{10}$, —S(=O)$NR^9R^{10}$, —S(=O)$_2$ $NR^9R^{10}$, a cleavable group or a functionalizable group;
$R^5$ is $C_1$-$C_{40}$ alkyl, $C_1$-$C_{40}$ polyoxylatedalkyl, $C_1$-$C_{40}$ alkenyl, $C_1$-$C_{40}$ alkynyl, cycloalkyl, heterocycloalkyl, aryl, or heteroaryl, optionally substituted by halogen, cyano, hydroxyl, alkoxy, thiol, alkylthio, silylalkyl, silylaryl, —NR$^9$R$^{10}$, cycloalkyl, heterocycloalkyl, —C(═O)OR$^9$, —S(═O)OR$^9$, —S(═O)$_2$OR$^9$, —C(═O)NR$^9$R$^{10}$, —S(═O)NR$^9$R$^{10}$, —S(═O)$_2$NR$^9$R$^{10}$, a cleavable group or a functionalizable group;

R$^6$ and R$^7$ are each independently hydrogen, C$_1$-C$_{40}$ alkyl, C$_1$-C$_{40}$ polyoxylatedalkyl, C$_1$-C$_{40}$ alkenyl, C$_1$-C$_{40}$ alkynyl, cycloalkyl, heterocycloalkyl, aryl, or heteroaryl, optionally substituted by halogen, cyano, hydroxyl, alkoxy, thiol, alkylthio, silylalkyl, silylaryl, —NR$^9$R$^{10}$, cycloalkyl, heterocycloalkyl, —C(═O)OR$^9$, —S(═O)OR$^9$, —S(═O)$_2$OR$^9$, —C(═O)NR$^9$R$^{10}$, —S(═O)NR$^9$R$^{10}$, —S(═O)$_2$NR$^9$R$^{10}$, a cleavable group or a functionalizable group; or R$^6$ and R$^7$ together with the nitrogen to which they are attached form an optionally substituted heterocycle;

R$^9$ and R$^{10}$ are each independently hydrogen, optionally substituted C$_1$-C$_6$ alkyl, optionally substituted cycloalkyl, optionally substituted aryl, optionally substituted heteroaryl, or R$^9$ and R$^{10}$ together with the nitrogen to which they are attached form a heterocycle.

Triblock Copolymers

In certain embodiments, provided herein are triblock copolymers are represented by Formula I:

[A1$_x$-A2$_y$]$_{Mn}$-[A'1$_x$-A'2$_y$]$_{Mn}$-[B1$_x$-B2$_y$-B3$_z$]$_{Mn}$     (I)

In certain embodiments, [A1-A2] is the first block copolymer, composed of monomeric residues A1 and A2, wherein A1 is a hydrophilic monomeric residue, and [A1-A2] is overall hydrophilic. In some embodiments, [A'1-A'2] is the second block copolymer, composed of monomeric residues A'1 and A'2. In certain embodiments, [B1-B2-B3] is the 3rd block copolymer, composed of monomers B1, B2, B3. x, y, z defines the polymer composition in mole % of the individual monomers. Mn is molecular weight of each of the polymer blocks.

In other embodiments, the triblock copolymer is selected from the following triblocks:

| | |
|---|---|
| [PEGMA$_{70}$-MAA(NHS)$_{30}$]-[DMAEMA]-[B-P-D] | (I-1) |
| [DMAEMA$_{70}$-MAA(NHS)$_{30}$]-[DMAEMA]-[B-P-D] | (I-2) |
| [Gal]-[HPMA-PDSMA]-[B-P-D] | (I-3) |
| [Gal-MAA]-[HPMA-PDSMA-MAA]-[B-P-D] | (I-4) |
| [NAcGal]-[HPMA-PDSMA]-[B-P-D] | (I-5) |
| [NAcGal-MAA]-[HPMA-PDSMA-MAA]-[B-P-D] | (I-6) |
| [Gal]-[D]-[B-P-D] | (I-7) |
| [NAcGal]-[D]-[B-P-D] | (I-8) |
| [Gal-MAA]-[D]-[B-P-D] | (I-9) |
| [NAcGal-MAA]-[D]-[B-P-D] | (I-10) |
| [Gal-D]-[D]-[B-P-D] | (I-11) |
| [NAcGal-D]-[D]-[B-P-D] | (I-12) |
| [Gal]-[PA]-[B-P-D] | (I-13) |
| [Gal]-[HPMA-PA]-[B-P-D] | (I-14) |
| [Gal-MAA]-[PA]-[B-P-D] | (I-15) |
| [Gal-MAA]-[HPMA-PA]-[B-P-D] | (I-16) |
| [Gal-D]-[PA]-[B-P-D] | (I-17) |
| [Gal-D]-[HPMA-PA]-[B-P-D] | (I-18) |
| [NAcGal]-[PA]-[B-P-D] | (I-19) |
| [NAcGal]-[HPMA-PA]-[B-P-D] | (I-20) |
| [NAcGal-MAA]-[PA]-[B-P-D] | (I-21) |
| [NAcGal-MAA]-[HPMA-PA]-[B-P-D] | (I-22) |
| [NAcGal-D]-[PA]-[B-P-D] | (I-23) |
| [NAcGal-D]-[HPMA-PA]-[B-P-D] | (I-24) |
| [PAA-BA]-[HPMA-PDSMA]-[Folate] | (I-25) |
| [PAA-BA]-[HPMA-MAA-PDSMA]-[Folate] | (I-26) |
| Folate-[PEG]-[HPMA-PDSMA]-[D-B-P] | (I-27) |
| Folate-[PEG]-[HPMA-MAA-PDSMA]-[D-B-P] | (I-28) | wherein B is the monomeric residue of butyl methacrylate; P is the monomeric residue of propyl acrylic acid; D is the monomeric residue of DMAEMA is dimethylaminoethyl methacrylate; PEGMA is the monomeric residue of polyethyleneglycol methacrylate where, for example, w=4-5 or 7-8 ethylene oxide units, HPMA is the monomeric residue of N-(2-propyl)methacrylamide or N-propylmethacrylate (including all isomers), PA is a primary amino-group containing monomeric residue, NAcGal is the monomeric residue derived from N-Acetyl galactose-PEG-vinyl monomer, Gal is the monomeric residue derived from galactose-PEG-vinyl monomer, PDSMA is the monomeric residue derived from 2-(2-pyridinyldisulfanyl)ethyl methacrylate or 2-(2-pyridinyldisulfanyl)ethyl methacrylamde, and MAA(NHS) is the monomeric residue derived from methylacrylic acid-N-hydroxy succinimide ester. Folate is a folic acid residue which can be conjugated to a pendant group of a monomeric residue, incorporated into a CTA, or conjugated to the thiol derived from the reduction of ω end-group of the polymer. In addition, it should be understood that HPMA-E (2-hydroxypropyl methacrylate or monomeric residue derived therefrom) may be substituted for HPMA in each of the foregoing examples in which HPMA appears, i.e., I-3 to I-5, I-14, I-16, I-18, I-20, I-22, and I-24 to I-28; solely in the interest of brevity, such additional structures are not repeated but shall be considered part of this disclosure.

Micelle

In certain embodiments, micelles are formed from a plurality of polymers comprising a hydrophilic block, a carrier block, and a hydrophobic block as described elsewhere herein. In certain embodiments, a micelle described herein comprises a plurality of block copolymers, the micelle comprising a core and a shell. In specific embodiments, the core of the micelle comprises the hydrophobic blocks of the plurality of block copolymers and the shell comprises the hydrophilic blocks of the block copolymers. Moreover, in more specific embodiments, the shell comprises an inner layer and an outer layer (relative to one another; further layers are also possible), the hydrophilic first block forming the outer layer and the second hydrophilic block forming the inner layer of the micelle shell.

In certain embodiments, the hydrophilic first block is at the surface (or at least nearer the surface of the micelle relative to the hydrophilic or therapeutic associated second block). In certain embodiments, the hydrophilic first block shields (e.g., through steric and/or static interactions) an inner portion of the micelle (e.g., a layer of a micelle made up by the hydrophilic and/or therapeutic associated second block, or a therapeutic agent, such as a polynucleotide, associated with the second block).

In specific embodiments, a plurality of any one or more polymer described herein is assembled into a micelle. In specific embodiments, such a micelle is stable in at about neutral pH (e.g., is stable in an aqueous medium at about pH 7.4).

In some embodiments, a micelle described herein comprises any number of polymers described herein, e.g., about 10 to about 100 of the copolymers described herein per micelle, or about 20 to about 60 of the copolymers described herein per micelle.

In one embodiment, a micelle described herein (without an associated therapeutic agent such as a polynucleotide) has a Zeta potential that is between ±6 mV (millivolt). In one preferred embodiment, a micelle described herein (without an associated therapeutic agent such as a polynucleotide) has a Zeta potential that is between ±5 mV. In one preferred embodiment, a micelle described herein (without an associated therapeutic agent such as a polynucleotide) has a Zeta potential that is between ±2 mV.

In certain embodiments, micelle described herein has a critical micelle concentration, CMC, ranging from about 0.2 ug/ml to about 20 ug/ml. In specific embodiments, the micelle has a critical micelle concentration, CMC, ranging from about 0.5 ug/ml to about 10 ug/ml. In certain embodiments, a micelle described herein comprises a plurality of block copolymers described herein, the plurality of block copolymers described herein having a polydispersity index (PDI) of about 1.0 to about 1.7, or about 1.0 to about 1.4. In some embodiments, a micelle comprises a plurality of copolymers described herein wherein the first block, second block and third block of the block copolymer have a polydispersity index of not more than 1.5.

In certain embodiments, a micelle described herein comprise a plurality of copolymers, as described herein, wherein at least one or more of the plurality of copolymers is covalently crosslinked to the second polymer, whereby the polymeric micelle is a crosslinked polymeric micelle. In specific embodiments, the second polymer is also a copolymer as described herein. In some embodiments, the block copolymer is covalently crosslinked to the hydrophobic block of the second polymer. In specific embodiments, the hydrophobic blocks of two copolymers described herein are cross-linked to each other. In certain embodiments, the block copolymer comprises a plurality of monomeric residues derived from controlled radical polymerization of an ethylenic monomer, at least one such monomer being a bisfunctional crosslinking monomer.

In some embodiments, a micelle provided herein is characterized by one or more of the following: (1) the micelle is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) the micelle is stable to dilution (e.g., down to a polymer concentration of 100 ug/ml, 50 ug/ml, 10 ug/ml, 5 ug/ml or 1 ug/ml, which constitutes the critical stability concentration or the critical micelle concentration (CMC)); (3) the micelle is stable to high ionic strength of the surrounding media (e.g. 0.5M NaCl); and/or (4) the micelle has an increasing instability as the concentration of organic solvent increases, such organic solvents including, but not limited to dimethylformamide (DMF), dimethylsulfoxide (DMSO), and dioxane. In some embodiments, a micelle provided herein is characterized by having at least two of the aforementioned properties. In some embodiments, a micelle provided herein is characterized by having at least three of the aforementioned properties. In some embodiments, a micelle provided herein is characterized by having all of the aforementioned properties.

In some embodiments, a micelle provided herein self-assembles at any suitable concentration. In certain embodiments, a micelle provided herein self-assembles (e.g., has a critical micelle concentration (CMC), or the minimum concentration at which a micelle forms) of about 2 µg/mL, about 5 µg/mL, about 8 µg/mL, about 10 µg/mL, about 20 µg/mL, about 25 µg/mL, about 30 µg/mL, about 40 µg/mL, about 50 µg/mL, about 60 µg/mL, about 70 µg/mL, about 80 µg/mL, about 90 µg/mL, about 100 µg/mL, or greater. In certain embodiments, a micelle provided herein self assembles at least one concentration between about 1 µg/mL and about 100 µg/m L.

In some embodiments, the micelles provided herein are prepared by spontaneous self-assembly of the polymers described herein. In certain embodiments, the polymers described herein assemble into the micelles provided herein upon dilution of a solution of the polymer in water-miscible organic solvent into aqueous media. In some embodiments, the micelles provided herein are formed spontaneously upon dissolution of the polymer directly in aqueous media. In some embodiments, the micelles do not require the presence of a polynucleotide for micelle formation.

In some embodiments, the micelles are stable to dilution in an aqueous solution. In specific embodiments, the micelles are stable to dilution at physiologic pH (including the pH of circulating blood in a human) with a critical stability concentration (e.g., a critical micelle concentration (CMC)) of approximately 50 to approximately 100 µg/mL, or approximately 10 to approximately 50 µg/mL, or less than 10 µg/mL. As used herein, "destabilization of a micelle" means that the polymeric chains forming a micelle at least partially disaggregate, structurally alter (e.g., expand in size and/or change shape), and/or may form amorphous supramolecular structures (e.g., non-micellic supramolecular structures).

In some embodiments, a micelle provided herein is stable in an aqueous medium. In certain embodiments, a micelle provided herein is stable in an aqueous medium at a selected pH, e.g., about physiological pH (e.g., the pH of circulating human plasma). In specific embodiments, a micelle provided herein is stable at about a neutral pH (e.g., at a pH of about 7.4) in an aqueous medium. In specific embodiments, the aqueous medium is animal (e.g., human) serum or animal (e.g., human) plasma. In certain embodiments, a micelle provided herein is stable in human serum and/or human plasma. In specific embodiments, the micelle is stable in circulating human plasma. It is to be understood that stability of the micelle is not limited to designated pH, but that it is stable at pH values that include, at a minimum, the designated pH. In specific embodiments, a micelle described herein is substantially less stable at an acidic pH than at a pH that is about neutral. In more specific embodiments, a micelle described herein is substantially less stable at a pH of about 5.8 than at a pH of about 7.4.

In specific embodiments, the micelle is stable at a concentration of about 10 µg/mL, or greater (e.g., at about a neutral pH). In some embodiments, the micelle is stable at a concentration of about 100 µg/mL, or greater (e.g., at about a neutral pH).

In one embodiment, the micelle is a heterogeneous polymeric micelle comprising a block copolymer of the present invention and at least one additional compositionally distinct polymer. Other compositionally distinct polymers include, for example, other block copolymers comprising a hydrophilic block and a hydrophobic block. Advantageously, the hydrophobic block of the other block copolymer(s) can associate with the hydrophobic block of the copolymer of the present invention through hydrophobic interactions to form a hydrophobic core. Preferably the heterogeneous micelle is stable in aqueous medium at a physiologically relevant pH (e.g., pH 7.4). In some embodiments, the heterogeneous polymeric micelle comprises one or more additional compositionally distinct polymers, such as a third polymer that is compositionally distinct from each of the first polymer and the second polymer. Generally, each block of a block copolymer (e.g., of the first polymer and/or the second polymer) can be a homopolymer or a random copolymer, in each case linear or non linear (e.g., branched), and in each case crosslinked or uncrosslinked, and can generally comprise one or more monomeric residues derived from polymerization of a polymerizable monomer (e.g., using controlled living radical polymerization approaches)

Targeting

In certain embodiments, polymers or micelles described herein comprise at least one targeting moiety (e.g., a moiety that targets a specific cell or type of cell). In specific instances, the polymers and micelles provided herein are useful for delivery of therapeutic agents to specifically targeted cells of an individual. In certain instances, the efficiency of the cell uptake of the polymers or the micelles is enhanced by incorporation of targeting moieties into the polymers or micelles, or into or on the surface of the micelles. A "targeting moiety" (used interchangeably with "targeting agent") recognizes the surface of a cell (e.g., a select cell). In some embodiments, targeting moieties recognize a cell surface antigen or bind to a receptor on the surface of the target cell. In certain other embodiments, the polymers or micelles described herein comprise a plurality of second monomeric units in addition to a plurality of targeting moiety-bearing monomeric units, wherein the second monomeric unit serves as a spacer unit affording groups of targeting moieties spatially positioned to maximize their binding to a multivalent receptor or target. Suitable targeting moieties include, by way of non-limiting example, antibodies, antibody-like molecules, or peptides, such as an integrin-binding peptides such as RGD-containing peptides, or small molecules, such as vitamins, e.g., folate, sugars such as lactose, galactose, N-acetyl galactose amine or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting moieties of the micelles provided herein include, but are not limited to, the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, and the asialoglycoprotein receptor.

Targeting moieties (with or without spacer units) are attached, in various embodiments, to either end of a polymer (e.g., block copolymer) of the micelle, or to a side chain of a monomeric unit, or incorporated into a polymer block. Attachment of the targeting moiety to the polymer is achieved in any suitable manner, e.g., by any one of a number of conjugation chemistry approaches including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the targeting ligand to the block copolymers forming the micelles provided herein (for example of "click" reactions, see Wu, P.; Fokin, V. V. Catalytic Azide-Alkyne Cycloaddition: Reactivity and Applications. *Aldrichim. Acta* 2007, 40, 7-17). A large variety of conjugation chemistries are optionally utilized (see, for example, *Bioconjugation*, Aslam and Dent, Eds, Macmillan, 1998 and chapters therein, and Hermanson, G. T. (2008). Bioconjugate Techniques: $2^{nd}$ Edition. New York: Academic Press). In some embodiments the linker is physiologically labile or contains a physiologically labile bond.

In some embodiments, targeting ligands are attached to a monomer and the resulting compound is then used in the polymerization synthesis of a polymer described herein (e.g., block copolymer) utilized in a micelle described herein. In certain embodiments, the monomers bearing such targeting ligands are vinylic monomers. In some instances, the monomers bearing such targeting ligands have the following Formula VII:

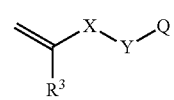

(VII)

In certain embodiments:

X is selected from a group consisting of a covalent bond —C(O)O—, —C(O)NH—, a divalent $C_5$-$C_{10}$ aryl, and a divalent $C_2$-$C_{10}$ heteroaryl, Y is a covalent bond or a linking group selected from optionally substituted divalent $C_1$-$C_{20}$ alkyl, optionally substituted divalent $C_1$-$C_{20}$ heteroalkyl, optionally substituted divalent $C_1$-$C_{20}$ alkenyl, optionally divalent substituted $C_1$-$C_{20}$ alkynyl, optionally substituted divalent $C_3$-$C_{20}$ cycloalkyl, optionally substituted divalent $C_1$-$C_{20}$ cycloheteroalkyl, optionally substituted divalent $C_5$-$C_{10}$ aryl, or optionally substituted divalent $C_3$-$C_{10}$ heteroaryl, $R^3$ is selected from the group consisting of hydrogen and optionally substituted $C_1$-$C_4$ alkyl, Q is the targeting group selected from the group comprising a sugar residue, a peptide, a vitamin, or a small molecule (MW of less than 1.5 KDa) having an affinity for a cell-surface receptor or antigen.

In some embodiments, targeting moieties are attached to a block of a first block copolymer, or to a block of a second block copolymer in a mixed micelle. In some embodiments, the targeting ligand is attached to the sense or antisense strand of siRNA bound to a polymer or a polymer of the micelle. In certain embodiments, the targeting agent is attached to a 5' or a 3' end of the sense or the antisense strand.

In certain embodiments, polymers or micelles described herein comprise at least one targeting moiety at the alpha end of the polymer. In certain embodiments, targeting groups can be included at the alpha end of the polymer by the construction of a CTA (chain transfer agent) that incorporates the targeting group(s). In certain other embodiments, the incorporated targeting group(s) is tethered away from the reactive center of the CTA via a linker group, for example, a polyethylene glycol. In certain other embodiments, a CTA comprising a folic acid residue is used as the RAFT CTA for the preparation of polymers described herein. Alternatively, targeting groups can be included at the alpha end of the polymer by the modification of a chemical group on a macro-CTA with a moiety possessing a targeting group, for example by, but not limited to, the reaction of a carboxylic acid on the macro CTA with an alcohol possessing a targeting group.

In certain embodiments, polymers or micelles described herein comprise at least one targeting moiety at the omega end of the polymer. In certain embodiments, targeting groups can be included at the omega end of the polymer by synthesis of an additional polymer block, the additional block polymerized with a vinyl monomer possessing the targeting group. In certain other embodiments, targeting groups can be included at the omega end of the polymer by synthesis of an additional polymer block, the additional block polymerized with a vinyl monomer for attaching the targeting group. In certain other embodiments, targeting groups can be included at the omega end of the polymer by synthesis of an additional polymer block, the additional block polymerized with a vinyl monomer possessing the targeting group. In certain other embodiments, the polymerization is terminated by the addition of a maleimido monomer, wherein the maleimido monomer incorporates the targeting group(s). In certain other embodiments, the polymerization is terminated by the addition of a maleimido monomer, wherein the maleimido monomer incorporates functionality for attaching the targeting group(s) for example as described by Henry et al (End-Functionalized Polymers and Junction-Functionalized Diblock Copolymers Via RAFT Chain Extension with Maleimido Monomers. Scott M. Henry, Anthony J. Convertine, Danielle S. W. Benoit, Allan S. Hoffman and Patrick S. Stayton. *Bioconjugate Chem.*, 2009, 20 (6), pp 1122-1128). In yet other embodiments, targeting groups can be included at the omega end of the polymer by synthetic modification of the Z group on the macro CTA, for example, reduction of a trithiocarbonyl group to a thiol group, followed to conjugation of the targeting group to the thiol on the polymer.

In certain embodiments, a micelle or polymer described herein comprises a mechanism for targeting the polymer, micelle, or therapeutic agent for a selected cell. In some embodiments, targeting of the polymer, micelle, or therapeutic agent is achieved by providing a copolymer described herein, or a micelle comprising such a copolymer, comprising a targeting moiety. In some embodiments, the targeting moiety is a ligand having affinity for one or more receptors effective for mediating endocytosis. In specific embodiments, the targeting moiety is covalently coupled to the first block.

Membrane Destabilization

In some embodiments, a polymer or micelle described herein (including portions, such as polymer subunits, thereof) is membrane-destabilizing at a pH of about 6.5 or lower, preferably at a pH ranging from about 5.0 to about 6.5, or at a pH of about 6.2 or lower, preferably at a pH ranging from about 5.0 to about 6.2, or at a pH of about 6.0 or lower, preferably at a pH ranging from about 5.0 to about 6.0. For example, in one embodiment, the polymer or micelle is membrane-destabilizing at a pH of or less than about 6.2, of or less than about 6.5, of or less than about 6.8, of or less than about 7.0. In certain embodiments, membrane destabilization is of any cellular membrane such as, by way of non-limiting example, an extracellular membrane, an intracellular membrane, a vesicle, an organelle, an endosome, a liposome, or a red blood cell. In some embodiments, membrane destabilizing polymers (e.g., copolymers) or membrane destabilizing block copolymers provided herein are membrane destabilizing (e.g., in an aqueous medium) at an endosomal pH.

In some embodiments, a polymer or micelle described herein (including portions, such as polymer subunits, thereof) is hemolytic at pH of or less than about 6.2, of or less than about 6.5, of or less than about 6.8, of or less than about 7.0. In further or alternative embodiments, the polymer or micelle (including portions, such as polymer subunits, thereof) is substantially non-hemolytic at pH greater than about 7.0. In specific embodiments, a polymer or micelle (including portions, such as polymer subunits, thereof) described herein is hemolytic at given concentration and a pH of about 6.2, and substantially non-hemolytic at the same concentration and at a pH greater than about 7.0. In more specific embodiments, the concentration is between 2 and 18 ug/mL, where there is 50-100% hemolysis at pH 5.8 and little or no significant hemolysis at pH 7.4. In certain embodiments, the hemolytic nature of a polymer or micelle (including portions, such as polymer subunits, thereof) described herein is determined in any suitable manner, e.g., by use of any standard hemolysis assay, such as an in vitro hemolysis assay.

In certain embodiments, a polymer or micelle described herein (including portions, such as polymer subunits, thereof) is endosome disruptive. In some embodiments, a polymer or micelle described herein (including portions, such as polymer subunits, thereof) is endosome disruptive at pH of or less than about 6.2, of or less than about 6.5, of or less than about 6.8, of or less than about 7.0. In certain embodiments, a polymer In certain embodiments, the endosome disruptive nature of a polymer or micelle (including portions, such as polymer subunits, thereof) described herein is determined in any suitable manner, e.g., by use of any standard hemolysis assay, such as an in vitro endosomolysis assay, or an in vivo non-human mammal endosomolysis assay.

Therapeutic Agents

Provided in certain embodiments is a polymer or micelle, as described herein in combination with a therapeutic agent. In specific embodiments, the therapeutic agent is a polynucleotide (e.g., oligonucleotide) or a peptide. The therapeutic agent may be used prophylactically, as a vaccine or to treat a medical condition. In some embodiments, the therapeutic agent is ionically associated and/or bioconjugated with the intermediate or second block of a copolymer described herein.

In various embodiments, research reagents, diagnostic agents, and/or therapeutic agents are attached to the block copolymer or a micelle containing the block copolymers in any suitable manner. In specific embodiments, attachment is achieved through covalent bonds, non-covalent interactions, static interactions, hydrophobic interactions, or the like, or combinations thereof. In some embodiments, the research reagents, diagnostic agents, and/or therapeutic agents are attached to an intermediate or second block of block copolymers, or micelles thereof. In certain embodiments, the research reagents, diagnostic agents, or therapeutic agents form the intermediate or second block of a block copolymer, or micelle thereof. In some embodiments, the research reagents, diagnostic agents, or therapeutic agents are in the shell of the micelle.

In some embodiments, provided herein is a micelle comprising a first therapeutic agent in the shell of the micelle and a second therapeutic agent in the core of the micelle. In specific embodiments, the first therapeutic agent is a polynucleotide. And the second therapeutic agent is a hydrophobic drug. In certain embodiments, provided herein is a micelle comprising a hydrophobic drug (e.g., small molecule hydrophobic drug) in the core of the micelle.

In certain embodiments, provided herein is a micelle comprising at least 1-5, 5-250, 5-1000, 250-1000, at least 2, at least 5, at least 10, at least 20, or at least 50 polymers with attached therapeutic agents. In some embodiments, provided herein is a composition comprising a plurality of micelles described herein, wherein the micelles therein comprise, on average, at least 1-5, 5-250, 5-1000, 250-1000, at least 2, at least 5, at least 10, at least 20, or at least 50 polymers with attached therapeutic agents.

In some embodiments, therapeutic agents, diagnostic agents, etc., are selected from, by way of non-limiting example, at least one nucleotide (e.g., a polynucleotide), at least one carbohydrate or at least one amino acid (e.g., a peptide). In specific embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other specific embodiments, the therapeutic agent is an aiRNA (Asymmetric RNA duplexes mediate RNA interference in mammalian cells. Xiangao Sun, Harry A Rogoff, Chiang J Li *Nature Biotechnology* 26, 1379-1382 (2008)). In certain embodiments, the therapeutic agent is a protein, peptide, enzyme, antibody, or antibody fragment. In some embodiments, the therapeutic agent is a carbohydrate, or a small molecule with a molecular weight of greater than about 500 Daltons.

In some embodiments, a polynucleotide associated with a polymer or micelle described herein is an oligonucleotide gene expression modulator. In certain embodiments, the polynucleotide is an oligonucleotide aptamer. In some embodiments, the polynucleotide is an oligonucleotide knockdown agent. In certain embodiments, the polynucleotide is an interfering RNA. In some embodiments, the polynucleotide is an oligonucleotide selected from an siRNA, an antisense oligonucleotide, a dicer substrate, an miRNA, an aiRNA or an shRNA. In specific embodiments, the polynucleotide is a siRNA.

In some embodiments, the therapeutic agent (e.g., oligonucleotide) comprises at least one negative charge (e.g., comprises a negatively charged backbone) and is associated with an intermediate or second block of a polymer (e.g., in a micelle). In specific embodiments, the intermediate or second block at least partially neutralizes the negative charges present in the one or more therapeutic agents (e.g., oligonucleotides) attached to or present in the polymer or a micelle comprising the polymer. In certain embodiments, one or more therapeutic agent (e.g., one or more oligonucleotide, one or more siRNA, or a combination thereof) forms an association (e.g., a complex) with the polycationic intermediate or second blocks of the micelle. In some embodiments, the association (e.g., complex) between the polymer or the micelle and therapeutic agent (e.g., oligonucleotide or siRNA) forms at any desired charge ratio of block copolymer to therapeutic agent (e.g., oligonucleotide or siRNA), e.g., between 1:1 and 16:1. In specific embodiments, the complex between the micelle and siRNA forms at the charge ratio of 2:1, 4:1 or 8:1. In other words, in some embodiments, the ratio of the number of cationic charges present in the intermediate layer of the micelle formed by the intermediate blocks of the polymers described herein to the number of anionic charges present in the therapeutic agent is any desired value, e.g., about 1:1 to about 16:1, about 2:1 to about 8:1, about 4:1 to about 12:1, about 2:1, about 4:1, or about 8:1. In some embodiments, siRNA is charge-neutralized by a polycationic intermediate block of a block copolymer forming the micelle. For example, in some specific embodiments, a 20-base pair polynucleotide (e.g., oligonucleotide or siRNA) comprising 40 negative charges at physiologic pH is associated (e.g., complexed) with a micelle comprising a polyDMAEMA intermediate or second block (80 monomeric units in length, MW=11,680) with a pKa of about 7.4. At this pH, polyDMAEMA contains 40 negative charges, thereby resulting in a polynucleotide-intermediate block association (e.g., complex) that is substantially net neutral in charge. In certain instances, avoiding a large number of excess positive charges helps to reduce in vitro and in vivo toxicity. In some embodiments, a therapeutic agent (e.g., oligonucleotide or siRNA) spontaneously associates with a positively charged shell of a micelle provided herein.

In some embodiments, a therapeutic agent (e.g., oligonucleotide) is chemically conjugated to the polymer or to the micelle and/or to one or more polymer of the micelle by any suitable chemical conjugation technique. In some embodiments, micelles containing an RNAi agent are formed by conjugation of the RNAi agent with an already formed micelle comprising a plurality of polymers (e.g., block copolymers). In other embodiments, micelles containing an RNAi agent are formed by conjugation of the RNAi agent with a polymer (e.g., a membrane destabilizing block copolymer) and subsequently forming the micelle in any suitable manner, e.g., by self assembly of the resulting conjugates into a micelle comprising the RNAi agent. In various embodiments, such a micelle optionally further comprises unconjugated polymers (e.g., block copolymers) that are similar, identical, or different than those conjugated to the RNAi agent. The covalent bond between a polymer and a therapeutic agent of a micelle described herein is, optionally, non-cleavable, or cleavable. In certain embodiments, a precursor of one or more RNAi agent (e.g. a dicer substrate) is attached to the micelle or to the polymeric units of the micelle by a non-cleavable bond. In some embodiments, one or more RNAi agent is attached through a cleavable bond. In certain embodiments, the cleavable bonds utilized in the micelles described herein include, by way of non-limiting example, disulfide bonds (e.g., disulfide bonds that dissociate in the reducing environment of the cytoplasm). In some embodiments, covalent association between a micelle (including the components thereof) and a therapeutic agent (e.g., an oligonucleotide or siRNA) is achieved through any suitable chemical conjugation method, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, *Bioconjugation, Aslam and Dent, Eds, Macmillan*, 1998 and chapters therein).

In specific embodiments, the agent delivered by the means of the polymer or the micelle provided herein is a diagnostic agent. In some embodiments, the diagnostic agent is a diagnostic imaging agent, e.g., an agent useful in imaging the mammalian vascular system which includes but is not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, or their complexes, chelates, adducts and conjugates. In other embodiments, the diagnostic agent is a marker gene that encode proteins that are readily detectable when expressed in a cell (including, but not limited to, β-galactosidase, green fluorescent protein, luciferase, and the like) and labeled nucleic acid probes (e.g., radiolabeled or fluorescently labeled probes). In some embodiments, covalent conjugation of diagnostics agents to the polymers or the micelles provided herein is achieved according to a variety of conjugation processes. In other embodiments, the diagnostic agent is non-covalently associated with the polymer or the micelle provided herein by complexing with a chelating residue (e.g., a carboxylic acid residue) incorporated into the block copolymer. In some embodiments, a radiolabeled monomer (e.g., a $^{14}$C-labeled monomer) is incorporated into the polymeric backbone of the micelle (e.g., the intermediate or second block). In some embodiments, a polymer or a micelle associated with a diagnostic agent comprises a targeting moiety.

Method for Preparing Micelle Composition

Provided in certain embodiments herein is a method for preparing a composition comprising a heterogeneous polymeric micelle and a polynucleotide associated with the micelle, the method comprising
 a. providing the block copolymer in a first denaturing medium, the block copolymer comprising a hydrophilic block and a hydrophobic block,
 b. exposing the block copolymer to a second aqueous medium,
 c. allowing the hydrophobic blocks of block copolymer to associate in the aqueous medium to form a micelle comprising the block copolymer, and
 d. associating a polynucleotide with the second block of the block copolymer.

In some embodiments, the method further comprises allowing the polynucleotide to form an ionic complex with the hydrophilic block of the first polymer. In certain embodiments, the method further comprises covalently coupling the polynucleotide, through a linking moiety, to the second block to a junction moiety between the second block and the first block or the third block. Also provided herein is a composition prepared according to such a method.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Pharmaceutical Compositions

The compositions comprising a polymer or a polymeric micelle and an agent, such as a biomolecular agent (e.g., a polynucleotide), can be a pharmaceutical composition. Such pharmaceutical composition can comprise, for example, a polymer or a polymeric micelle, a biomolecular agent, such as a polynucleotide, and a pharmaceutically acceptable excipient.

Polymer and micelle compositions provided herein (e.g., those attached to one or more RNAi agent therapeutic agent, such as one or more oligonucleotide) are optionally provided in a composition (e.g., pharmaceutically acceptable composition). In some embodiments, a polymer or micelle composition provided herein is administered to a patient in any suitable manner, e.g., with or without stabilizers, buffers, and the like, to form a pharmaceutical composition. In some embodiments, the polymer or micelle composition provided herein is formulated and used as tablets, capsules or elixirs for oral administration, suppositories for rectal administration, sterile solutions, suspensions or solutions for injectable administration, and any other suitable compositions.

Provided are pharmaceutically acceptable formulations of a polymer or micelle composition comprising at least one RNAi therapeutic agent described herein. These formulations include salts of the above compounds, e.g., acid addition salts, e.g., salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, e.g., oral, transdermal, or by injection. Thus, in specific embodiments wherein the polymer or micelle composition comprises and is delivering a polynucleotide, the formulation is in a form that does not prevent the polymer or micelle composition and, more specifically, the polynucleotide (e.g., oligonucleotide or siRNA) from reaching a target cell with the polynucleotide intact and/or functional. For example, in certain embodiments, pharmacological compositions injected into the blood stream are soluble and/or dispersible. Moreover, pharmaceutical compositions described herein are, preferably, non-toxic. In some embodiments, wherein a polymer or micelle composition provided herein is administered for therapeutic benefit, a therapeutic effective amount of the composition comprising an RNAi therapeutic agent (e.g., a polynucleotide, such as an siRNA) is administered. In an exemplary embodiment, a therapeutically effective amount includes a sufficient amount of a polymer or micelle composition provided herein to provide about 10 mg or less of siRNA per kg of individual.

In some embodiments, pharmaceutical compositions comprising a polymer or micelle composition, which comprise an RNAi therapeutic agent (e.g., a polynucleotide, such as an siRNA), are administered systemically. As used herein, "systemic administration" means in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. In some embodiments, the compositions are administered topically.

In some embodiments, the compositions are prepared for storage or administration and include a pharmaceutically effective amount of the therapeutic agent comprising a polymer or micelle composition provided herein in a pharmaceutically acceptable carrier or diluent. Any acceptable carriers or diluents are optionally utilized herein. Specific carriers and diluents and are described, e.g., in Remington's Pharmaceutical Sciences, Mack Publishing Co., A. R. Gennaro Ed., 1985. For example, preservatives, stabilizers, dyes and flavoring agents are optionally added. These include sodium benzoate, sorbic acid and esters of p-hydroxybenzoic acid. In addition, antioxidants and suspending agents are optionally used. As used herein, the term "pharmaceutically acceptable carrier" means a non-toxic, inert solid, semi-solid or liquid filler, diluent, encapsulating material or formulation auxiliary of any type. Some examples of materials optionally used as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, the pharmaceutical compositions provided herein are administered to humans and/or to animals, orally, rectally, parenterally, intracisternally, intravaginally, intranasally, intraperitoneally, topically (as by powders, creams, ointments, or drops), bucally, or as an oral or nasal spray.

In various embodiments, liquid dosage forms for oral administration include pharmaceutically acceptable emulsions, microemulsions, solutions, suspensions, syrups, and elixirs. In addition to the active ingredients (i.e., micelle-oligonucleotide complexes provided herein), the liquid dosage forms optionally further contain inert diluents or excipients, such as by way of non-limiting example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions optionally also include adjuvants such as wetting agents, emulsifying and suspending agents, sweetening, flavoring, and perfuming agents.

In some embodiments, injectable preparations, for example, sterile injectable aqueous or oleaginous suspensions are formulated according in any suitable manner, e.g., using dispersing agents, wetting agents and/or suspending agents. The sterile injectable preparation is, optionally, a sterile injectable solution, suspension, or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil is optionally employed including synthetic mono- or diglycerides. In additional embodiments, fatty acids such as oleic acid are used in the preparation of injectables. In a specific embodiment, the polymer or micelle composition provided herein is solubilized in a carrier fluid comprising 1% (w/v) sodium carboxymethyl cellulose and 0.1% (v/v) Tween 80.

In some embodiments, the injectable formulations are sterilized, for example, by filtration through a bacteria-retaining filter, or by incorporating sterilizing agents in the form of sterile solid compositions which are optionally dissolved or dispersed in sterile water or other sterile injectable medium prior to use.

In certain embodiments, compositions for rectal or vaginal administration are suppositories. Suppositories are optionally prepared by mixing the therapeutic agent comprising a polymer or micelle composition provided herein with suitable non-irritating excipients or carriers such as cocoa butter, polyethylene glycol, or a suppository wax which are solid at ambient temperature but liquid at body temperature and therefore melt in the rectum or vaginal cavity and release a polymer or micelle composition provided herein.

Suitable solid dosage forms for oral administration include, by way of non-limiting example, capsules, tablets, pills, powders, and granules. In such solid dosage forms, a polymer or micelle composition provided herein comprising an RNAi therapeutic agent (e.g., oligonucleotide) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type are also optionally employed as fillers in soft and hard-filled gelatin capsules using such excipients as lactose or milk sugar as well as high molecular weight polyethylene glycols and the like.

In some embodiments, the solid dosage forms of tablets, dragees, capsules, pills, and granules are prepared with coatings and shells such as enteric coatings and other suitable coatings. They optionally contain opacifying agents. In certain embodiments, they are of a composition that they release the active ingredient(s) only, or preferentially, in a certain part of the intestinal tract, optionally, in a delayed manner. Examples of suitable embedding compositions include, by way of non-limiting example, polymeric substances and waxes.

Solid compositions of a similar type are optionally employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include, by way of non-limiting example, ointments, pastes, creams, lotions, gels, powders, solutions, sprays, inhalants, or patches. In some embodiments, therapeutic agents comprising a polymer or micelle composition provided herein are admixed under sterile conditions with a pharmaceutically acceptable carrier and, optionally, one or more preservative, one or more buffer, or a combination thereof (e.g., as may be required). Ophthalmic formulation, ear drops, and eye drops are also contemplated as being within the scope of this invention.

Ointments, pastes, creams, and gels provided herein optionally contain, in addition to the polymer or micelle composition provided herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays optionally contain, in addition to a polymer or micelle composition provided herein, excipients such as lactose, talc, silicic acid, aluminum hydroxide, calcium silicates, and polyamide powder, or mixtures of these substances. In some embodiments, sprays additionally contain customary propellants such as chlorofluorohydrocarbons.

Transdermal patches have the added advantage of providing controlled delivery of a compound to the body. Such dosage forms are made in any suitable manner, e.g., by dissolving or dispensing the microparticles or nanoparticles in a proper medium. Absorption enhancers are optionally used to increase the flux of the compound across the skin. The rate can be controlled by either providing a rate controlling membrane or by dispersing a polymer or micelle composition provided herein in a polymer matrix or gel.

In some aspects of the invention, a polymer or micelle composition provides some properties (e.g. mechanical, thermal, etc.) that are usually performed by excipients, thus decreasing the amount of such excipients required for the formulation.

Therapeutic Uses

Compositions comprising polymers or polymeric micelles and an agent such as a polynucleotide can be used in various methods.

Generally, such compositions can be used for example in a method for intracellular delivery of an agent such as a polynucleotide. The composition comprising a polymer or a polymeric micelle and an agent (e.g., a polynucleotide) associated therewith can be exposed to and contacted with a with a cell surface (e.g., via directed targeting) in a medium at a first pH. The composition is introduced into an endosomal membrane within the cell, for example, through endocytosis and, in some embodiments, through receptor mediated endocytosis. The endosomal membrane is destabilized (e.g., by a constituent polymer or block thereof, which is a membrane destabilizing polymer), thereby delivering the composition or the agent (e.g., polynucleotide) to the cytosol of the cell. The medium can be an in vitro medium. The medium can be an in vitro medium such as a physiological medium.

Generally, for example, such compositions can be used for modulating the activity of an intracellular target in a cell. The agent, such as a polynucleotide, can be delivered to the cytosol of a cell according to the method described in the immediately preceding paragraph. The agent (e.g., polynucleotide) is allowed to interact with the intracellular target, thereby modulating the activity of the intracellular target.

More specifically, for example, in some embodiments, the compositions comprising polymers or polymeric micelles (e.g., micelles) provided herein are useful in treating a subject at risk for or afflicted with disorders associated with and/or caused by high plasma levels or cholesterol, apolipoprotein b, and/or LDL cholesterol, e.g., hypercholesterolemia. In certain embodiments, the treatment comprises providing a polymeric micelle and a therapeutic agent (e.g., an oligonucleotide agent) associated therewith, wherein the therapeutic agent silences (e.g., by cleavage) a gene, or a gene product that promotes such condition. In some embodiments the therapeutic agent (e.g., an oligonucleotide or RNAi agent) silences proprotein convertase subtilisin/kexin type 9 (PCSK9) gene responsible for regulation of low density lipoprotein (LDLR) levels and function and, thus, polymers or polymeric micelles comprising such therapeutic agents are used to treat a subject having or at risk for a disorder characterized by unwanted PCSK9 expression, e.g., disorders associated with and/or caused by high plasma levels or cholesterol, apolipoprotein b, and/or LDL cholesterol, e.g., hypercholesterolemia. In some embodiments, the polymers or polymeric micelles deliver a PCSK9 silencing polynucleotide agent (e.g., siRNA) to a cell expressing PCSK9. In some embodiments, the cell is a liver cell.

In some embodiments, the polymers or polymeric micelles (e.g., micelles) provided herein are useful in treating a subject at risk for or afflicted with unwanted cell proliferation (e.g., malignant or nonmalignant cell proliferation). The treatment comprises providing a composition comprising a polymer or a polymeric micelle and a therapeutic agent (e.g., an oligonucleotide agent), wherein the therapeutic agent can silence (e.g., by cleavage) a gene or a gene product that promotes unwanted cell proliferation; and administering a therapeutically effective dose of the polymer or polymeric micelle to a subject (e.g., a human subject.). In some embodiments, the therapeutic agent is a polynucleotide (e.g., an oligonucleotide) that is homologous to and can silence (e.g., by cleavage) a gene.

In certain embodiments, the gene is, but is not limited to, a growth factor or growth factor receptor gene, a phosphatase, a kinase, e.g., a protein tyrosine, serine, or threonine kinase gene, an adaptor protein gene, a gene encoding a G protein superfamily molecule, or a gene encoding a transcription factor. In some instances, the composition comprises a polymer or a polymeric micelle and a polynucleotide that silences a gene that is expressed in a specific tissue or organ including, but not limited to, lung, pancreas, liver, kidney, ovary, muscle, skin, breast, colon, stomach, and the like.

In some embodiments, the oligonucleotide agent silences one or more of the following genes the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers and chronic leukemia; the MEKK gene, and thus can be used to treat a subject having or at risk for a disorder characterized by unwanted MEKK expression, e.g., squamous cell carcinoma, melanoma, or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA(p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL 2 gene, and thus can be used to treat a subject having or at risk for a disorder characterized by unwanted BCL-2 expression, e.g., lung or prostate cancers or Non Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-1 gene, and thus can be used to treat a subject having or at risk for a disorder characterized by unwanted WNT 1 expression, e.g., basal cell carcinoma; the beta catenin gene, and thus can be used to treat a subject having or at risk for a disorder characterized by unwanted beta catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the Topoisomerase I gene, and thus can be used to treat a subject having or at risk for a disorder characterized by unwanted Topoisomerase I expression, e.g., ovarian and colon cancers; the Topoisomerase II alpha gene, and thus can be used to treat a subject having or at risk for a disorder characterized by unwanted Topoisomerase II expression, e.g., breast and colon cancers.

In other embodiments the oligonucleotide agent silences mutations in one of the following genes: the p73 gene, and thus can be used to treat a subject having or at risk for a disorder characterized by unwanted p73 expression, e.g., colorectal adenocarcinoma; the p21(WAF1/CIP1) gene, and thus can be used to treat a subject having or at risk for a disorder characterized by unwanted p21(WAF1/CIP1) expression, e.g., liver cancer; the p27(KIP1) gene, and thus can be used to treat a subject having or at risk for a disorder characterized by unwanted p27(KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the oligonucleotide agent silences mutations in tumor suppressor genes and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN p63, the pRb tumor suppressor gene, the APC1 tumor suppressor gene, the BRCA1 tumor suppressor gene, the PTEN tumor suppressor gene.

In some embodiments the oligonucleotide agent silences one of the following fusion genes: mLL fusion genes, e.g., mLL AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEL/AML1 fusion gene, and thus can be used to treat a subject having or at risk for a disorder characterized by unwanted TEL/AML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some aspects herein the compositions comprising the polymers or polymeric micelles and an agent, such as a polynucleotide, provide therapeutic agents for treating a subject, e.g., a human, at risk for or afflicted with a disease or disorder that may benefit by angiogenesis inhibition e.g., cancer or retinal degeneration. The treatment comprises providing a polymer or a polymeric micelle comprising an oligonucleotide agent, wherein said oligonucleotide agent is homologous to and/or can silence, e.g., by cleavage, a gene that mediates angiogenesis (e.g., VEGF R1, VEGF R2, or gene encoding signaling proteins for these receptors' pathways); and administering a therapeutically effective dosage of said polymer or polymeric micelle comprising the oligonucleotide agent to a subject, e.g., a human subject.

In some embodiments the oligonucleotide agent silences one of the following genes: the alpha v integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the composition comprising polymers pr polymeric micelles and an oligonucleotide agent relate to a method of treating a subject infected with a virus or at risk for or afflicted with a disorder or disease associated with a viral infection. The method comprises providing a polymer or a polymeric micelle comprising an oligonucleotide agent, wherein said oligonucleotide agent is homologous to and/or can silence, e.g., by cleavage, a viral gene or a cellular gene that mediates viral function, e.g., entry or growth; and administering a therapeutically effective dose of said oligonucleotide agent to a subject, e.g., a human subject.

In some embodiments, the composition comprising polymers or polymeric micelles and an oligonucleotide agent are useful in treatment of subjects infected with the Human Papilloma Virus (HPV) or at risk for or afflicted with a disorder mediated by HPV, e.g., cervical cancer.

In some embodiments, a composition comprising a polymer or a polymeric micelle and an oligonucleotide agent silencing expression of a HPV gene is reduced. In some embodiments, the HPV gene is selected from the group of E2, E6, or E7.

In another embodiment the expression of a human gene that is required for HPV replication is reduced.

In some embodiments, the composition comprises a polymer or a polymeric micelle and an oligonucleotide agent useful in treating patients infected by the Human Immunodeficiency Virus (HIV) or at risk for or afflicted with a disorder mediated by HIV, e.g., Acquired Immune Deficiency Syndrome (AIDS). In some embodiments, the expression of an HIV gene is reduced. In other embodiments, the HIV gene is CCR5, Gag, or Rev. In some embodiments the expression of a human gene that is required for HIV replication is reduced. In some embodiments, the gene is CD4 or Tsg101.

In some embodiments, the composition comprises a polymer or a polymeric micelle and an oligonucleotide agent useful for treating patients infected by the Hepatitis B Virus (HBV) or at risk for or afflicted with a disorder mediated by HBV, e.g., cirrhosis and heptocellular carcinoma. In one embodiment, the expression of a HBV gene is reduced. In another embodiment, the targeted HBV gene encodes one of the groups of the tail region of the HBV core protein, the pre cregious (pre c) region, or the cregious (c) region. In other embodiments, a targeted HBV RNA sequence is comprised of the poly(A) tail. In some embodiments, the expression of a human gene that is required for HBV replication is reduced.

In some embodiments, the composition comprises a polymer or a polymeric micelle and an oligonucleotide agent useful for treating patients infected with or at risk for or afflicted with a disorder mediated by a virus selected from the following viruses: the Hepatitis A Virus (HAV); Hepatitis C Virus (HCV); any of the group of Hepatitis Viral strains comprising Hepatitis D, E, F, G, or H; the Respiratory Syncytial Virus (RSV); the herpes Cytomegalovirus (CMV); the herpes Epstein Barr Virus (EBV); Kaposi's Sarcoma associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick borne encephalitis flavivirus; the Murray Valley encephalitis flavivirus; the dengue flavivirus; the Simian Virus 40 (SV40); the encephalomyocarditis virus (EMCV); the measles virus (MV); the Varicella zoster virus (VZV); an adenovirus (e.g., virus causing a respiratory tract infection); the poliovirus; or a poxvirus (a poxvirus causing smallpox). In some embodiments, the expression of a human gene that is required for the replication of these viruses is reduced.

In some embodiments, the composition comprises a polymer or a polymeric micelle and an oligonucleotide agent useful for treating patients infected by the Herpes Simplex Virus (HSV) or at risk for or afflicted with a disorder mediated by HSV, e.g., genital herpes and cold sores, as well as life threatening or sight impairing disease, e.g., mainly in immunocompromised patients. In some embodiments, the expression of a HSV gene is reduced. In other embodiments, the targeted HSV gene encodes DNA polymerase or the helicase primase. In some embodiments the expression of a human gene that is required for HSV replication is reduced.

In some embodiments, the composition comprises a polymer or a polymeric micelle and an oligonucleotide agent useful for treating patients infected by the West Nile Virusor at risk for or afflicted with a disorder mediated by West Nile Virus. In some embodiments, the expression of a West Nile Virus gene is reduced. In other preferred embodiments, the West Nile Virus gene is selected from the group comprising E, NS3, or NS5. In some embodiments, the expression of a human gene that is required for West Nile Virus replication is reduced.

In some embodiments, the polymer or polymeric micelle comprises an oligonucleotide agent useful for treating patients infected by the Human T Cell Lymphotropic Virus (HTLV) or a disease or disorder associated with this virus, e.g., leukemia or myelopathy. In some embodiments, the expression of a HTLV gene is reduced. In some embodiments, the HTLV1 gene is the Tax transcriptional activator. In some embodiments, the expression of a human gene that is required for HTLV replication is reduced.

In some aspects, the composition comprises a polymer or a polymeric micelle and an oligonucleotide agent useful for treating a subject infected with a pathogen, e.g., a bacterial, amoebic, parasitic, or fungal pathogen. The method of treatment comprises providing a polymer or a polymeric micelle comprising an oligonucleotide agent, wherein said oligonucleotide is homologous to and/or can silence, e.g., by cleavage of a pathogen gene or a gene involved in the pathogen's growth; and administering a therapeutically effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production.

Thus, in some embodiments, the composition comprises a polymer or a polymeric micelle and an oligonucleotide agent useful for of treating patients infected by a *plasmodium* that causes malaria. In some embodiments, the expression of a *plasmodium* gene is reduced. In other embodiments, the gene is apical membrane antigen 1 (AMA1). In some embodiments, the expression of a human gene that is required for *plasmodium* replication is reduced.

In some embodiments, the polymer or polymeric micelle comprises an oligonucleotide agent useful for treating patients infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is reduced.

In some embodiments, the diseases treated by the compositions comprising a polymer or a polymeric micelle and an agent as provided herein may be systemic or present in a specific tissue, e.g., the lung, skin, liver, breast, kidney, pancreas, CNS, or the like. In certain aspects, the oligonucleotide silences a gene that mediates or is involved in a metabolic disease or disorder, e.g., diabetes, obesity, and the like. In certain embodiments, the oligonucleotide silences a gene that mediates or is involved in a pulmonary disease or disorder, e.g., chronic obstructive pulmonary disease (COPD), cystic fibrosis, or lung cancer. In some aspects herein, the polymers or polymeric micelles comprise an oligonucleotide agent useful for and/or related to a method of treating a subject, e.g., a human, at risk for or afflicted with a disease or disorder characterized by an unwanted immune response, e.g., an inflammatory disease or disorder or an autoimmune disease or disorder. The method comprises providing a polymer or a polymeric micelle comprising an oligonucleotide agent, wherein said oligonucleotide agent is homologous to and/or can silence, e.g., by cleavage, a gene that mediates an unwanted immune response; and administering said oligonucleotide agent to a subject, e.g., a human subject. In some embodiments, the disease or disorder is an ischemia or reperfusion injury, e.g., ischemia or reperfusion injury associated with acute myocardial infarction, unstable angina, cardiopulmonary bypass, surgical intervention, e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention, e.g., angioplasty, e.g., percutaneous transluminal coronary angioplasty. In other embodiments, the disease or disorder is Inflammatory Bowel Disease, e.g., Crohn's Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type II diabetes, arthritis, e.g., rheumatoid or psoriatic. In certain embodiments, the oligonucleotide agent silences an integrin or co ligand thereof, e.g., VLA4, VCAM, ICAM. In other embodiments the oligonucleotide agent silences a selectin or co ligand thereof, e.g., P selectin, E selectin (ELAM), I selectin, P selectin glycoprotein 1 (PSGL 1). In certain embodiments, the oligonucleotide agent silences a component of the complement system, e.g., C3, C5, C3aR, C5aR, C3, convertase, and C5 convertase. In some embodiments, the oligonucleotide agent silences a chemokine or receptor thereof, e.g., TNFI, TNFJ, IL 1I, IL 1J, 1L 2, IL 2R, IL 4, IL 4R, IL 5, IL 6, IL 8, TNFRI, TNFRII, IgE, SCYA11, and CCR3. In other embodiments the oligonucleotide agent silences GCSF, Gro1, Gro2, Gro3, PF4, MIG, Pro Platelet Basic Protein (PPBP), MIP 1I, MIP 1J, RANTES, MCP 1, MCP 2, MCP 3, CMBKR1, CMBKR2, CMBKR3, CMBKR5, AIF 1, or I 309.

In some aspects, the composition comprises a polymer or a polymeric micelle and an oligonucleotide agent useful for treating a subject, e.g., a human, at risk for or afflicted with a neurological disease or disorder. The method comprises providing a polymer or a polymeric micelle comprising an oligonucleotide agent, wherein said oligonucleotide is homologous to and/or can silence, e.g., by cleavage, a gene that mediates a neurological disease or disorder; and administering a therapeutically effective dose of said oligonucleotide agent to a subject, e.g., a human. In some embodiments, the disease or disorder is Alzheimer Disease or Parkinson Disease. In certain embodiments, the oligonucleotide agent silences an amyloid family gene, e.g., APP; a presenilin gene, e.g., PSEN1 and PSEN2, or I synuclein. In other embodiments, the disease or disorder is a neurodegenerative trinucleotide repeat disorder, e.g., Huntington disease, dentatorubral pallidoluysian atrophy, or a spinocerebellar ataxia, e.g., SCA1, SCA2, SCA3 (Machado Joseph disease), SCA7 or SCA8. In some embodiments, the oligonucleotide agent silences HD, DRPLA, SCA1, SCA2, MJD1, CACNL1A4, SCA7, or SCA8.

In certain aspects the composition comprises a polymer or a polymeric micelle and an oligonucleotide agent capable of cleaving or silencing more than one gene. In these embodiments, the oligonucleotide agent is selected so that it has sufficient homology to a sequence found in more than one gene, e.g., a sequence conserved between these genes. Thus in some embodiments, an oligonucleotide agent targeted to such sequences effectively silences the entire collection of genes.

The following examples provide various illustrative embodiments of the invention as well as synthesis methods and various biological and other activity parameters. The examples, however, provide details concerning only some of the embodiments of the invention and are not intended to be limiting.

EXAMPLES

Throughout the description of the present invention, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "Gal" refers to galactose or a galactose residue, optionally including hydroxyl-protecting moieties (e.g., acetyl) or to a pegylated derivative thereof; "Nag" refers to N-acetyl galactosamine or a N-Acetyl galactosamine residue, optionally including hydroxyl-protecting moieties (e.g., acetyl) or to a pegylated derivative thereof; "HPMA" represents 2-hydroxypropyl methacrylamide or monomeric residue derived therefrom; "HPMA-E" represents 2-hydroxypropyl methacrylate or monomeric residue derived therefrom; "MAA" represents methylacrylic acid or monomeric residue derived therefrom; "MAA(NHS)" represents N-hydroxyl-succinimide ester of methacrylic acid or monomeric residue derived therefrom; "FAA" (or the letter "P" as equivalent shorthand notation) represents 2-propylacrylic acid or monomeric residue derived therefrom, "PEGMA" refers to the pegylated methacrylic monomer, $CH_3O(CH_2CH_2O)_{7-8}C(O)C(CH_3)CH_2$ or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

Triblock Polymer Preparation and Characterization

In certain embodiments, provided herein are triblock copolymers represented by Formula I:

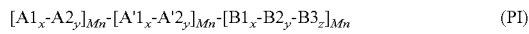

In certain embodiments, [A1-A2] is the first block copolymer, composed of monomeric residues A1 and A2, wherein A1 is a hydrophilic monomeric residue and x is >0, and [A1-A2] is overall hydrophilic. In some embodiments, [A'1-A'2] is the second block copolymer, composed of monomeric residues A'1 and A'2. In certain embodiments, [B1-B2-B3] is the 3rd block copolymer, composed of monomers B1, B2, B3. x, y, z defines the polymer composition in mole % of the individual monomers. Mn is molecular weight of each of the polymer blocks.

In specific embodiments, triblock copolymer include:

Triblock copolymers offer unique structural and functional features. In some instances, the first two blocks are typically composed of predominantly hydrophilic monomers. A first block containing PEGMA acts as a steric shield (for example, in order to reduce toxicity) of a cationic second homopolymer block, composed of, for example, DMAEMA. The first block may also contain amine reactive ester monomers, for example MAA(NHS), used for conjugation of ligands that function in cell type specific targeting. A second cationic block containing DMAEMA functions as the nucleic acid drug binding domain. Together, the first and second hydrophilic blocks comprise the outer domain and inner domain, respectively, of a hydrophilic shell. The third block contains both hydrophobic and ionizable monomers that together form a predominantly hydrophobic core that functions in intracellular endosome nucleic acid drug release. As demonstrated in the examples, the triblock copolymer, consisting of a hydrophilic shell (with inner and outer domains) and a hydrophobic core forms particles that have the properties of micelles.

Example 1

Preparation of First Block [A 1-A2] Polymer macro-CTAS: [PEGMA-MAA-NHS]-CTA

The RAFT polymerization of the first block co-polymer was typically conducted in DMF at 68° C. under a nitrogen atmosphere for 1-4 hours using 4-Cyano-4-(ethylsulfanyl-thiocarbonyl)sulfanylpentanoic acid (ECT) as the chain transfer agent (CTA), and azobisisobutyronitrile (AIBN) (Wako chemicals) as the radical initiator. The initial monomer to CTA ratio ($[CTA]_0/[M]_0$ was such that the theoretical $M_n$ at 50% conversion was the desired molecular weight (g/mol). The ratio of PEGMA and MAA(NHS) or PEGMA and DMAEMA in the first block was varied by using different feed ratios of the individual monomers, for example 70:30. The $[CTA]_0/[M]_0$ was 100:1. The initial CTA to initiator ratio ($[CTA]_0/[I]_0$) was 10 to 1. The resulting diblock copolymer macro-CTA was isolated by precipitation 4 times from acetone into hexane/Ether 75/25 and dried overnight in vacuo. Mn=11,700 KDa; PDI=1.48.

Example 2

Preparation of Second Block [A'1] Polymer DMAEMA Macro-CTAs

Figure 2:
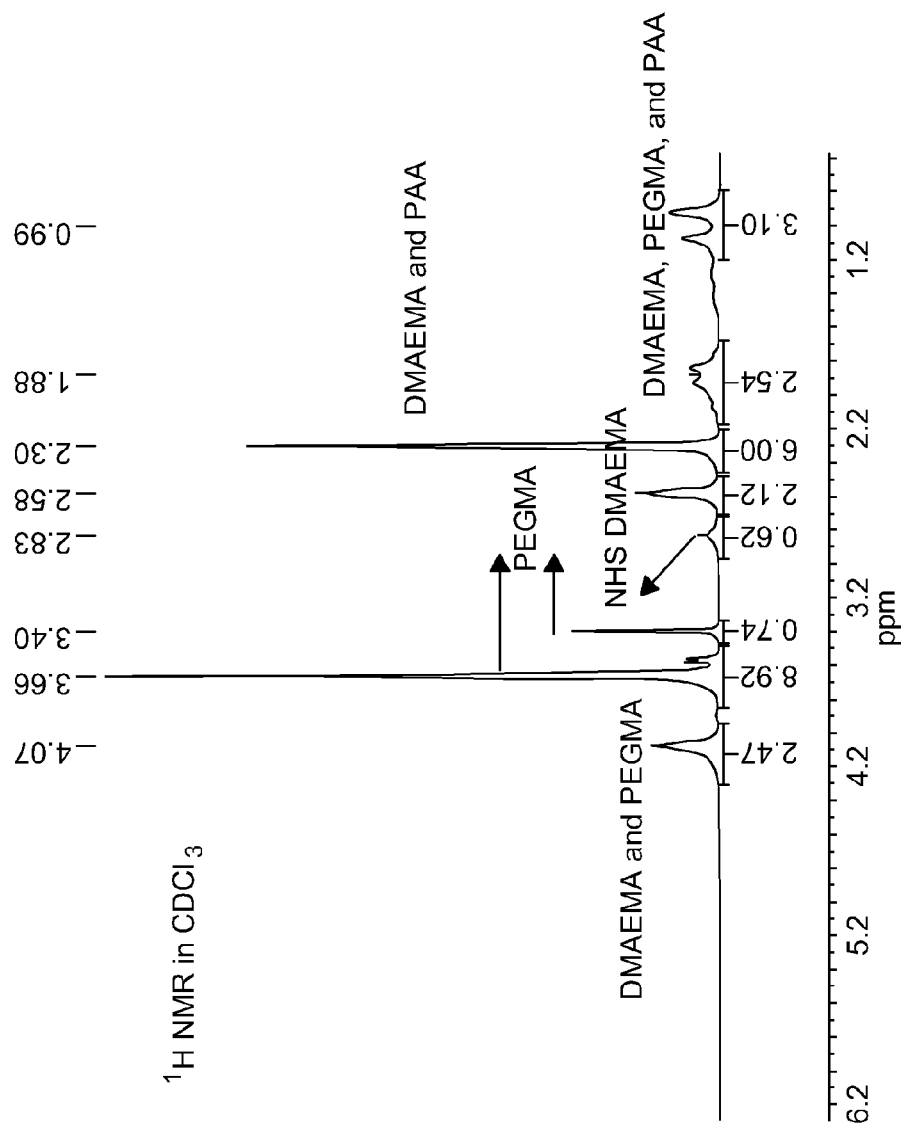
FIG. 2 illustrates characterization of poly[PEGMA-MAA(NHS)]-b-[DMAEMA] by NMR.
Figure 3:
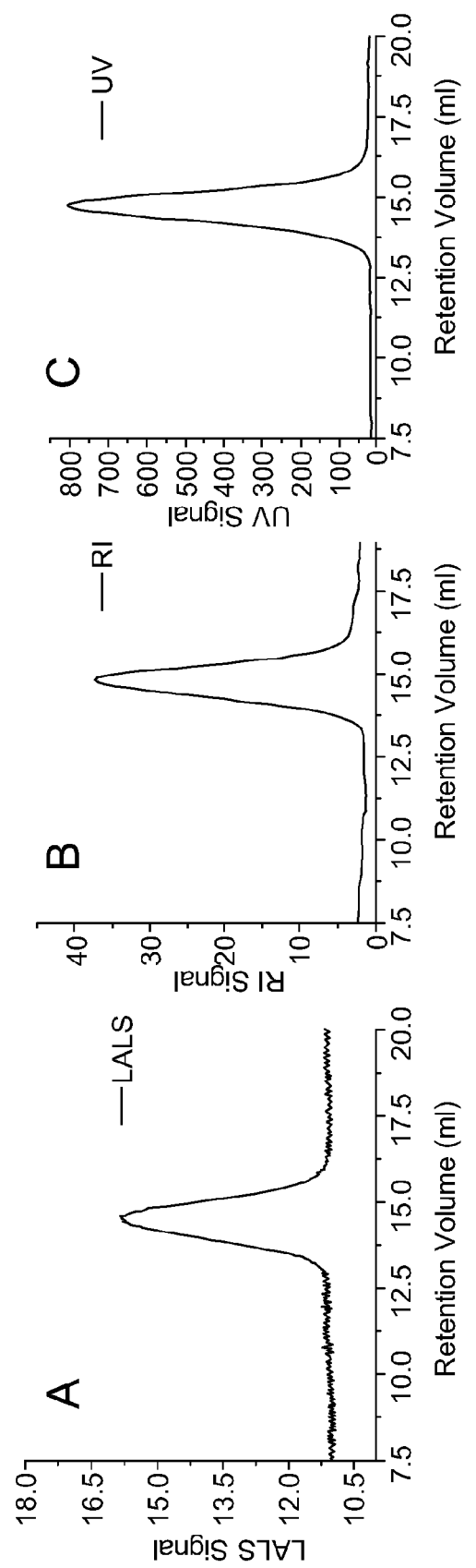
FIG. 3 illustrates characterization of poly[PEGMA-MAA(NHS)]-b-[DMAEMA] by GPC.

The RAFT polymerization and isolation of the second block homopolymer DMAEMA macro-CTAs was conducted as described in example 1 using the first block copolymer as a macro-CTA. Mn=20.5 Kda, PDI=1.2. FIG. 1 summarizes the reaction scheme for the synthesis of [PEGMA$_{70}$-MAA(NHS)$_{30}$]. NMR spectroscopy in CDCl$_3$ was used to confirm the polymer structure and calculate the composition of the $2^{nd}$ block (FIG. 2). Gel permeation chromatography (GPC) was used to determine molecular weights and polydispersities (PDI, $M_w/M_n$) of both the poly[PEGMA-MAA(NHS)]-macro-CTA and diblock copolymer samples in DMF using a Viscotek GPCmax VE2001 and refractometer VE3580 (Viscotek, Houston, Tex.). HPLC-grade DMF containing 1.0 wt % LiBr was used as the mobile phase. FIGS. 3A, 3B and 3C show the elution profiles monitoring light scattering (LAIS), refractive index (RI), and UV absorption respectively.

Example 3

Figure 4:
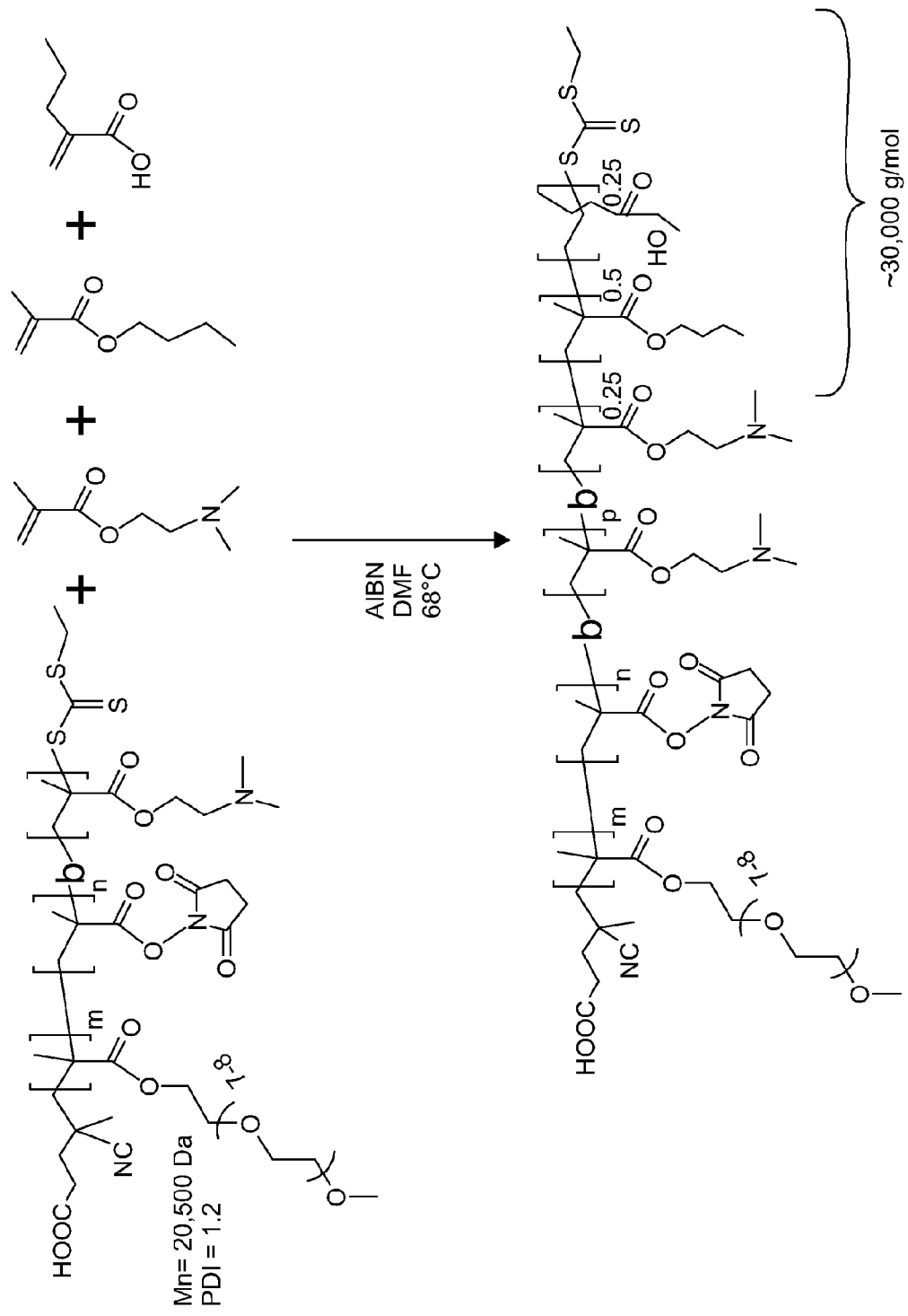
FIG. 4 illustrates the synthesis of poly[PEGMA-MAA(NHS)]-b-[DMAEMA]-b-[DMAEMA-BMA-PAA].
Figure 5:
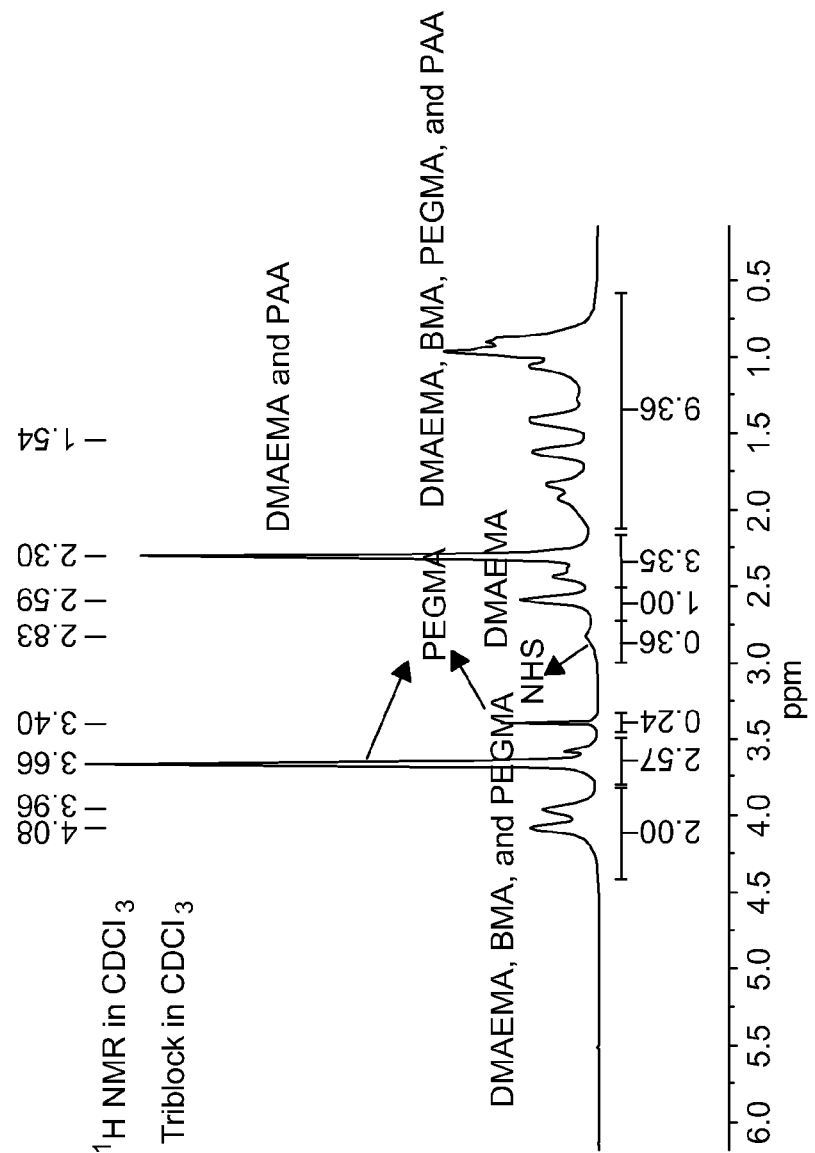
FIG. 5 illustrates the characterization of poly[PEGMA-MAA(NHS)]-b-[DMAEMA]-b-[DMAEMA-BMA-PAA] by NMR.

Preparation of Third Block (B1-B2-B3) Copolymerization of DMAEMA, PAA, and BMA from A Poly[PEGMA-MAA(NHS)]-[DMAEMA]-Diblock macroCTA The desired stoichiometric quantities of BMA, PAA, and DMAEMA (for example, 50:25:25), were added to poly [PEGMA-MAA(NHS)]-[DMAEMA]-diblock dissolved in N,N-dimethylformamide (25 wt % monomer and macroCTA to solvent). For all polymerizations $[M]_0/[CTA]_0$ and $[CTA]_0/[I]_0$ were 250:1 and 10:1 respectively. Following the addition of AIBN the solutions were purged with nitrogen for 30 min and allowed to react at 68° C. for 6-12 h (FIG. 4). The resulting triblock copolymer was isolated by precipitation 4 times from acetone into hexane/Ether 75/25 and dried overnight in vacuo. NMR spectroscopy in CDCl$_3$ was used to confirm the polymer structure and calculate the composition of the $2^{nd}$ block (FIG. 5). Gel permeation chromatography (GPC) was used to determine molecular weights and polydispersities (PDI, $M_w/M_n$) of the macroC-TAs and triblock copolymer samples in DMF using a Viscotek GPCmax VE2001 and refractometer VE3580 (Viscotek, Houston, Tex.). HPLC-grade DMF containing 1.0 wt % LiBr was used as the mobile phase. FIGS. 6A, 6B and 6C summarizes the triblock characterization and shows the elution profiles monitoring light scattering (LAIS), refractive index (RI), and UV absorption respectively. Mn=52.5 Kda, PDI=1.49.

Example 4

NMR Spectroscopy of Tri Block Copolymer [PEGMA$_{70}$-MAA(NHS)$_{30}$]-[DMAEMA]-[[B$_{50}$-P$_{25}$-D25]. (FIG. 7)

This example provides evidence, using NMR spectroscopy, that the triblock polymer forms a micelle-like structure in aqueous solution.

$^1$H NMR spectra were recorded on Bruker AV301 in deuterated chloroform (CDCl$_3$) and deuterated water (D$_2$O) at 25° C. A deuterium lock (CDCl$_3$, D$_2$O) was used, and chemical shifts were determined in ppm from tetramethylsilane (for CDCl$_3$) and 3-(trimethylsilyl)propionic-2,2,3,3-d4 acid, sodium salt (for D$_2$O). Polymer concentration was 6 mg/ml.

NMR spectroscopy of the synthesized polymer, using the triblock polymer as an example, in aqueous buffer provided evidence that the triblock polymers of the present invention form micelles in aqueous solution. Formation of micelles results in the formation of a shielded viscous internal core that restricts the motion of the protons forming the core segments and prevents deuterium exchange between the solvent and the protons of the core. This is reflected by a significance suppression or disappearance of the $^1$H NMR signals of the corresponding protons. We used this inherent property of solution NMR spectroscopy to show that the hydrophobic block of the core of the micelle is effectively shielded. If micelles are formed in aqueous media, a disappearance of the signals due to the protons of the hydrophobic copolymer block should occur.

FIG. 7 shows the $^1$H NMR experiments of triblock polymer in D$_2$O (aqueous solvent). The $^1$H NMR spectrum of polymer in CDCl$_3$ at room temperature (not shown) showed the signals attributed to all polymer protons indicating that the polymer chains remain dispersed (non-aggregated) in CDCl$_3$ and preserved their motion so their protons could exchange with the solvent. This indicated that stable micelles with shielded cores were not formed in organic solvent. FIG. 7 shows the $^1$H NMR spectra of triblock polymer in D$_2$O. The signals representing the protons of the hydrophobic block (BMA, PAA, DMAEMA) disappeared from the spectrum. This indicates that stable micelles with shielded cores were formed from triblock polymer in aqueous solution. Moreover, in the same spectrum, the signal attributed to the resonance of the protons of the two methyl groups of the DMAEMA (2.28 ppm) underwent a significant suppression, implying that only the second block poly DMAEMA of the shell was exposed to water, i.e., mainly the charged group of DMAEMA as well as all of the protons that constitute PEGMA. Taken together, the results of $^1$H NMR experiments indicate that the triblock polymer forms micelles with an ordered core-shell structure where the first block and second blocks form a hydrated outer shell surrounding a core composed of hydrophobic units (BMA) and electrostatically stabilizing units of opposite charge (PAA, DMAEMA).

Example 5

Dynamic Light Scattering (DLS) Determination of Particle Size of Triblock Polymer [PEGMA$_{70}$-MAA (NHS)$_{30}$]-[DMAEMAH]-[[B$_{50}$-P$_{25}$-D$_{25}$]. (FIG. 8)

The following example demonstrates that triblock polymer forms uniform particles 54 nm in size.

Particle sizes of triblock polymer were measured by dynamic light scattering using a Malvern Zetasizer Nano ZS. FIGS. 8A and 8B show the particle size distribution by intensity and volume respectively. Polymer was measured in phosphate buffered saline, pH 7.4 (PBS) at 1 mg/ml. Polymer showed particle sizes with a near uniform distribution, PDI 0.130.

Example 6

Synthesis of Triblock Polymers: [Gal]-[HPMA$_{90}$-PDSMA$_{10}$]-[D$_{25}$-B$_{50}$-P$_{25}$] and [Gal$_{90}$-MAA$_{10}$]-[HPMA$_{80}$-PDSMA$_{10}$-MAA$_{10}$]-[D$_{25}$-B$_{50}$-P$_{25}$]

The structure synthesized is represented by formulas (PII) and (PII.1):

$$[Gal]_{4K}\text{-}[HPMA_{90}\text{-}PDSMA_{10}]_{12.0K}\text{-}[D_{25}\text{-}B_{50}\text{-}P_{25}]_{30K} \quad (PII)$$

(PII.1)

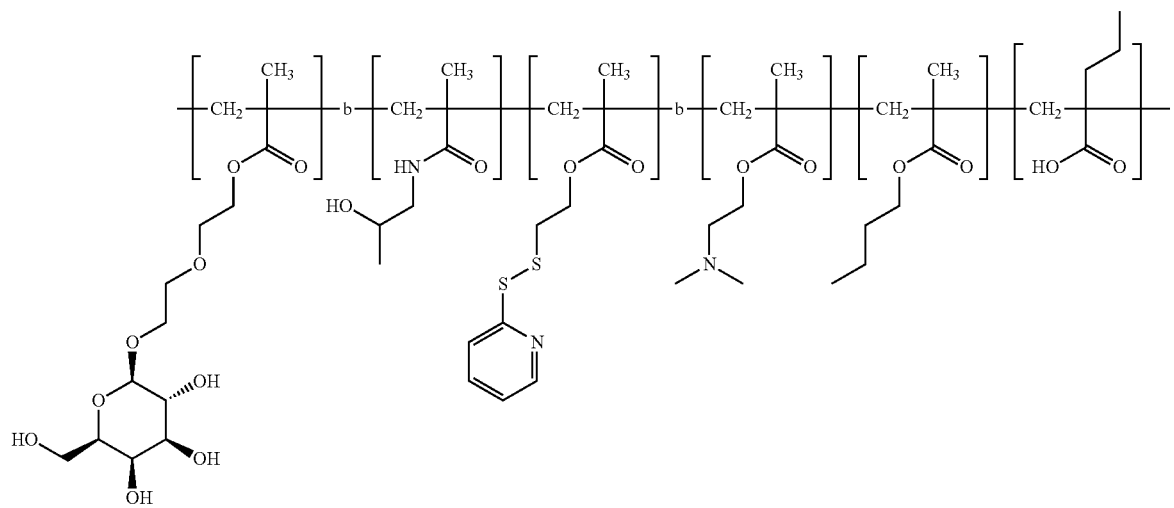

Example 6.1

Synthesis of PEG2 Vinyl Monomer

Synthesis is performed as described by Tew et al. (*Polymer*, 2008, 49, 1761-1769) with modifications, as summarized in scheme 1.

Scheme 1

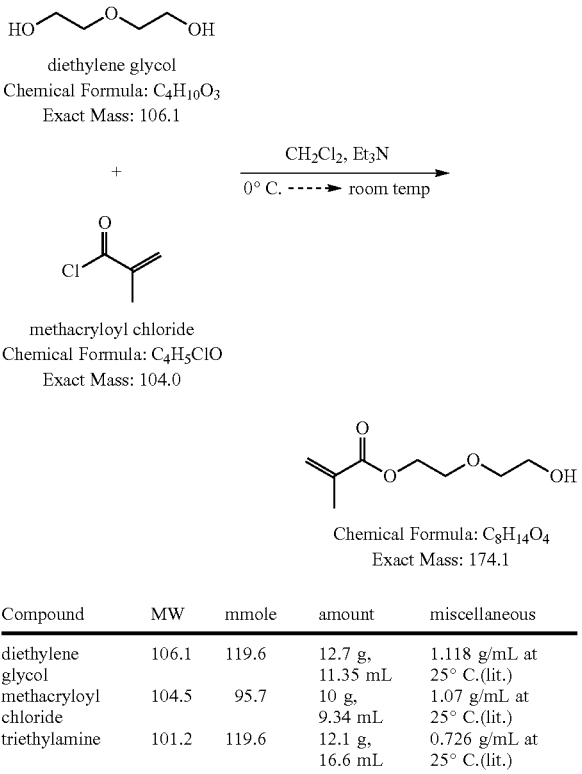

| Compound | MW | mmole | amount | miscellaneous |
|---|---|---|---|---|
| diethylene glycol | 106.1 | 119.6 | 12.7 g, 11.35 mL | 1.118 g/mL at 25° C.(lit.) |
| methacryloyl chloride | 104.5 | 95.7 | 10 g, 9.34 mL | 1.07 g/mL at 25° C.(lit.) |
| triethylamine | 101.2 | 119.6 | 12.1 g, 16.6 mL | 0.726 g/mL at 25° C.(lit.) |
| $CH_2Cl_2$ | 84.93 | — | 350 mL | bp: 39.8-40° C., mp: −97° C. |

To a round-bottom flask was added diethylene glycol (120 mmol) followed by anhydrous $CH_2Cl_2$ (330 mL), and triethylamine (120 mmol). This mixture was stirred at 0° C. for 5 min under a flow of argon gas. To a 25 mL addition funnel was added anhydrous $CH_2Cl_2$ (10 mL) and methacryloyl chloride (9.3 mL, 96 mmol). The methacryloyl chloride solution was then added drop wise into the cooled reaction solution over 30 min. After the addition was complete the homogeneous mixture was stirred at 0° C. for 30 min then warmed to room temperature over 30 min. The solution was then stirred at room temperature overnight. Progress of the reaction was followed by Thin Layer Chromatography (TLC) using $SiO_2$ stationary phase with EtOAc and Hexanes (4:6 v/v) as mobile phase ($R_f$ of the desired product=0.2) TLC plates were developed with phosphomolybdic acid or visualized with UV.

The overnight reaction mixture was diluted with $CH_2Cl_2$ (100 mL) and washed with a saturated aqueous solution of $NaHCO_3$ (1×100 mL) then washed with $H_2O$ (2×100 mL). The organic layer was separated, dried over $Na_2SO_4$, filtered, and concentrated under reduced pressure to provide the crude product.

The crude product was then dissolved in $CH_2Cl_2$ (25 mL) and purified using $SiO_2$ column chromatography using isocratic gradient elution with EtOAc and Hexanes 4:6 v/v. Fractions were analyzed using TLC with UV development. Fractions containing the desired product were combined and the solvent was evaporated to yield 4.54 g of the product (27%) The correct structure was verified by $^1H$ NMR spectroscopy.

Example 6.2

Synthesis of Galactose-OAc-PEG2 Vinyl Monomer

Synthesis was performed as described by Ambrosi et al. (*J. Chem. Soc. Perkin Trans.* 1, 2002, 45-52) with modifications, as summarized in Scheme 2.

To a round-bottom flask were added 3 Å molecular sieves (4.6 g, activated overnight at 150° C.) followed by PEG2 Vinyl Monomer (prepared as described in example 6.1) (3.83 g, 22.0 mmol) and anhydrous $CH_2Cl_2$ (90 mL). This mixture was stirred at −40° C. for 15 min. Then 2,3,4,6-tetra-O-acetyl-a-D-galactopyranosyl bromide (3.00 g, 7.33 mmol) was added to the reaction mixture followed by silver trifluoromethanesulfonate (2.27 g, 8.83 mmol) and the solution was stirred at −40° C. (±5° C.) under a flow of argon for 4 hours. The temperature of the reaction was maintained manually at −40° C. (±5° C.) using a mixture of dry ice and acetone.

Scheme 2

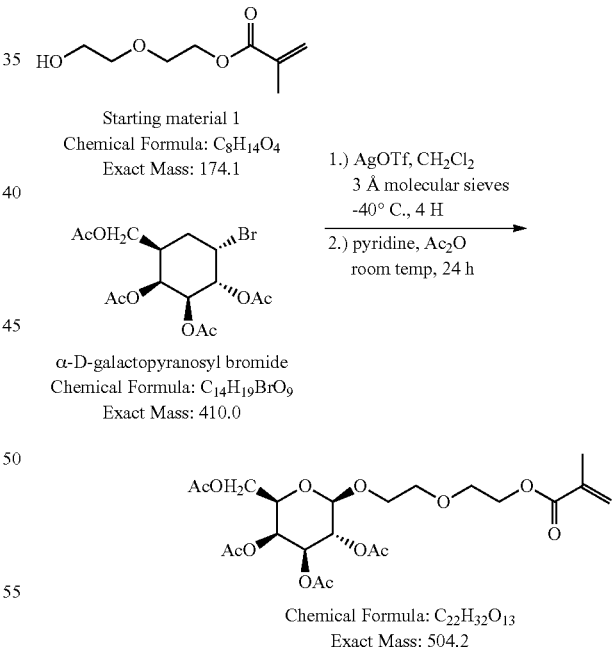

| Compound | MW | mmole | amount |
|---|---|---|---|
| Step 1: | | | |
| 2,3,4,6-tetra-O-acetyl-α-D-galactopyranosyl bromide | 410.0 | 7.33 | 3.00 g |
| Starting material 1 | 174.1 | 22.0 | 3.83 g |
| silver trifluoromethanesulfonate | 256.94 | 8.83 | 2.27 |
| 3 Å molecular sieves | N/A | — | 4.6 |
| $CH_2Cl_2$ | 84.93 | — | 90 mL |

Scheme 2

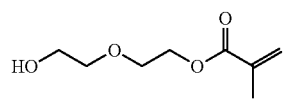

Starting material 1
Chemical Formula: C$_8$H$_{14}$O$_4$
Exact Mass: 174.1

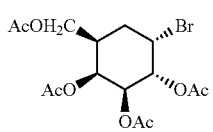

α-D-galactopyranosyl bromide
Chemical Formula: C$_{14}$H$_{19}$BrO$_9$
Exact Mass: 410.0

1.) AgOTf, CH$_2$Cl$_2$
3 Å molecular sieves
-40° C., 4 H

2.) pyridine, Ac$_2$O
room temp, 24 h

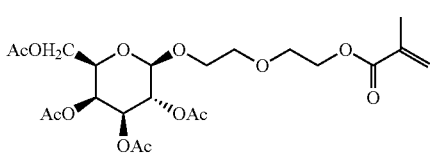

Chemical Formula: C$_{22}$H$_{32}$O$_{13}$
Exact Mass: 504.2

| Compound | MW | mmole | amount |
|---|---|---|---|
| Step 2: | | | |
| pyridine | 79.10 | 618 | 48.9 g, 50 mL |
| acetic anhydride | 102.09 | 106 | 10.8 g, 10 mL |

After stirring for 4 h at −40° C. the reaction mixture was warmed to room temperature, filtered via gravity filtration then the mother liquor was evaporated providing the crude product as a brown oil. The brown oil was then dissolved in anhydrous pyridine (50 mL, 618 mmol) and treated with acetic anhydride (10 mL, 106 mmol). This mixture is stirred under an argon atmosphere at room temperature for 1.0 hour to cap the unreacted alcohol.

The reaction mixture was then evaporated using a rotary evaporator yielding a brown liquid. The condensed mixture was dissolved in CH$_2$Cl$_2$ (300 mL) and vigorously stirred with a saturated aqueous NaHCO$_3$ solution (75 mL) in an open flask at room temperature, quenching any remaining Ac$_2$O. Transfer of the solution into a closed flask was carried out after all Ac$_2$O was reacted and no more gasses were being generated (>15 min reaction time needed to quench Ac$_2$O). After all Ac$_2$O was quenched the solution was transferred to a 500 mL separatory funnel and the organic layer was separated. The aqueous layer was extracted with CH$_2$Cl$_2$ (1×100 mL) and all organic layers were combined. Then the organic layer was washed with saturated aqueous NaHCO$_3$ solution (1×20 mL), separated, dried over Na$_2$SO$_4$, filtered and evaporated using a rotary evaporator, providing the crude product. The residual pyridine was removed by evaporation at very low pressure using an oil vacuum pump for no longer than 30 min before purification was attempted. Then the crude product was stored at −80° C. overnight.

The crude product was then dissolved in CH$_2$Cl$_2$ (20 mL) and purified using SiO$_2$ column chromatography using isocratic elution with EtOAc and Hexanes 4:6 v/v. Fractions were analyzed using TLC with UV development. The desired fractions were combined and the solvent was evaporated to provide 1.6 g (43%). Structure and purity were evaluated by $^1$H NMR spectroscopy.

Example 6.3

Standard Conditions for Polymer Gel Permeation Chromatography (GPC) Analysis

All GPC analysis was conducted on a Viscoteck GPC max equipped with UV/Vis, RI, viscometer, and light scattering detectors (RALS and LALS). Samples (100 μL, 0.1-0.3% polymer) were run on two PolarGel-M columns (300×7.5 mm, Polymer Laboratories) in series, DMF/1% LiBr eluent, at 60° C., with a flow rate of 0.75 mL/min. The GPC columns were standardized with PMMA Easi Vial Standards (Polymer Laboratories).

Example 6.4

Polymerization of Galactose-OAc-PEG2 Vinyl Monomer

Synthesis was performed as outlined in Scheme 3, as follows: Vinyl galactose monomer obtained in Example 6.2 (1.5 g, 2.97 mmoles), ECT (19.6 g, 0.0744 mmoles), AIBN (0.31 mg, 0.00186 mmoles; CTA:AIBN 40:1) and DMF (0.99 ml) were introduced under nitrogen into a sealed vial. The monomer concentration was 3 M without counting the volume of the galactose monomer. The resulting solution was degassed by bubbling nitrogen into the mixture for 30 minutes. The resulting solution was placed in a heat block (Thermometer: 67-68° C.; display: 70-71; stirring speed 350 rpm). After 5 hrs, the reaction was stopped by placing the vial on ice and exposing the mixture to air. The resulting polymer was purified by dialysis against methanol for 2 days using a 2 kDa membrane. The methanol was removed under reduced atmosphere and the polymer was dried under vacuum for at least 6 hours.

Scheme 3

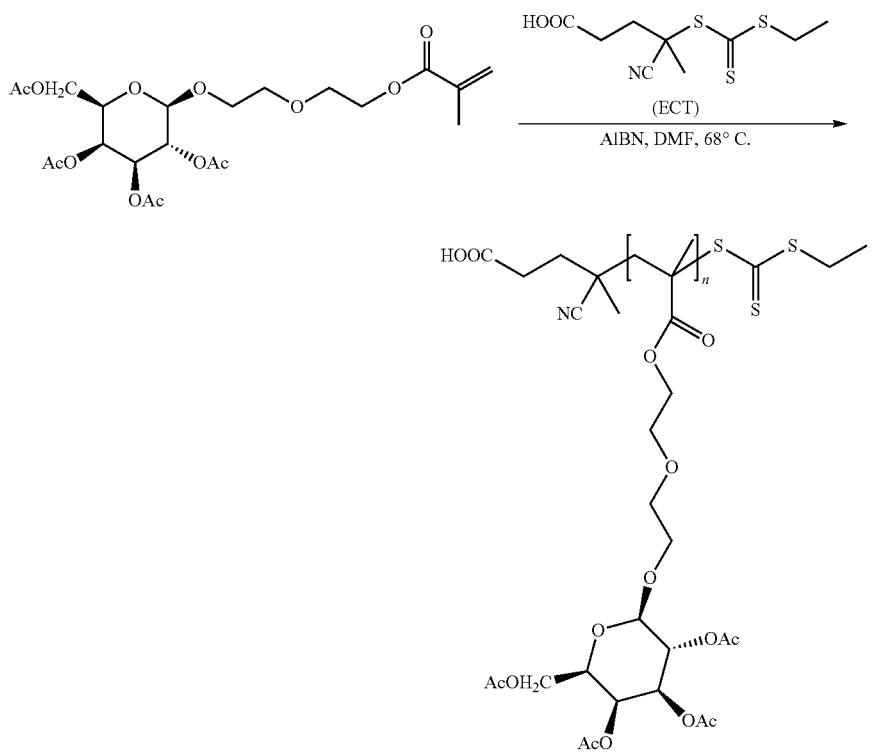

| Name | FW (g/mol) | Equiv. | mol | Weight |
|---|---|---|---|---|
| Gal(OAc)Peg2MA | 504.2 | 40 | $2.97 \times 10^{-3}$ | 1.5 g |
| ECT | 263.4 | 1 | $7.44 \times 10^{-5}$ | 19.6 mg |
| AIBN | 164.21 | 0.025 | $1.86 \times 10^{-6}$ | 0.31 mg |

[Monomers] = 3M; N2 Purging: 30 min; Temperature = 68° C.;
Polymerization Time = 300 min.

Characterization of polymer was performed by GPC analysis. The structure and composition were verified by $^1$H NMR (CDCl$_3$). Mn=5.8 KDa, PDI=1.14, dn/dc=0.075.

Example 6.5

Synthesis and Characterization of a Di-Block Polymer Poly[Gal(OAc)PEG2]-[HPMA-PDSMA] (Formulas IV AND IV.1) from Poly[Gal(OAc)PEG2]

poly[Gal(OAc)PEG2]-[HPMA-PDSMA]      (PIII)

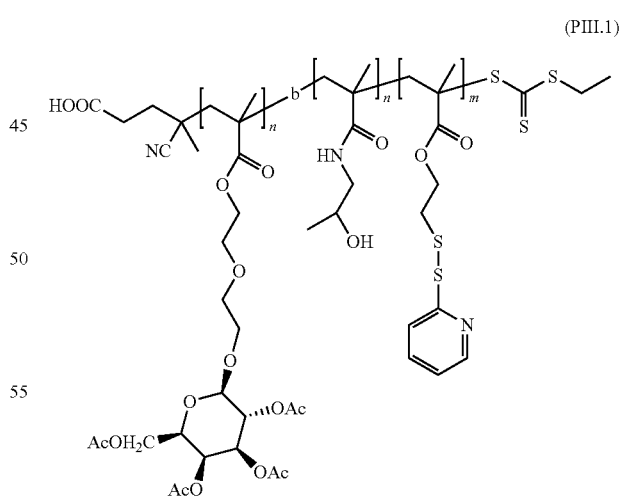

(PIII.1)

To 0.0434 mmoles of Poly[GAL(OAc)PEG2]-MacroCTA were added HPMA (0.860 g, 5.996 mmoles) and PDSMA (0.1332 g, 0.5216 mmoles), (1:150 CTA:Monomers), AIBN (0.71 mg, 0.00434 mmoles; CTA:AIBN 10:1) and DMF (2.62 ml) were introduced under nitrogen into a sealed vial. The monomer concentration was approximately 2.5 M. The resulting solution was degassed by bubbling nitrogen into the mixture for 30 minutes. The resulting solution was placed on a heat block for 4.5 hrs (thermometer: 68° C.; display: 70-71; stirring speed 300 rpm). After 4.5 hrs, the reaction was stopped by placing the vial on ice and exposing the mixture to air. The resulting polymer was purified by dialysis against methanol for 24 hours and then dried under vacuum for at least 6 hours. Polymer structure was verified by $^1$H NMR (DMF-d7) and by analytical GPC to determine polymer molecular weight and polydispersity: Mn=17.9 kDa, PDI=1.26.

Example 6.6

Synthesis and Characterization of a Tri-Block Polymer Poly[Gal(OAc)PEG2]-[HPMA-PDSMA]-[DMAEMA-BMA-PAA] from the Di-Block Polymer Poly[Gal(OAc)PEG2]-[HPMA-PDSMA] (PIV)

poly[Gal(OAc)PEG2]-[HPMA-PDSMA]-
[DMAEMA-BMA-PAA]     (PIV)

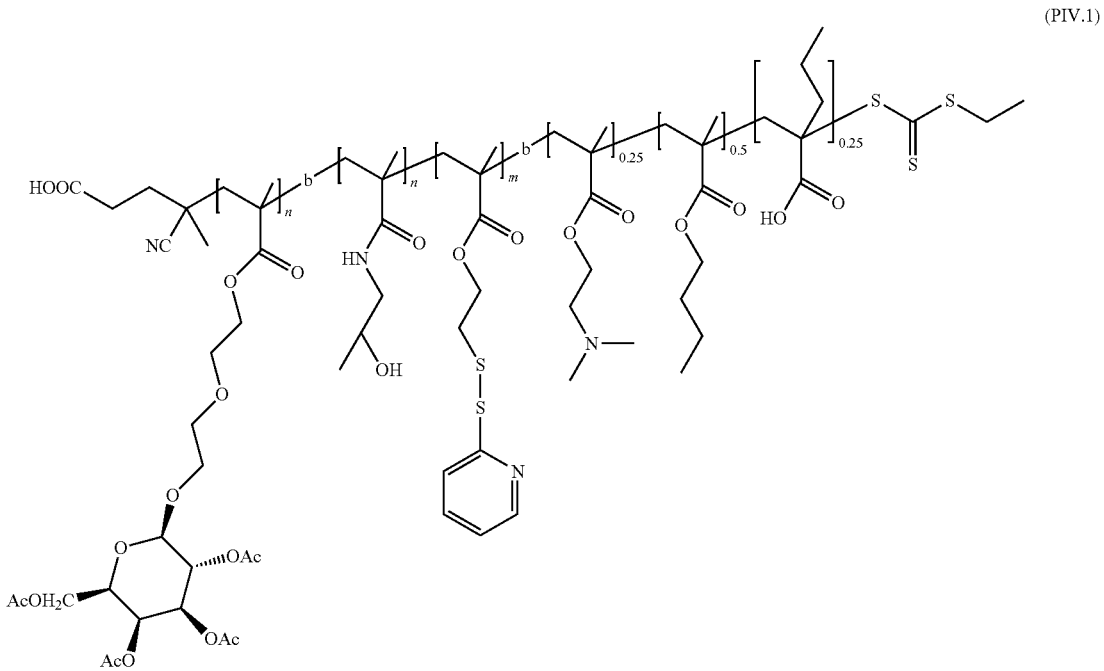

(PIV.1)

BMA (0.88 g, 6.16 mmoles), PAA (0.351 g, 3.075 mmoles), DMAEMA (0.484 g, 3.075 mmoles), MacroCTA from Step 6.5 (0.5073 g, 0.0284 mmoles; 1:434 CTA: Monomers), AIBN (0.00284 mmoles; CTA:AIBN 10:1) and DMF (2.22 ml) were introduced under nitrogen into a sealed vial. The monomer concentration was 3 M. The resulting solution was then degassed by bubbling nitrogen into the mixture for 30 minutes. The resulting solution was placed in a heat block for 11 hrs (Thermometer: 67-68° C.; display: 70-71; stirring speed 350 rpm, assuming 50% of conversion). After 11 hrs, the reaction was stopped by placing the vial on ice and exposing the solution to air. The resulting polymer was purified by precipitation from Acetone/DMF 1:1 into hexane/ether 75/25 (three times). The resulting polymer was dried under vacuum for at least 8 hours and analyzed by $^1$H NMR (CDCl$_3$) to verify the correct structure and by analytical GPC to determine polymer molecular weight and polydispersity. Mn=47 kDa, PDI=1.7.

Example 6.7

Deprotection of Tri-Block Polymer to Form Polymer from Example 6.6

The reaction conditions are as described by Ambrosi et al. (*J. Chem. Soc. Perkin Trans.* 1, 2002, 45-52) with modifications, as summarized in scheme 4.

Scheme 4

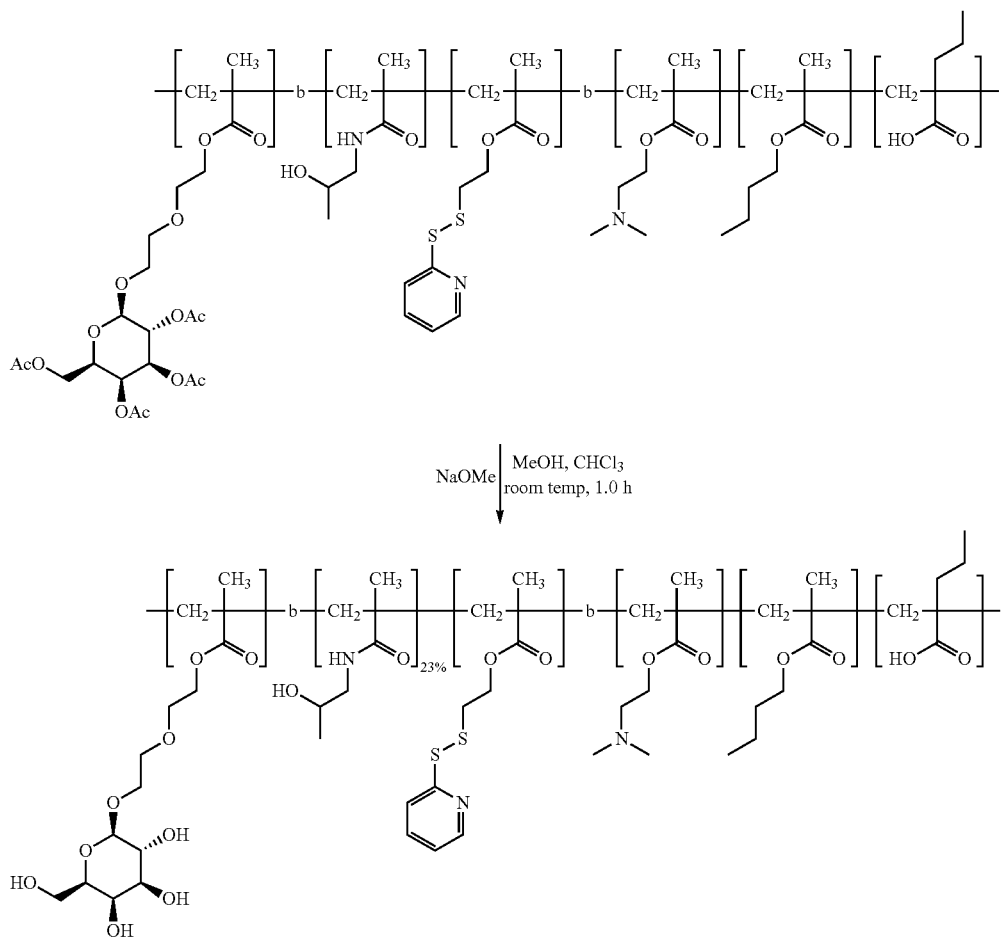

| Compound | MW | μmole | amount |
|---|---|---|---|
| Polymer |  |  | 700 mg |
| GAL functionality |  |  |  |
| PDS functionality |  |  |  |
| sodium methoxide | 54.02 | 1385 | 75 mg |
| MeOH | 32.04 |  | 3.0 mL |
| CHCl₃ | 119.38 |  | 1.5 mL |
| AcOH | 60.05 | 693 | 40 μL |
| 2,2'-dipyridyl disulfide | 220.0 | 227 | 50 mg |

To a 50 mL round-bottom flask was added the polymer from example 6.6 (680 mg, 4334 μmmol polymer, 173 μmol galactose, 87 μmmol pyridyl disulfide) followed by anhydrous methanol (3.0 mL), anhydrous chloroform (1.5 mL) and sodium methoxide (74.8 mg, 1386 μmol, 8 equivalents relative to galactose). The resulting mixture was stirred under an atmosphere of argon at room temperature for 1.0 hour. Then glacial acetic acid (39.7 μL, 693 μmmol, 4 equivalents relative to galactose) was added to the reaction followed by 2,2'-dipyridyl disulfide (49.5 mg, 225.2 μmmol, 2 equivalents relative to pyridyl disulfide). This mixture is stirred at room temperature for 1.0 hour under a flow of argon gas.

After capping with 2,2'-dipyridyl disulfide for 1.0 hour the reaction was diluted with MeOH (5 mL) and filtered via gravity filtration. The filtered reaction mixture was transferred to a dialysis membrane with a 2000 molecular weight cut off (Spectrum Labs, Spectra/Por Dialysis Membrane MWCO: 2000) and dialyzed against MeOH (2×500 mL) for 24 hours. After the dialysis was complete the polymer was transferred to a round-bottom flask, and the solvent was evaporated using a rotary evaporator. The resulting polymer was analyzed by $^1$H NMR using CD$_3$OD and DMF-d7 to verify the correct structure. The zeta potential of a solution of polymer (40 mM) was measured in 5% Glucose, 10 mM Hepes pH7.4 and was determined to be 5.31 mV (width=5.25 mV, 46.4 kcps, Mob 0.42 μmcm/Vs, Cond 0.15 mS/cm).

Since the pyridyl disulfide functionality on the polymer was difficult to detect by NMR spectroscopy, this functionality was quantified using UV/Vis (FIG. 26). The final polymer (100 mg) was dissolved in EtOH (1.0 mL) providing a polymer solution at a concentration of 100 mg/mL. An aliquot of this polymer solution (10 μL, 1.0 mg, 6.6 μmol) was treated with an aqueous solution of 1.0 M dithiothreitol (10 μL, 10.0 μmol, DTT) for 10 min before being diluted with H$_2$O (80 µL) giving a reduced polymer solution of 0.066 M. Since the expected incorporation of pyridyl disulfide should be 2% on the polymer one would expect the concentration of the leaving group pyridine-2-thione should be 1.33 mM (i.e., 0.066×0.02=0.00133 M) after the polymer was treated with DTT as described above. Since the molar absorptivity of pyridine-2-thione at 343 nm is ϵ=8.08×10$^3$ M$^{-1}$ cm$^{-1}$ (Hermanson, G. T. *Bioconjugate Techniques*, 1996, 1$^{st}$ ed. Academic Press, an imprint of Elsevier, page 66) and the path length of the NanoDrop spectrometer used is 0.1 cm the expected absorption for the reduced polymer solution described above is A=1.075. After analysis of the reduced polymer solution by UV/Vis the experimentally determined absorption was A=0.438 at 343 nm. This demonstrated the presence of the pyridyl disulfide functionality in the polymer with the actual concentration of 1% total pyridyl disulfide incorporation (theoretically calculated value was 2%).

After dialysis the polymer was dissolved in absolute EtOH at 100 mg/mL concentration and then directly used in conjugation reactions with siRNA. Polymer equivalent weight calculation is determined based on the percent monomer incorporation.

Example 7

Conjugation of siRNA to a Tri-Block Polymer

[Gal]$_{4K}$- [HPMA$_{90}$-PDSMA$_{10}$]$_{12.0K}$-[D$_{25}$-B$_{50}$-P$_{25}$]$_{30K}$ (PV)

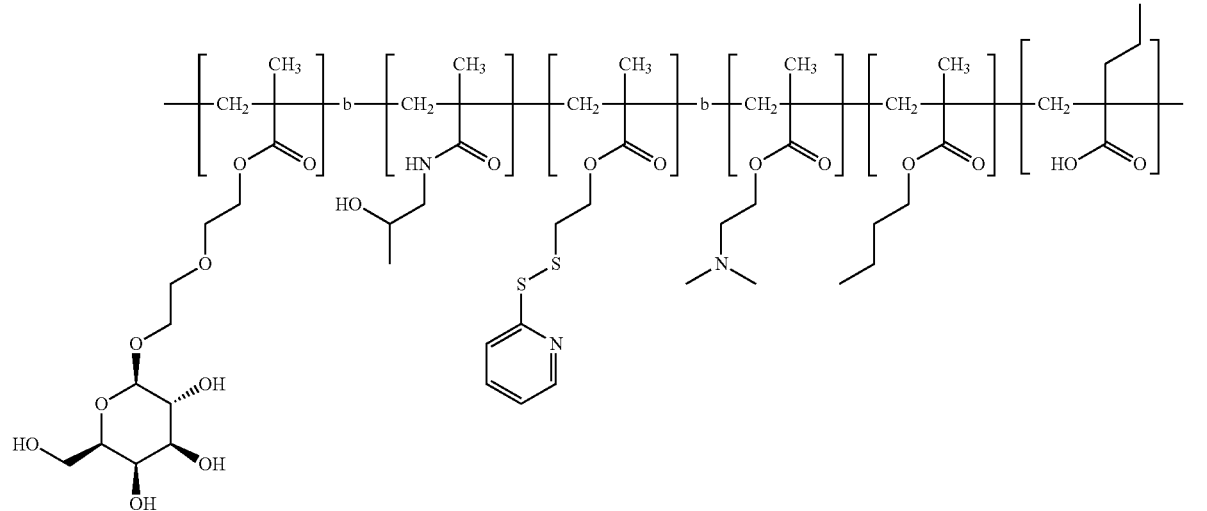

(PV.1)

Example 7.1

Preparation of an Activated RNA Duplex Against GAPDH

Preparation of thiolated siRNA was as follows. To a 15 mL Falcon tube was added tris(2-carboxyethyl)phosphine hydrochloride (1.0 mg, 3.5 µmol, TCEP) followed by NaHCO$_3$ (1.2 mg, 14.0 µmol), H$_2$O (500 µL) and GAPDH-SSC$_6$OH duplex (5.0 mg, 0.37 µmol, Agilent Technologies). This mixture was allowed to stand at room temperature. After 30 min, 5.0 M NaCl (20.0 µL) was added followed by cold (−20° C.) 100% EtOH (5.0 mL). The mixture was placed into a −80° C. refrigerator for 30 min to achieve complete RNA precipitation. The Falcon tube was then centrifuged to pellet the RNA. The mother liquor was removed and the remaining RNA pellet was triturated using cold (+4° C.) 70% EtOH (1×1.0 mL). The remaining RNA pellet was then dissolved in isotonic glucose (5.0 mL, 5.05 wt % glucose, 10 mM HEPES, pH 7.4) to give an aqueous RNA solution with RNA concentration at 0.7 µg/µL (by UV analysis).

By similar methods the following activated RNA duplex (against ApoB) was also prepared.

Example 7.2

Conjugation of an Active RNA Duplex to Tri-Block Polymer (FormulaP II) and Di-Block Polymer (Formula Ii without Galactose Targeting BLOCK)

Formulation 1. The polymer (Formula PII) (500 mg) was dissolved into 100% EtOH (5.0 mL) providing a solution having polymer concentration of 100 mg/mL. An aliquot of the polymer solution (34.69 uL, 22.9 umol) was transferred into a 15 mL falcon tube. To the polymer/EtOH solution was added all at once an aliquot of the reduced GAPDH RNA isotonic glucose solution (300 uL, 300 ug RNA, 0.022 umol RNA, solution preparation described above). The reaction mixture was mixed and allowed to stand at room temperature. The reaction progress was monitored by gel electrophoreses (described below). After reacting overnight (ca. 18 h) the solution was diluted with isotonic glucose (2665.3 uL, 5.05 wt % glucose, 10 mM HEPES, pH 7.4) giving 3.0 mL total of a formulation ready for in vivo testing. This gave an intended siRNA concentration of 0.1 mg/mL and an intended polymer concentration of 1.16 mg/mL in the formulation.

Formulation 2. The polymer (Formula PII) (500 mg) was dissolved into 100% EtOH (5.0 mL) providing a solution having polymer concentration of 100 mg/mL. An aliquot of the polymer solution (151.3 uL, 99.9 umol) was transferred into a 15 mL falcon tube. To the polymer/EtOH solution was added all at once an aliquot of the reduced GAPDH RNA isotonic glucose solution (300 uL, 0.022 umol RNA, solution preparation described above). The reaction mixture was mixed and allowed to stand at room temperature. The reaction progress was monitored by gel electrophoreses (described below). After reacting overnight (ca. 18 h) the solution was diluted with isotonic glucose (2548.7 uL, 5.05 wt % glucose, 10 mM HEPES, pH 7.4) giving 3.0 mL total of a formulation ready for in vivo testing. This gave an intended siRNA concentration of 0.1 mg/mL and an intended polymer concentration of 5.04 mg/mL in the formulation. The zeta potential of the conjugate was measured (40 mM (based on polymer) in 5% Glucose, 10 mM Hepes pH7.4) and was determined to be 1.2 mV (width=5.71 mV, 100.6 kcps, Mob 0.09 μmcm/Vs, Cond 0.15 mS/cm).

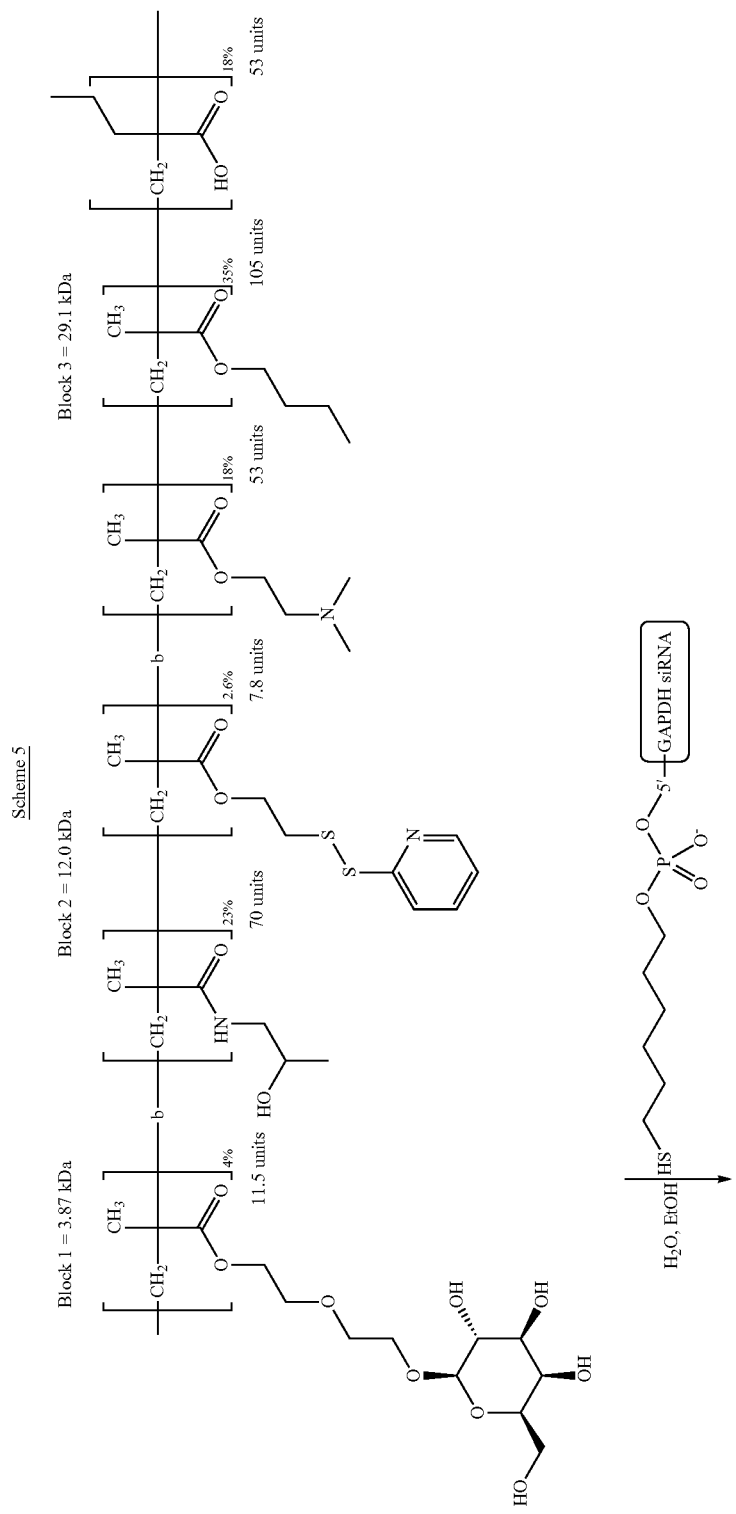

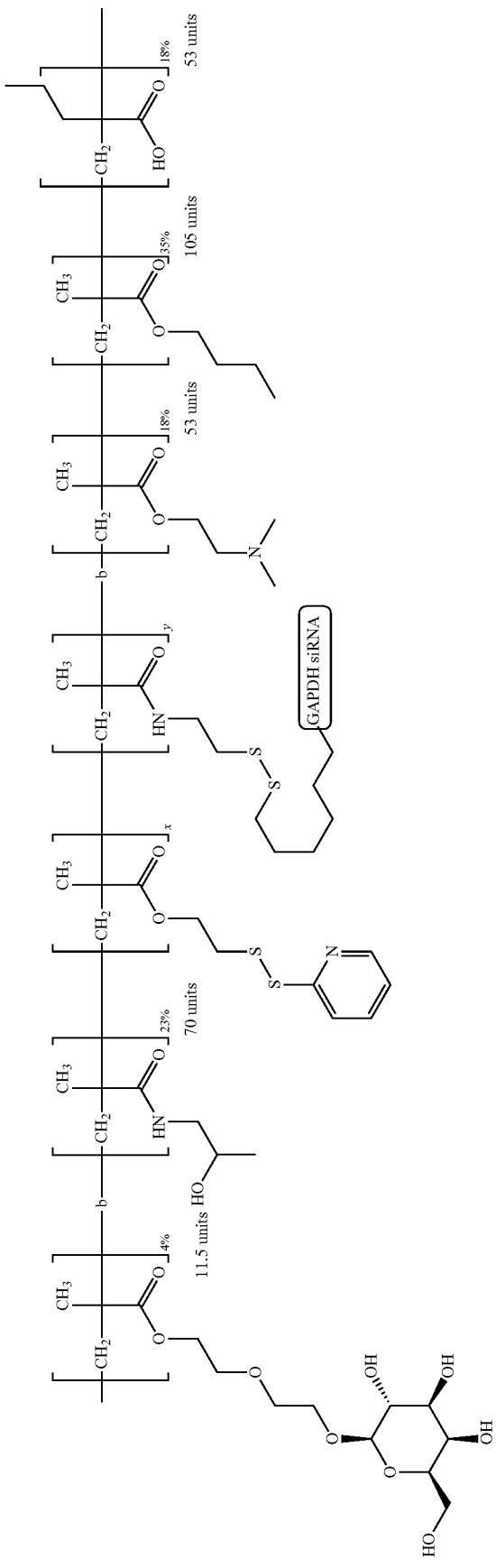

Formulation 3. The polymer (Formula PII) (500 mg) was dissolved into 100% EtOH (5.0 mL) providing a solution having polymer concentration of 100 mg/mL. An aliquot of the polymer solution (69.54 µL, 45.9 µmol) was transferred into a 15 mL falcon tube. To the polymer/EtOH solution was added all at once an aliquot of the reduced GAPDH RNA isotonic glucose solution (600 µL, 600 µg RNA, 0.044 µmol RNA, solution preparation described above). The reaction mixture was mixed and allowed to stand at room temperature. The reaction progress was monitored by gel electrophoreses (described below). After reacting overnight (ca. 18 h) the solution was diluted with isotonic glucose (2330.5 µL, 5.05 wt % glucose, 10 mM HEPES, pH 7.4) giving 3.0 mL total of a formulation ready for in vivo testing. This gave an intended siRNA concentration of 0.2 mg/mL and an intended polymer concentration of 2.32 mg/mL in the formulation.

Formulation 4. The polymer (Formula PII) (500 mg) was dissolved in 100% EtOH (5.0 mL) providing a solution having a polymer concentration of 100 mg/mL. An aliquot of the polymer solution (295.6 µL, 195.1 µmol) was transferred into a 15 mL falcon tube. To the polymer/EtOH solution was added all at once an aliquot of the reduced GAPDH RNA isotonic glucose solution (600 µL, 600 µg RNA, 0.044 µmol RNA, solution preparation described above). The reaction mixture was mixed and allowed to stand at room temperature. The reaction progress was monitored by gel electrophoreses (described below). After reacting overnight (ca. 18 h) the solution was diluted with isotonic glucose (2104.4 µL, 5.05 wt % glucose, 10 mM HEPES, pH 7.4) giving 3.0 mL total of a formulation ready for in vivo testing. This gave an intended siRNA concentration of 0.2 mg/mL and an intended polymer concentration of 9.85 mg/mL in the formulation.

Formulation 5. The polymer (Formula PII without the galactose block) (200 mg) was dissolved into 100% EtOH (2.0 mL) providing a solution having polymer concentration of 100 mg/mL. An aliquot of the polymer solution (126.5 µL, 88.15 µmol) was transferred into a 15 mL falcon tube. To the polymer/EtOH solution was added all at once an aliquot of the reduced GAPDH RNA isotonic glucose solution (300 µL, 0.022 µmol RNA, solution preparation described above). The reaction mixture was shaken, centrifuged and allowed to stand at room temperature. The reaction progress was monitored by gel electrophoreses (described below). After reacting overnight (ca. 18 h) the solution was diluted with isotonic glucose (2573.5 µL, 5.05 wt % glucose, 10 mM HEPES, pH 7.4) giving 3.0 mL total of a formulation ready for in vivo testing.

Formulation 6. The polymer (Formula PII without the galactose block) (200 mg) was dissolved into 100% EtOH (2.0 mL) providing a solution having polymer concentration of 100 mg/mL. An aliquot of the polymer solution (59.78 µL, 41.7 µmol) was transferred into a 15 mL falcon tube. To the polymer/EtOH solution was added all at once an aliquot of the reduced GAPDH RNA isotonic glucose solution (600 µL, 0.044 µmol RNA, solution preparation described above). The reaction mixture was shaken, centrifuged and allowed to stand at room temperature. The reaction progress was monitored by gel electrophoreses (described below). After reacting overnight (ca. 18 h) at room temperature the solution was diluted with isotonic glucose (2340.2 µL, 5.05 wt % glucose, 10 mM HEPES, pH 7.4) giving 3.0 mL total of a formulation ready for in vivo testing.

By similar methods, the following formulations were prepared with activated RNA duplex (ApoB) conjugated to tri-block polymer (Formula PII) and di-block polymer (Formula PII without the galactose block). Polymers were taken up in EtOH at 100 mg/mL. Activated RNA duplex was dissolved in isotonic glucose (5.0 mL, 5.05 wt % glucose, 10 mM HEPES, pH 7.4) giving an aqueous RNA solution with RNA concentration at 1.0 µg/µL (by UV analysis). After 16 hr, additional isotonic glucose (5.0 mL, 5.05 wt % glucose, 10 mM HEPES, pH 7.4) was added to the mixture to bring the final volume to 3.0 mL.

| Goups | Polymer | siRNA | ug/formulation siRNA | ug/formulation Polymer | Final Formulation (Vol ul) |
|---|---|---|---|---|---|
| 1 | Formula PII | ApoB | 600 | 30000 | 900 |
| 2 | Formula PII | ApoB | 600 | 30000 | 900 |
| 3 | Formula PII (without gal) | ApoB | 600 | 25979 | 859.8 |
| 4 | Formula PII (without gal) | ApoB | 600 | 25979 | 859.8 |

Example 7.3

Gel Electrophoresis Analysis

The conjugation reactions were analyzed by gel electrophoresis (20% polyacrylamide, 1×TBE gel from Invitrogen, 1×TBE buffer for ca. 1 h at 200 V, stained in 50 mL 1×TBE with 2.5 µL SYBR gold for 15 min). Aliquots of the 3.0 mL in vivo samples prepared above were withdrawn and a dilution series was prepared. For example, the sample (4.0 µL) was diluted with blue-dye loading buffer (6.0 µL) giving a sample with final RNA concentration of 0.04 µg/µL. Then 4 µL of this diluted sample was applied to the gel. Similarly, the sample (4.0 µL) was treated with DTT (1.0 µL, 1.0 M solution) for 10 minutes before being diluted further with 2.5% SDS (2.0 µL) and loading buffer (3.0 µL) giving a sample with final RNA concentration of 0.04 µg/µL. Then 4 µL of this reduced solution was also applied to the gel for analysis.

Example 8

In Vitro mRNA Knockdown in HepG2 and HeLa Cells with siRNA Conjugated to a Tri-Block Polymer (Formula PII)

Example 8.1

General Transfection Procedure and Determination of Knockdown Activity

Cells were purchased from ATCC (Manassas, Va.), unless otherwise noted, and cultured according to the distributor's instructions. Cells were plated in 96 well plates at a density of 10,000 cells/well and allowed to adhere overnight in MEM media with 10% FBS (100 µL). Transfection samples were diluted to a final volume of 25 µL with ITG (5.05 wt % glucose, 10 mM HEPES, pH 7.4) or PBS, and added to the cells (final volume of 125 µL). After 24 hrs, the extent of siRNA mediated GAPDH or ApoB mRNA reduction is assessed. The media was removed and cells were rinsed with PBS. A two-step RT-PCR directly from cell culture wells was performed using the Fast SYBR Green Cells-to-Ct Kit (Ambion). Real-time PCR was conducted with the StepOne-Plus Real-Time PCR System using primers for SYBR Green PCR; GAPDH and RPL13A internal normalizer gene. Reactions (20 µL total) consisted of 10 µL of 2× Fast SYBR Green PCR Mastermix, 1 µL of primers, and 9 µL of 1:4 diluted cDNA in nuclease-free water. The following PCR parameters were utilized: 95° C. for 20 s followed by 40 cycles of 95° C. for 3 s and 60° C. for 30 s. Threshold cycle (CT) analysis was used to quantify GAPDH, normalized to RPL13A and relative to expression of untreated cells. For ApoB knockdown, the cells were treated as previously described.

Example 8.2

In Vivo Biodistribution and mRNA Knockdown in Liver Cells with siRNA conjugated to a Tri-Block Polymer (Formula PII) Following IV Delivery by Tail Vein Injection to Mice

Example 8.3

General Procedure 7-9 weeks old female Balb/C mice (Charles River Laboratories) were dosed with siRNA-polymer formulations via the tail vein at a dosing volume of 0.01 mL/g, n=5 per group. siRNA sequences for ApoB and GAPDH were as shown below.

RNA Sequences:

| Gene | Sense Strand: | Antisense Strand: |
|---|---|---|
| GAPDH | 5'-HO—(CH2)6—S—S—(CH2)6-rGrGrU rCrArU rCrCrA rUrGrA rCrArA rCrUrU rUdTdT-3' [SEQ ID NO: 1] | 5'-rArArA rGrUrU rGrUrC rArUrG rGrArU rGrArC rCdTdT-3' [SEQ ID NO: 2] |
| ApoB | 5' OH—(CH2)6—S—S—(CH2)6-rGmUrCrAmUrCrArCrArCmUrGrArAmUrA rCrCrArAmU-3' [SEQ ID NO: 3] | 5'-rArUrUrGrGrUrArUrUrCrArGrUrGrUrGrArUrGrAr CrArC-3' [SEQ ID NO: 4] | m = 2'-O-methyl modified,
r = ribonucleotide,
d = deoxynucleotide 18-48 hours post dose animals were sacrificed. Blood was collected via cardiac puncture for serum isolation for blood chemistry analysis. Liver tissue was isolated (lower ⅔ of left lobe), placed in RNAlater (Ambion), and cut up in small pieces for improved tissue penetration. RNA was isolated from ~50 mg of liver tissue using the MagMAx-96 for MicroArrays Total RNA Isolation kit (Ambion). RNA was converted to cDNA using the High Capacity cDNA Reverse Transcription Kit (Applied Biosystems). SYBR Green Real-Time PCR was performed to examine mRNA levels for siRNA target genes ApoB and GAPDH as well as normalize genes Calnexin 1 and Hprt1 (primer sequences are shown below).

Primer Sequences:

| Name | Chemistry | Forward Primer: | Reverse Primer: |
|---|---|---|---|
| GAPDH | SYBR | 5'-CATGGCCTTCCGTGTTCCTA-3' [SEQ ID NO: 5] | 5'-ATGCCTGCTTCACCACCTTCT-3' [SEQ ID NO: 6] |
| Hprt1 | SYBR | 5'-CCTAAGATGAGCGCAAGTTGAA-3' [SEQ ID NO: 7] | 5'-CCACAGGACTAGAACACCTGCT-3' [SEQ ID NO: 8] |
| Calnexin | SYBR | 5'-ATGGAAGGGAAGTGGTTACTGT-3' [SEQ ID NO: 9] | 5'-GCTTTGTAGGTGACCTTTGGAG-3' [SEQ ID NO: 10] |
| ApoB | SYBR | 5'-AAGCACCTCCGAAAGTACGTG-3' [SEQ ID NO: 11] | 5-CTCCAGCTCTACCTTACAGTTGA-3' [SEQ ID NO: 12] |

Step One Software v2.1 (Applied Biosystems) was used to normalize target genes to both normalizer genes. A cDNA aliquot from each buffer control sample was pooled and used to compare to each treated sample. In addition, each buffer control sample was compared to the pooled buffer samples. Blood Chemistry analysis was performed at Phoenix Central Laboratory (Everett, Wash.) on blood samples collected 48 hours post dose.

For biodistribution/PK studies to detect siRNA via a hybridization assay, the following was performed. 7-9 week old Balb/C mice were dosed with either GAPDH or ApoB siRNA-polymer formulations via the tail vein. Animals were sacrificed at 1 hour post dose. Blood was collected via cardiac puncture, allowed to coagulate at room temperature, centrifuged to collect serum, and then stored on ice or at −20° C. for later analysis. In addition to blood, liver, spleen, kidney and lung tissues were collected for analysis. An ~50 mg piece of tissue was weighed and placed in a homogenization tube containing ~1 mL of tissue homogenization buffer (3 M guanidinium isothiocyanate/10 mM EDTA/0.1M Tris pH 7.5, 0.5M NaCl) to make a final tissue concentration of 50 mg/ml. Tissues were homogenized using a FastPrep24 homogenizer (MP Biomedicals), 3 times, 20 seconds each, with 3 minutes rest in between each run. Samples were placed on ice for 5 minutes, followed by centrifugation for 5 minutes at 12,000 rpm. An aliquot of tissue homogenate was transferred to a 96 well plate and stored either on ice or at −20° C. for later analysis. To measure siRNA levels in blood and tissue samples, streptavidin coated 96-well plates were incubated with capture oligo, a biotinylated oligo that is complementary to 9 nucleotides of siRNA antisense strand. The capture oligo was diluted to 250 nM in 20 mM Tris-HCl pH 7.5, 100 uL/well was added to each plate and allowed to incubate for 30 minutes at room temperature on a plate shaker. A siRNA standard curve from 0.293 ng/ml-300 ng/ml (11 two-fold serial dilutions starting at 300 ng/ml) as well as dilutions of serum and tissue samples were prepared in dilution buffer: 1 M guanidinium isothiocyanate/10 mM EDTA/0.1M Tris pH 7.5, 0.5M NaCl. These samples were heated to 90 C. for 10 minutes. Meanwhile, the plate coated with capture probe was washed 2 times with wash buffer: 1M NaCl, 0.1M Tris pH 9.0, 2 mM $MgCl_2$, 1% Tween 20. 50 uL/well of a fluorescein labeled reporter oligo, complementary to the remaining 11 nucleotides of antisense strand diluted to 0.1 uM in dilution buffer was added to the plates. Working very quickly, 50 uL/well of siRNA standards and diluted tissue samples from 90 C incubation were added in duplicate to plates containing the fluorescein labeled oligo. Samples were incubated for 5 minutes at room temperature. Contents of plate were discarded and plates were washed 5 times with wash buffer. 100 uL/well of HRP-labeled anti-fluorescein Fab (Roche) diluted to 15 mU/ml in PBS were added. Plates were incubated for 1 hour at room temperature on plate shaker and then washed 5 times with wash buffer. 100 uL/well of TMB substrate were added and incubated for 10 minutes in the dark. 100 uL/well stop solution (1M phosphoric acid) is added. Plates were read at 450 nm O.D. Readouts were plotted as ng siRNA/mg tissue where siRNA concentration in tissues is determined as ng siRNA/ml from standard curve. Those values were then divided by 50 mg/ml tissue concentration from starting solution.

Example 8.4

Biodistribution Studies and GAPDH/ApoB Knockdown Following Tail Vein Delivery to Mice of a Complex of siRNA Conjugated to a Tri-Block Polymer (Formula PII)

Complexes were delivered to mice by tail vein injection as previously described.

| | |
|---|---|
| Protocol | Biodistribution Studies and GAPDH/ApoB Knockdown Following Tail Vein Delivery to Mice of a Complex of siRNA Conjugated to a Tri-block Polymer (Formula PII) |
| Purpose | GAPDH knockdown and biodistribution study testing siRNA conjugates with HPMA/PDSMA-HB +/− Galactose polymers |
| Animals | Balb/c mice, female |
| Age | 7-8 weeks |
| Dose volume | 0.2 ml per 20 g mouse; 10 mg/kg |
| Route | i.v. |
| Tissues collected for biodistribution | liver, lung, spleen, serum 1 hour post dose |
| Tissues collected for KD | liver and lung on day 2 post dose. |
| Dosing: | Dose mice once |

Biodistribution studies were conducted as previously described. Knockdown assays were conducted as previously described.

Example 8.5

GAPDH/ApoB Knockdown Following Tail Vein Delivery to Mice of a Complex of siRNA Conjugated to Tri-Block Polymers Complexes of siRNA conjugated to tri-block polymers were prepared as previously described (Example 7.2). The resulting siRNA tri-block polymer conjugates were delivered to mice by tail vein injection as previously described, under the listed study protocol. At 24-48 hr post dose, the animals are sacrificed and mRNA levels determined as previously detailed in Example 8.3.

| | |
|---|---|
| Protocol | GAPDH and ApoB knockdown and biodistribution study testing siRNA conjugates with triblock polymers or control polymers |
| Animals | Balb/c mice or C57 black mice, female |
| Age | 7-8 weeks |
| Dose volume | 0.2 ml per 20 g mouse: 10 mg/kg |
| Route | i.v. |
| Tissues collected for biodistribution | Liver, lung, spleen, serum 1 hour post dose |
| Tissues collected for KD | Liver on day 2 post dose. |
| Dosing: | Dose mice once for each formulation |

The results from these triblock polymer—siRNA conjugate in vivo knockdown activity studies appear in the following table.

| Triblock Polymer-siRNA Conjugate In Vivo Knockdown Activity | | | | | | | | |
|---|---|---|---|---|---|---|---|---|
| | | | | | ApoB mRNA | | GAPDH mRNA | |
| Structure | polymer mg/kg | siRNA mg/kg | harvest timepoint | Special note | siRNA | Relative mRNA levels | st dev | Relative mRNA levels | st dev |
| [Nag-OH(Peg3)]$_{15.2\ KDa}$-[HPMA$_{92}$-PDSMA$_8$]$_{10.1\ KDa}$-[D$_{25}$-B$_{50}$-P$_{25}$]$_{12.1\ KDa}$ | 38.7 | 1.0 | 48 | b | | 0.72 | 0.12 | 0.91 | 0.18 |
| | 38.7 | 1.0 | 48 | | ApoB | 1.02 | 0.13 | 1.37 | 0.22 |
| | 38.7 | 1.0 | 48 | | ApoB | 0.74 | 0.17 | | |
| | 77.7 | 2.0 | 48 | | ApoB | 1.07 | 0.14 | | |
| | 122 | 2.0 | 24 | | ApoB | 0.49 | 0.08 | 0.90 | 0.02 |
| [Nag-OH(Peg3)]$_{15.2\ KDa}$-[OCH$_2$CH$_2$OCH$_2$CH$_2$NH$_2$]$_{10.7\ KDa}$-[D$_{25}$-B$_{50}$-P$_{25}$]$_{23.0\ KDa}$ | 5 | 1.0 | 48 | | ApoB | 1.09 | 0.10 | 1.27 | 0.20 |
| | 5 | 2.0 | 48 | | ApoB | 1.14 | 0.22 | 1.34 | 0.18 |
| | 10 | 2.0 | 48 | | ApoB | 1.00 | 0.16 | | |
| [HPMA-PDSMA]$_{12.7\ KDa}$-[D$_{25}$-B$_{50}$-P$_{25}$]$_{15.3\ KDa}$ | 42 | 1.0 | 48 | | GAPDH | | | 1.01 | 0.18 |
| | 20 | 2.0 | 48 | | GAPDH | | | 1.10 | 0.17 |
| | 93 | 2.0 | 24 | | ApoB | 0.80 | 0.16 | 1.38 | 0.13 |
| [Nag-OH(Peg3)]$_{15.2\ KDa}$-[OCH$_2$CH$_2$OCH$_2$CH$_2$NH$_2$]$_{10.7\ KDa}$-[D$_{25}$-B$_{50}$-P$_{25}$]$_{23.0\ KDa}$ | 10 | 2.0 | 48 | | ApoB | 1.14 | 0.10 | | |
| [GAL-OH(PEG1)]$_{7.05\ KDa}$-[HPMA$_{90}$-PDSMA$_{10}$]$_{7.1\ KDa}$-[D$_{25}$-B$_{50}$-P$_{25}$]$_{23.3\ KDa}$ | 123 | 2.0 | 24 | | ApoB | 0.23 | 0.06 | 0.90 | 0.10 |
| | 62 | 1.0 | 24 | | ApoB | 0.51 | 0.10 | 0.88 | 0.10 |
| | 31 | 0.5 | 24 | | ApoB | 0.67 | 0.04 | 0.89 | 0.08 |
| | 124 | 2.0 | 24 | | ApoB | 0.41 | 0.14 | 1.32 | 0.20 |
| | 124 | 2.0 | 24 | a | ApoB | 0.27 | 0.06 | 1.23 | 0.37 |
| | 80 | 1.5 | 24 | | ApoB | 0.63 | 0.20 | 0.97 | 0.22 |
| | 50 | 0.9 | 24 | | ApoB | 1.02 | 0.15 | 1.01 | 0.15 |
| | 63 | 1.0 | 24 | | ApoB | 0.48 | 0.10 | 0.89 | 0.10 |
| | 126 | 2.0 | 24 | a | ApoB | 0.30 | 0.05 | 0.84 | 0.10 |
| | 126 | 2.0 | 24 | | ApoB | 0.19 | 0.06 | 0.94 | 0.06 |
| | 80 | 1.5 | 24 | | ApoB | 0.93 | 0.14 | 1.04 | 0.22 |
| | 50 | 0.9 | 24 | | ApoB | 1.01 | 0.09 | 1.12 | 0.12 |
| [GAL-OH(PEG2)]$_{3.9\ KDa}$-[HPMA$_{90}$-PDSMA$_{10}$]$_{12.0\ KDa}$-[D$_{25}$-B$_{50}$-P$_{25}$]$_{29.1\ KDa}$ | 98 | 2.0 | 48 | | GAPDH | | | 0.45 | 0.06 |
| | 50 | 1.0 | 48 | | GAPDH | | | 0.72 | 0.11 |
| | 100 | 2.0 | 48 | | ApoB | 0.28 | 0.14 | 1.19 | 0.17 |
| | 100 | 2.0 | 24 | | ApoB | 0.40 | 0.24 | 1.38 | 0.24 |
| | 100 | 1.7 | 24 | | ApoB | 1.11 | 0.02 | 1.77 | 0.02 |
| | 75 | 7.2 | 24 | | ApoB | 0.57 | 0.04 | 1.59 | 0.14 |
| | 50 | 0.8 | 24 | | ApoB | 0.92 | 0.08 | 1.24 | 0.14 |
| | 25 | 0.4 | 24 | | ApoB | 1.36 | 0.10 | 1.37 | 0.10 |
| [Nag-OH(PEG2)]$_{24.7\ KDa}$-(PEG2)]$_{24.7\ KDa}$-[HPMA$_{90}$-PDSMA$_{10}$]$_{14.0\ KDa}$-[D$_{25}$-B$_{50}$-P$_{25}$]$_{30.0\ KDa}$ | 130 | 2.0 | 48 | | ApoB | 0.70 | 0.13 | 1.17 | 0.08 |
| [GALOH(PEG3)]$_{3.2\ KDa}$-[HPMA-PDSMA]$_{11.4\ KDa}$-[D$_{25}$-B$_{50}$-P$_{25}$]$_{26\ KDa}$ | 60 | 1.0 | 24 | | ApoB | 0.59 | 0.07 | 1.22 | 0.10 |
| | 75 | 1.4 | 24 | | ApoB | 0.79 | 0.06 | 0.85 | 0.14 |
| | 100 | 1.6 | 24 | | ApoB | 0.52 | 0.16 | 0.62 | 0.14 |
| | 80 | 0.8 | 24 | | ApoB | 0.60 | 0.14 | 0.66 | 0.10 |
| [Nag-OH(PEG1)]$_{6.0\ KDa}$-[HPMA$_{90}$-PDSMA$_{10}$]$_{12.8\ KDa}$-[D$_{25}$-B$_{50}$-P$_{25}$]$_{25.2\ KDa}$ | 100 | 1.9 | 24 | | ApoB | 0.42 | 0.08 | 0.73 | 0.16 |
| | 80 | 1.0 | 24 | | ApoB | 0.70 | 0.14 | 0.96 | 0.20 |
| [Nag-OH(PEG3)$_{80}$-MAA$_{20}$]$_{7.5\ KDa}$-[HPMA$_{80}$-PDSMA$_{10}$-MAA$_{10}$]$_{9.5\ KDa}$-[D$_{25}$-B$_{50}$-P$_{25}$]$_{24.2\ KDa}$ | 100 | 1.7 | 24 | | ApoB | 0.48 | 0.28 | 0.92 | 0.18 |
| | 75 | 1.3 | 24 | | ApoB | 0.95 | 0.14 | 1.05 | 0.12 |

| Triblock Polymer-siRNA Conjugate In Vivo Knockdown Activity | | | | | | | | |
|---|---|---|---|---|---|---|---|---|
| | | | | | ApoB mRNA | | GAPDH mRNA | |
| Structure | polymer mg/kg | siRNA mg/kg | harvest timepoint | Special note | siRNA | Relative mRNA levels | st dev | Relative mRNA levels | st dev |
| [GALOH(PEG1)]$_{4.7\ KDa}$-[HPMA-PDSMA]$_{9.6\ KDa}$-[D$_{25}$-B$_{50}$-P$_{25}$]$_{30\ KDa}$ | 100 | 1.5 | 24 | | ApoB | 0.76 | 0.06 | 0.67 | 0.06 |
| | 80 | 0.8 | 24 | | ApoB | 0.71 | 0.12 | 0.85 | 0.18 |
| [GALOH(PEG3)]$_{5.3\ KDa}$-[HPMA-PDSMA]$_{8.3\ KDa}$-[D$_{25}$-B$_{50}$-P$_{25}$]$_{23\ KDa}$ | 100 | 1.9 | 24 | | ApoB | 0.54 | 0.08 | 1.10 | 0.16 |
| | 80 | 1.0 | 24 | | ApoB | 0.91 | 0.10 | 0.76 | 0.08 |
| [GAL-OH(PEG1)]$_{5.5\ KDa}$-[HPMA-E$_{90}$-PDSMA$_{10}$]$_{14\ KDa}$-[Imidazole$_{25}$-B$_{50}$-P$_{25}$]$_{20\ KDa}$ | 100 | 1.7 | 24 | | ApoB | 0.86 | 0.30 | 0.99 | 0.06 |
| | 50 | 0.8 | 24 | | ApoB | 0.98 | 0.04 | 0.99 | 0.22 |
| | 75 | 1.0 | 24 | | ApoB | 0.88 | 0.14 | 1.18 | 0.15 |
| | 50 | 0.7 | 24 | | ApoB | 0.87 | 0.22 | 1.12 | 0.18 |

Notes:
a: formulation stored at 4° C. for 7 days prior to administration.
b: Injection to C57 black mice.

Example 9

Synthesis of Tri-Block Polymer [PEGMA$_X$-BPAm$_y$]-[HPMA$_{90}$-PDSMA$_{10}$]-[D$_{25}$-B$_{50}$-P$_{25}$] and Post Polymerization Conjugation with Folate Targeting Ligand and siRNA A method for incorporating small molecule ligands (e.g., folate) into triblock polymers that target specific cell surface receptors is described. The first copolymer block contains a reactive amine (polymerized in its Boc-protected form, designated BPAm) and optionally a second hydrophilic monomer (e.g., PEGMA or HPMA). Following polymer synthesis the Boc protecting group is removed resulting in an amine that can be reacted with the activated small molecule targeting agent to form a stable conjugate. The mole % of BPAm (Y) and the mole % of the second hydrophilic monomer (X) in the polymer as well as the block size (Mn1) can be varied to achieve the most effective valency of the targeting molecule to optimize targeting efficiency. The structure synthesized is represented by formulas VII and V11.1

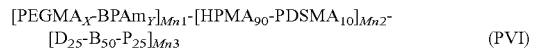

[PEGMA$_X$-BPAm$_Y$]$_{Mn1}$-[HPMA$_{90}$-PDSMA$_{10}$]$_{Mn2}$-[D$_{25}$-B$_{50}$-P$_{25}$]$_{Mn3}$  (PVI)

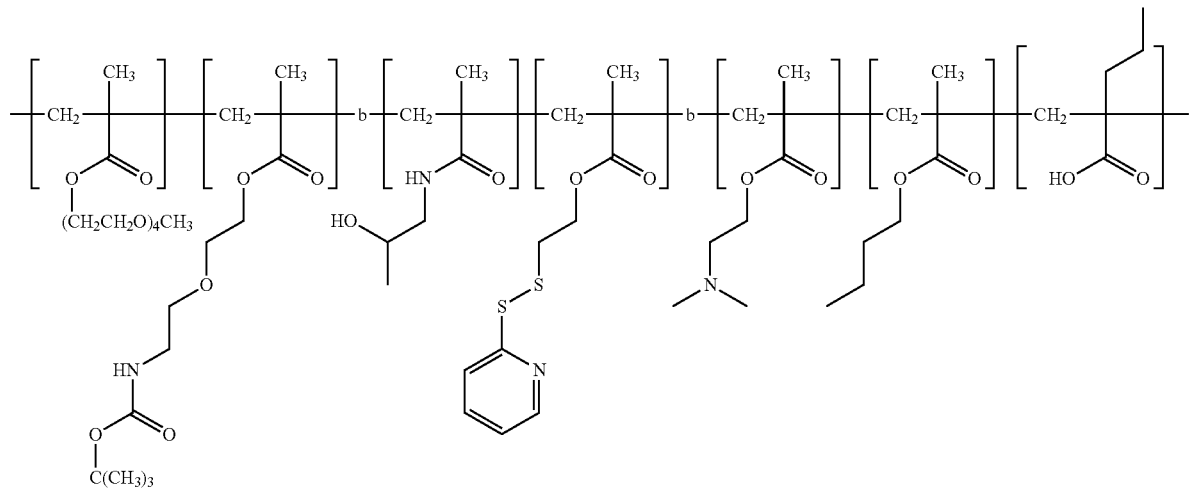

(PVI.1)

Example 9.1

Synthesis of BOC-protected Amine Vinyl Monomer

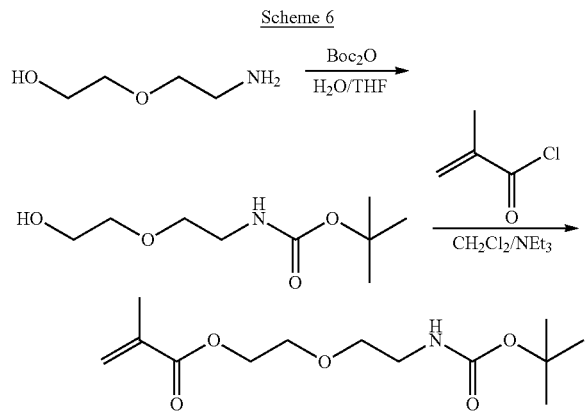

Scheme 6

The synthesis is represented in Scheme 6. To a solution of the amine (10.51 g, 100 mmol) in a mixture of 100 mL of water and 1 mL of satd. NaHCO$_3$ solution, a solution of Boc anhydride (22.94 g, 105 mmol) in 200 mL of THF is added. The mixture is allowed to stir at room temperature overnight. To the mixture, 100 mL of satd. NaHCO$_3$ solution and 400 mL of EtOAc are added. The organic layer is washed with satd. NaHCO$_3$, water, then dried over Na$_2$SO$_4$, filtered and evaporated. The residue is dried under vacuum to yield the crude product as a clear oil. The compound is used in the next step without purification.

The crude product from step 1 (19.80 g, 96.5 mmol) and triethylamine (16.1 mL, 115 mmol) is dissolved in anhydrous dichloromethane (180 ml), the solution is cooled to 0° C., and methacryloyl chloride (11.2 mL, 115 mmol) is added slowly via syringe at 0° C. under a nitrogen atmosphere. The reaction mixture is allowed to gradually warm up to room temperature and is stirred at room temperature overnight. The reaction is then diluted with sat. NaHCO$_3$ solution (150 ml) and dichloromethane (150 ml). The organic layer is separated, dried over Na$_2$SO$_4$, filtered and evaporated under vacuum. The product is purified by column chromatography on silica gel (ether/Hexanes:1/1). Product-containing fractions are pooled and evaporated (Rf 0.35). $^1$H NMR and TLC may show a small impurity (ca. 2-3%). The compound is purified on silica gel (EtOAc/hexanes 1/3). After evaporation of the product-containing fractions and drying, a clear colorless oil is obtained. The product is stored under air in a tightly-capped flask at −20° C. The structure is confirmed by $^1$H NMR (dmso-d6).

Example 9.2

Synthesis of [PEGMA$_X$-BPAm$_Y$]-CTA

The first block of the triblock polymer is synthesized and purified as described in Example 1. The feed ratios of the vinyl monomers for PEGMA and BPAm are selected to approximately reflect the desired composition. For example, a feed ratio of 50:50 or 80:20 may give a relative mole % of approximately 50% PEGMA and 50% BPAm or 80% PEGMA and 20% BPAm respectively for monomers of similar molecular reactivity. Fine tuning of the desired molar compositions is determined experimentally. The molecular weight of the first block can be adjusted to approximately 5-15 KDaltons depending of the desired valency of the targeting ligand and is determined experimentally. The structure is confirmed by $^1$H NMR (dmso-d6).

Example 9.2

Synthesis of [PEGMA$_X$-BPAm$_Y$]-[HPMA-PDSMA]-CTA

The second block of the triblock polymer is synthesized and characterized as described in Example 6.5, including [PEGMA$_X$-BPAm$_Y$]-CTA synthesized as described in Example 9.1. Typically the molar composition is 90% HPMA and 10% PDSMA produced by adjusting the feed ratios of the vinyl monomers in the polymerization reaction accordingly. Molecular weights of the second block are typically between 5-10 KDa. The structure is confirmed by $^1$H NMR (dmso-d6).

Example 9.3

Synthesis Of [PEGMA$_X$-BPAm$_Y$]-[HPMA$_{90}$-PDSMA$_{10}$]-[D$_{25}$-B$_{50}$-P$_{25}$]

The third block of the triblock polymer is synthesized and purified as described in Example 6.6, including [PEGMA$_X$-BPAm$_Y$]-[HPMA-PDSMA]-CTA in the polymerization reaction as the macro-CTA, synthesized as described in Example 9.2. Typically the molar composition is 25% DMAEMA, 50% BMA and 25% PAA produced by adjusting the feed ratios of the vinyl monomers in the polymerization reaction accordingly. Molecular weights of the third block are typically between 20-40 KDa. The structure is confirmed by $^1$H NMR (dmso-d6).

Example 9.4

BOC Group Deprotection of the Triblock Polymer

Prior to reacting the targeting block of the triblock polymer with activated targeting ligand, the BOC protecting group is removed to generate the reactive primary amines. After the dialysis step and evaporation (as described in Example 6.6) neat TFA is added under N$_2$ and the deprotection reaction is carried out for 2 hrs at room temperature followed by ether precipitation. The structure is confirmed by $^1$H NMR (dmso-d6).

Example 9.5

Conjugation of Folate Targeting Ligand to the First Block of the Triblock Polymer to Produce [PEGMA$_X$-MA(Folate)$_Y$]-[HPMA$_{90}$-PDSMA$_{10}$]-[D$_{25}$-B$_{50}$-P$_{25}$]

Folate is coupled through its γ carboxylic acid to a spacer unit, H$_2$NCH$_2$CH$_2$OCH$_2$CH$_2$NHBOC using a carbodiimide procedure. Folic acid (Sigma) is dissolved in dimethyl sulfoxide. To the resulting solution is added 1 to 3 fold molar excess of dicyclohexyl carbodiimide (DCC) and 5 molar equivalents of N-hydroxysuccinimide, and the reaction is stirred at room temperature for 16 hrs under N$_2$. The activated folate-NHS compound is isolated by precipitation with diethyl ether followed by washing with diethyl ether and acetone. The isolated compound is dried under vacuum and the structure confirmed by ¹H-NMR. The level of γ-carboxylate activation to α-carboxylate activation is approximately 3:1.

To the activated folate-NHS compound in dimethyl sulfoxide is added 1 to 2 fold molar excess of $H_2NCH_2CH_2OCH_2CH_2NHBOC$, together with 1 equivalent of triethylamine. The reaction is stirred at room temperature for 16 hrs under $N_2$. The Boc-amine modified folate is isolated by precipitation with diethyl ether followed by washing with diethyl ether. The isolated compound is dried under vacuum and the structure confirmed by ¹H-NMR.

Prior to reacting the folic acid derivative with the polymer, the Boc protecting group is removed to generate the reactive primary amine on the folic acid derivative as described in Example 9.4. The amine modified folate is isolated by precipitation with diethyl ether followed by washing with diethyl ether. The isolated compound is dried under vacuum and the structure confirmed by ¹H-NMR.

A 10-fold molar excess of carbonyl diimidazole (CDI) is added to the amine modified folate in dimethyl sulfoxide and the reaction is stirred at room temperature for 16 hrs. The resulting folate derived imidazole urea is isolated by precipitation with diethyl ether followed by washing with diethyl ether, to remove unreacted CDI and imidazole. A 5-fold molar excess of the imidazole urea is then mixed with the deprotected polymer (section 9.4) in dimethyl sulfoxide. After 16 hrs at room temperature, the product is isolated by lyophilization following dialysis against water (2000 MWCO dialysis membrane). The structure of the Folate containing triblock polymer is confirmed by ¹H-NMR.

Example 9.6

Conjugation of siRNA to the Second Block of the Triblock Polymer to Produce [PEGMA$_X$-MA(Folate)$_Y$]-[HPMA$_{90}$-PDS(siRNA)$_{10}$]-[D$_{25}$-B$_{50}$-P$_{25}$]

[PEGMA$_X$-MA(Folate)$_Y$]-[HPMA$_{90}$-(PDSMA-PDS(siRNA))$_{10}$]-[D$_{25}$-B$_{50}$-P$_{25}$]  (PVII)

(PVII.1)

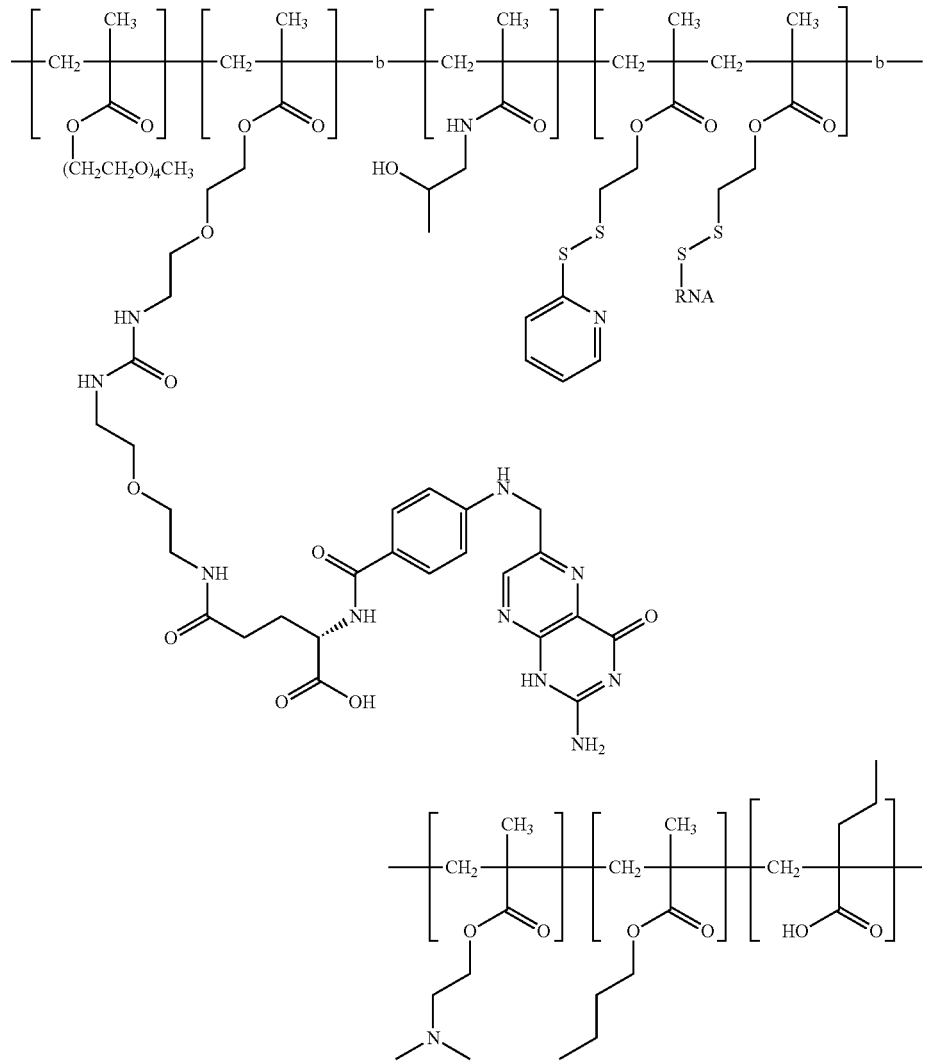

The final step in the construction of a targeted triblock polymer involves conjugating siRNA to the second block of the triblock polymer to produce the final polymer structure represented by formulas PVII and PVII.1. The conjugation reaction is carried out as described in Example 7. First, a thiolated (activated) siRNA is prepared (Example 7.1) which is then reacted with the PDS groups in the second block of the triblock polymer (Example 7.2) to form the polymer-siRNA conjugate.

The final triblock polymer containing a first block targeting the folate receptor and a second block containing conjugated siRNA is analyzed for biological activity (i.e., gene specific knockdown activity) as described in Example 8. Two different cell lines can be used, one expressing the specific folate receptor and the other a control cell line not expressing the folate receptor. Multiple cell lines have been described that can be used to demonstrate cell type-specific targeting and knockdown via the folate receptor (e.g., Low P S, Kularatne S A. Folate-targeted therapeutic and imaging agents for cancer. Curr Opin Chem. Biol. 2009 June; 13(3):256-62.)

Example 10

Triblock Polymers Comprising MAA Units in Hydrophilic Blocks

Alternatively, the triblock polymers were synthesized by the addition of methacrylic acid (MAA) to polymer blocks 1 and 2 as represented by formulas (PVIII) and (PIX). The addition of acidic residues increased the hydrophilicity/solubility of the polymer.

Example 10.1

Synthesis of Polymer PVIII

Step 1. Preparation of macroCTA [Nag-P3$_{80\%}$-co-MAA$_{20\%}$]

O-Acetyl-protected N-Acetyl galactosamine monomer Nag-P3-MA (1.5 g, 2.74 mmoles), MAA (0.059 g, 0.685 mmoles), ECT (22.5 mg, 0.0856 mmoles; 1:40 CTA:Monomers), AIBN (0.351 mg, 0.00214 mmoles; ECT:AIBN 40:1) and DMF (1.64 ml) were introduced under nitrogen in a sealed vial. The monomers concentration was 2.1 M. The mixtures were then degassed by bubbling nitrogen into the mixture for 30 minutes. They were placed in a heater block (Thermometer: 68° C.; display: 70-71; stirring speed 300 rpm). The reaction was left 9 hours 5 minutes. The reaction was stopped by placing the vial in ice and exposing the mixtures to air. The purification of the polymer was done by dialysis against methanol for 36 hours. The solvent was after removed. The resulting polymer was dried under vacuum for at least 6 hours. The structure and composition of the resulting macroCTA were confirmed by $^1$H-NMR. The molecular weight of the product (12.7 kDa) and its polydispersity (1.1) were determined by GPC analysis.

Step 2. Preparation of MacroCTA [Nag-P3$_{80\%}$-MAA$_{20\%}$]-b-[HPMA$_{82}$-PDSMA$_8$-MAA]

HPMA (0.556 g, 3.89 mmoles), PDSMA (0.097 g, 0.379 mmoles), [Nag-P380-MAA20] MacroCTA (0.30 g, 0.0315 mmoles; 1:150 CTA:Monomers), AIBN (0.52 mg, 0.00316 mmoles; CTA:AIBN 10:1) and DMF (1.52 ml) were introduced under nitrogen in a sealed vial. The monomers concentration was ~3.0 M. The mixtures were then degassed by bubbling nitrogen into the mixture for 30 minutes. They were placed in a heater block (Thermometer: 68° C.; display: 70-71; stirring speed 300 rpm). The reaction was allowed to proceed for 5 hours and then stopped by placing the vial in ice and exposing the mixtures to air. The purification of the polymer was done by dialysis against methanol for 36 hours. The solvent was removed, and the resulting polymer was dried under vacuum for at least 6 hours. The NMR spectrum showed the high purity of the product. No vinyl groups corresponding to the unreacted monomers were observed. The GPC analysis of the product gave the right molecular weight (19 KDa by triple detection, 93% of living ends by UV absorption) and good polydispersity (1.1).

Step 3. Preparation of protected [Nag-P3-MAA]-b-[HPMA-PDSMA-MAA]-b-[BMA-PAA-DMAEMA]

BMA (0.776 g, 5.458 mmoles), PAA (0.312 g, 2.73 mmoles), DMAEMA (0.429 g, 2.73 mmoles), MacroCTA (0.881 g, 0.02757 mmoles; 1:396 CTA:Monomers), AIBN (0.452 mg, 0.002757 mmoles; CTA:AIBN 10:1) and DMF (1.986 ml) were introduced under nitrogen into a sealed vial. The monomer concentration was 3 M. The mixtures were then degassed by bubbling nitrogen into the mixture for 30 minutes and placed into a heat block (Thermometer: 67-68° C.; display: 70-71; stirring speed 350 rpm). The reaction was allowed to proceed for 11 hrs (assuming 50-60% of conversion). The reaction was stopped by placing the vial in ice and exposing the mixture to air. The purification of the polymer was done by precipitation from Acetone/DMF 1:1 into hexane/ether 75/25 (three times). The resulting polymer was dried under vacuum for at least 8 hours. The NMR spectrum showed the high purity of the product. The molecular weight of the product (43.2 KD) and its polydispersity (1.9) were determined by GPC analysis.

Step 4: Deprotection of the N-Acetyl galactosamine polymer [Nag-P3-MAA]-b-[HPMA-PDSMA-MAA]-b-[BMA-PAA-DMAEMA].

To a 20 mL reaction glass vial the polymer prepared in step 3 (CD-02-22) (0.7 mg, 4225 μmol polymer) was added followed by anhydrous methanol (3.0 mL), anhydrous chloroform (1.5 mL) and sodium methoxide (90 mg, 1650 μmol, 6 equivalents relative to Nag). This mixture was stirred under an atmosphere of $N_2$ at RT for 1.0 h 15'. Then glacial acetic acid (540 μL, 695 μmol, 3 equivalents relative to N-Acetyl galactoseamine content of the polymer) was added to the reaction mixture followed by 2,2'-dipyridyl disulfide (15 mg, 68 μmol, 1 equivalent relative to pyridyl disulfide). This mixture was stirred a RT for 1.0 h under a flow of $N_2$ gas. After the capping with 2,2'-dipyridyl disulfide for 75 minutes, the reaction mixture was diluted with MeOH (5 mL) and filtered via simple gravity filtration. The filtered solution was transferred to a dialysis membrane with a 2000 g/mol MWCO and dialyzed against MeOH (4×1 L) over 18 h, followed by dialysis against miliQ water (5×4 L) over 20 h, followed by lyophilization. The NMR analysis was performed in $CD_3OD$ to confirm the polymer structure.

Since the pyridyl disulfide functionality on the polymer was difficult to detect by NMR spectroscopy, this functionality was quantified using UV/Vis absorption. The deprotected polymer (13.4 mg) was dissolved in EtOH (268 mL) providing a polymer solution at a concentration of 50 mg/mL. An aliquot of this polymer solution (20 μL, 1.0 mg, 6.35 μmol) was treated with an aqueous solution of 1.0 M dithiothreitol (10 μL, 10.0 μmol, DTT) for 10 min before being diluted with $H_2O$ (70 μL) giving a reduced polymer solution of 0.0635 M (6.35 μmol/100 uL=0.0635 mol/L). Since the expected incorporation of pyridyl disulfide should be 1.9% in the polymer, one would expect the concentration of the leaving group pyridine-2-thione should be 1.21 mM (i.e., 0.0635×0.019=0.00121 M) after the polymer is treated with DTT as described above. Since the molar absorptivity of pyridine-2-thione at 343 nm is $\epsilon=8.08\times10^3$ $M^{-1}$ $cm^{-1}$ (Hermanson, G. T. *Bioconjugate Techniques*, 1996, $1^{st}$ ed. Academic Press, an imprint of Elsevier, page 66 which is incorporated herein by reference) and the path length of the NanoDrop spectrometer used is 0.1 cm, the expected absorption for the reduced polymer solution above should be A=0.98 (i.e., A=8.08×10³ $M^{-1}$ $cm^{-1}$×0.1 cm×0.00153 M). After analysis of the reduced polymer solution by UV/Vis absorption the experimentally determined absorption was A=0.48 at 343 nm. This demonstrates the presence of pyridyl disulfide functionality in the polymer with the actual concentration of 0.93% total pyridyl disulfide incorporation in the polymer ([0.48/0.98]×1.9) compared to the 2.4% theoretically calculated.

Example 10.2

Synthesis of the Polymer PIX

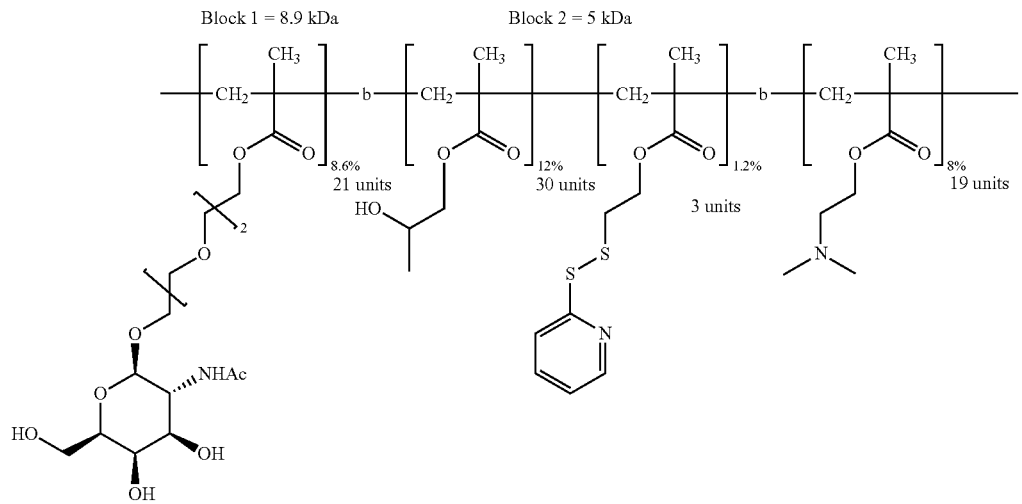

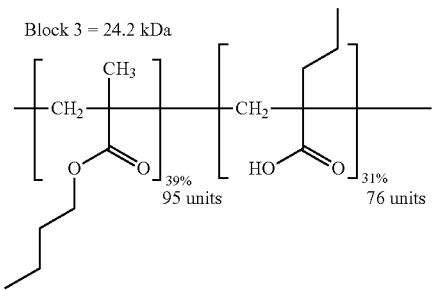

Block 3 = 24.2 kDa

Step 1. Synthesis of Poly (Nag-P3)

O-Acetyl-protected N-Acetyl galactosamine monomer with triethyleneglycol linker (Nag-P3-MA) (1.0 g, 1.83 mmoles), ECT (24.1 mg, 0.0913 mmoles), and AIBN (0.375 mg, 0.00228 mmoles; ECT:AIBN 40:1) and DMF (1.0 g) were introduced under nitrogen into a sealed vial. The mixture was degassed by bubbling nitrogen into the mixture for 30 minutes, then placed in a heat block (Thermometer: 67-68° C.; display: 70-71; stirring speed 350 rpm). The reaction was allowed to proceed for 9 hrs 5 minutes and was stopped by placing the vial in ice and exposing the mixture to air. The purification of the final polymer was done by dialysis against methanol for 2 days. No vinyl groups were observed in the NMR spectrum and the spectra confirmed the desired structure. As determined by GPC analysis: dn/dc=0.059234; Mn=11.8 kDa (~21 units); PDI=1.2.

Step 2. Synthesis of Polymer of the Targeted Structure Poly(Nag-P3)11.8 kDa-b-(HPMA-E-PDSMA)5 kDa].

HPMA-E (0.69 g, 4.79 mmoles), PDSMA (0.11 g, 0.47 mmoles), MacroCTA from step 1 (0.41 g, 0.0347 mmoles; 1:150 CTA:Monomers), AIBN (0.57 mg, 0.00347 mmoles; CTA:AIBN 10:1) and DMF (1.6 g) were introduced under nitrogen into a sealed vial. The monomer concentration was ~3 M. The mixture was then degassed by bubbling nitrogen into it for 30 minutes, then immersed in a heat block (Thermometer: 68° C.; display: 70-71; stirring speed 300 rpm). The reaction was allowed to proceed for 3 hours, and then stopped by placing the vial in ice and exposing the mixture to air. The purification of the polymer was done by dialysis against methanol for 24 hours. The solvent was removed, and the resulting polymer was dried under vacuum for at least 6 hours. The NMR spectrum showed high purity of the polymer and the presence of PDSMA. No chemical shifts of vinyl groups due to presence of unreacted monomers were observed. The GPC analysis gave a molecular weight of 16800 and a polydispersity of 1.1 for the resulting polymer.

Step 3. Synthesis of Nag-protected polymer [Nag-P3]$_{11.8kDa}$-b-[HPMA-E-92-PDSMA8]$_{5kDa}$-b-[BMA50-PAA40-DMAEMA10]$_{30kDa}$ BMA (0.596 g, 4.194 mmoles), PAA (0.383 g, 3.355 mmoles), DMAEMA (0.132 g, 0.839 mmoles), MacroCTA (0.300 g, 0.01852 mmoles; 1:453 CTA:Monomers), AIBN (0.304 mg, 0.001852 mmoles; CTA:AIBN 10:1) and DMF (1.5067 g) were introduced under nitrogen into a sealed vial. The monomers concentration was ~3 M. The mixture was degassed by bubbling nitrogen into the mixture for 30 minutes, then placed into a heat block (Thermometer: 67-68° C.; display: 70-71; stirring speed 350 rpm). The reaction was allowed to proceed for 21 hrs (assuming 50-60% of conversion). The reaction was stopped by placing the vial in ice and exposing the mixture to air. The purification of the polymer was done by precipitation from Acetone/DMF 1:1 into hexane/ether 75/25 (three times). The resulting polymer was dried under vacuum for at least 8 hours. The NMR showed pure polymer with the presence of PDSMA and no vinyl groups due to impurities of unreacted monomers. GPC analysis of the product gave dn/dc=0.058173; Mn=41.9 kDa; PDI=1.30.

Step 4: Deprotection.

To a 20 mL reaction glass vial the polymer from step 3 (440 mg, 2575 µmol polymer) was added followed by anhydrous methanol (2.0 mL), anhydrous chloroform (1 mL) and sodium methoxide (72 mg, 1329 µmol, 6 equivalents relative to Nag content of the polymer). This mixture was stirred under an atmosphere of $N_2$ at RT to 1.0 hr, then 2,2'-dipyridyl disulfide (34 mg, 154.5 µmol, 5 equivalents relative to pyridyl disulfide) was added to the reaction. This mixture was stirred a RT for 30 minutes.

After the capping with 2,2'-dipyridyl disulfide for 30 min, the reaction mixture was diluted with MeOH (5 mL). The filtered solution was transferred to a dialysis membrane with a 2000 g/mol MWCO and dialyzed against MeOH (4×1 L) over 18 h, followed by dialysis against miliQ water (3×4 L) over 10 h, followed by lyophilization. The NMR analysis was performed using $CD_3OD$, showing the presence of PDSMA signals. The pyridyl disulfide functionality on the polymer was also quantified using UV/Vis absorption. The final polymer (6.2 mg) was dissolved in EtOH (248 µL) providing a polymer solution at a concentration of 25 mg/mL. An aliquot of this polymer solution (20 µL, 0.5 mg, 3.125 µmol) was treated with an aqueous solution of 1.0 M dithiothreitol (10 µL, 10.0 µmol, DTT) for 10 min before being diluted with $H_2O$ (70 µL) giving a reduced polymer solution of 0.03125 M (3.125 µmol/100 uL=0.03125 mol/L). Since the expected incorporation of pyridyl disulfide should be 1.2% on the polymer one would expect the concentration of the leaving group pyridine-2-thione should be 0.375 mM (i.e., 0.03125×0.012=0.000375 M) after the polymer is treated with DTT as described above. Since the molar absorptivity of pyridine-2-thione at 343 nm is E=8.08×10$^3$ M$^{-1}$ cm$^{-1}$ (Hermanson, G. T. *Bioconjugate Techniques*, 1996, 1$^{st}$ ed. Academic Press, an imprint of Elsevier, page 66) and the path length of the NanoDrop spectrometer used is 0.1 cm the expected absorption for the reduced polymer solution above should be A=0.303 (i.e., A=8.08×10$^3$ M$^{-1}$ cm$^{-1}$×0.1 cm×0.000375 M). After analysis of the reduced polymer solution by UV/Vis absorption the experimentally determined absorption was A=0.345 at 343 nm. This demonstrated that the presence of the pyridyl disulfide functionality in the polymer with the actual concentration of 1.3% total pyridyl disulfide incorporation in the polymer ([0.345/0.303]×1.2) instead of the theoretically calculated 1.2% (100% retention of the pyridyldisulfide groups).

Example 11

Alternative Triblock Structures

Using the methods described above, the following additional triblock polymers can be prepared. In addition, it should be understood that HPMA-E (2-hydroxypropyl methacrylate or monomeric residue derived therefrom) may be substituted for HPMA in each of the following triblock polymers in which HPMA appears; solely in the interest of brevity, such additional structures are not repeated but shall be considered part of this disclosure:

[PAA$_{90}$-BA$_{10}$]$_{18K}$-[HPMA$_{90}$-PDSMA$_{10}$]$_{5D}$-[Folate]

[PAA$_{90}$-BA$_{10}$]$_{18K}$-[HPMA$_{80}$-MAA$_{10}$-PDSMA$_{10}$]$_{5K}$-[Folate]

Folate-[PEG]$_{2K}$-[HPMA$_{90}$-PDSMA$_{10}$]$_{12.0K}$-[D$_{25}$-B$_{50}$-P$_{25}$]$_{30K}$ Folate-[PEG]$_{2K}$-[HPMA$_{90}$-MAA$_{10}$-PDSMA$_{10}$]$_{12.0K}$-[D$_{25}$-B$_{50}$-P$_{25}$]$_{30K}$

[PEGMA$_{70}$-MAA(NHS)$_{30}$]-[DMAEMA]-[B-P-D]

[DMAEMA$_{70}$-MAA(NHS)$_{30}$]-[DMAEMA]-[B-P-D]

[Gal]-[HPMA-PDSMA]-[B-P-D]

[Gal-MAA]-[HPMA-PDSMA-MAA]-[B-P-D]

[NAcGal]-[HPMA-PDSMA]-[B-P-D]

[NAcGal-MAA]-[HPMA-PDSMA-MAA]-[B-P-D]

[Gal]-[D]-[B-P-D]

[NAcGal]-[D]-[B-P-D]

[Gal-MAA]-[D]-[B-P-D]

[NAcGal-MAA]-[D]-[B-P-D]

[Gal-D]-[D]-[B-P-D]

[NAcGal-D]-[D]-[B-P-D]

[Gal]-[PA]-[B-P-D]

[Gal]-[HPMA-PA]-[B-P-D]

[Gal-MAA]-[PA]-[B-P-D]

[Gal-MAA]-[HPMA-PA]-[B-P-D]

[Gal-D]-[PA]-[B-P-D]

[Gal-D]-[HPMA-PA]-[B-P-D]

[NAcGal]-[PA]-[B-P-D]

[NAcGal]-[HPMA-PA]-[B-P-D]

[NAcGal-MAA]-[PA]-[B-P-D]

[NAcGal-MAA]-[HPMA-PA]-[B-P-D]

[NAcGal-D]-[PA]-[B-P-D]

[NAcGal-D]-[HPMA-PA]-[B-P-D]

[PAA-BA]-[HPMA-PDSMA]-[Folate]

[PAA-BA]-[HPMA-MAA-PDSMA]-[Folate]

Folate-[PEG]-[HPMA-PDSMA]-[D-B-P]

Folate-[PEG]-[HPMA-MAA-PDSMA]-[D-B-P]

---

What is claimed is:

1. A composition comprising a block copolymer associated with a polynucleotide, the block copolymer consisting of a first, a second and a third compositionally distinct blocks, wherein the first block is a hydrophilic polymer block consisting of repeat units derived from polymerization of a monomer of Formula IV

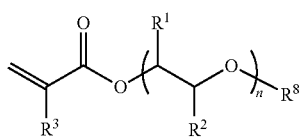

(IV)

wherein
each $R^1$ and $R^2$, is hydrogen,
$R^3$ is $C_1$-$C_3$ alkyl,
n is an integer ranging from 2 to 20,
$R^8$ is $(CR^1R^2)_m R^9$, wherein m is 0-10, and
$R^9$ is a targeting group,
wherein the second block is located between the first and third blocks and is associated with the polynucleotide, wherein the second block consists of a plurality of monomeric residues of amino($C_1$-$C_6$)alkyl-methacrylate, N-($C_1$-$C_6$)alkyl-amino($C_1$-$C_6$)alkyl-methacrylate, N,N-di($C_1$-$C_6$)alkyl-amino($C_1$-$C_6$)alkyl-methacrylate, or a combination thereof, or wherein the second block is a random copolymer consisting of two compositionally distinct repeat units, wherein one of said repeat units is a monomeric residue of 2-hydroxypropyl methacrylate, N-(2-propyl)methacrylamide, or N-propylmethacrylamide, and the other of said repeat units has Formula 1

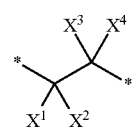

Formula 1 wherein
* designates the point of attachment of the repeat unit of Formula 1 to other repeat units;
each of $X^1$ and $X^2$ is hydrogen;
$X^3$ for Formula 1 within the second block is alkyl, and $X^4$ is —C(O)O$X^{45}$, wherein $X^{45}$ is a disulfide substituted alkyl moiety, and
wherein the third block is a hydrophobic polymer block consisting of repeat units having Formulae 1A, 1E, and 1C

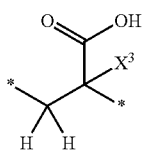
Formula 1A

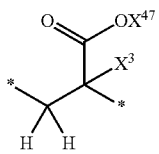
Formula 1E

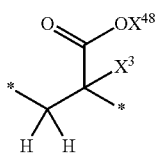
Formula 1C wherein * designates the point of attachment of the repeat units of Formula 1A, 1E, and 1C to other repeat units, $X^3$ for Formula 1A is propyl, $X^3$ for each of Formulae 1E and 1C is methyl, $X^{47}$ is butyl, and $X^{48}$ is N,N-dimethylaminoethyl.

2. The composition of claim 1 wherein the ratio of the number of repeat units having Formula 1A to the number of repeat units corresponding to Formula 1E in the third block is between about 20:1 and 1:4, respectively.

3. The composition of claim 1 wherein the number of repeat units having Formula 1A in the third block is at least equal to the number of repeat units having Formula 1C in third block.

4. The composition of claim 1 wherein the polynucleotide is a deoxyribonucleotide, an siRNA, an antisense oligonucleotide, a dicer substrate, an miRNA, an aiRNA or an shRNA.

5. The composition of claim 4 wherein the polynucleotide is an siRNA.

6. A pharmaceutical composition comprising the composition of claim 1 and a pharmaceutically acceptable excipient.

7. The composition of claim 1 wherein $X^{45}$ comprises the polynucleotide, and the polynucleotide is covalently bound to the composition through the disulfide moiety of $X^{45}$.

8. The composition of claim 1 wherein $X^{45}$ is pyridyl disulfide substituted ethyl.

9. The composition of claim 1 wherein the targeting moiety group is galactose, N-acetyl galactosamine, or folate.

10. A composition comprising a polymeric micelle and a polynucleotide associated with the micelle, the micelle comprising a plurality of block copolymers consisting of
(i) a first block, wherein the first block is a hydrophilic polymer block consisting of repeat units derived from polymerization of a monomer of Formula IV

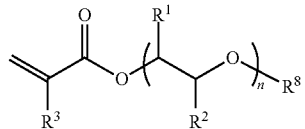
(IV)

wherein
each $R^1$ and $R^2$ is hydrogen,
$R^3$ is $C_1$-$C_3$ alkyl,
n is an integer ranging from 2 to 20,
$R^8$ is $(CR^1R^2)_m R^9$, wherein m is 0-10, and
$R^9$ is a targeting group,
(ii) a second block between the first block and a third block, wherein the second block is associated with the polynucleotide, wherein the second block consists of a plurality of monomeric residues of amino($C_1$-$C_6$)alkyl-methacrylate, N-($C_1$-$C_6$)alkyl-amino($C_1$-$C_6$)alkyl-methacrylate, N,N-di($C_1$-$C_6$)alkyl-amino($C_1$-$C_6$)alkyl-methacrylate, or a combination thereof, or wherein the second block is a random copolymer consisting of two compositionally distinct repeat units, wherein one of said repeat units is a monomeric residue of 2-hydroxy-propyl methacrylate, N-(2-propyl)methacrylamide, or N-propylmethacrylamide, and the other of said repeat units has Formula 1

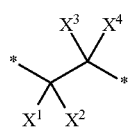
Formula 1 wherein
* designates the point of attachment of the repeat unit of Formula 1 to other repeat units;
each of $X^1$ and $X^2$ is hydrogen;
$X^3$ for Formula 1 within the second block is alkyl, and
$X^4$ is —C(O)O$X^{45}$, wherein $X^{45}$ is a disulfide substituted alkyl moiety, and
(iii) a third block, wherein the third block is a polymer block consisting of repeat units having Formulae 1A, 1E, and 1C

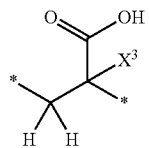
Formula 1A

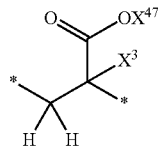
Formula 1E

Formula 1E
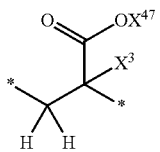

Formula 1C
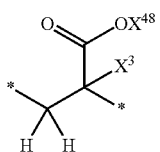

wherein * designates the point of attachment of the repeat units of Formula 1A, 1E, and 1C to other repeat units, $X^3$ for Formula 1A is propyl, $X^3$ for each of Formulae 1E and 1C is methyl, $X^{47}$ is butyl, and $X^{48}$ is N,N-dimethylaminoethyl, and wherein the micelle is stable in an aqueous medium at pH 7.4.

11. The composition of claim 10 wherein the polynucleotide is a deoxyribonucleotide, an siRNA, an antisense oligonucleotide, a dicer substrate, an miRNA, an aiRNA or an shRNA.

12. A method for intracellular delivery of a polynucleotide, comprising transfecting a cell with a composition of claim 1

* * * * *